US010357547B2

(12) United States Patent
Offerhaus et al.

(10) Patent No.: US 10,357,547 B2
(45) Date of Patent: Jul. 23, 2019

(54) COMBINATION TREATMENT FOR ATOPIC DERMATITIS

(71) Applicant: MICREOS HUMAN HEALTH B.V., The Hague (NL)

(72) Inventors: Mark Leonard Offerhaus, The Hague (NL); Fritz Eichenseher, CH-Zürich (CH); Martin Johannes Loessner, Ebmatingen (CH)

(73) Assignee: Micreos Human Health B.V., The Hague (NL)

( * ) Notice: Subject to any disclaimer, the term of this patent is extended or adjusted under 35 U.S.C. 154(b) by 152 days.

(21) Appl. No.: 14/904,387

(22) PCT Filed: Jul. 10, 2014

(86) PCT No.: PCT/NL2014/050470
§ 371 (c)(1),
(2) Date: Jan. 11, 2016

(87) PCT Pub. No.: WO2015/005787
PCT Pub. Date: Jan. 15, 2015

(65) Prior Publication Data

US 2016/0151463 A1 Jun. 2, 2016

(30) Foreign Application Priority Data

Jul. 11, 2013 (EP) .................................... 13176034

(51) Int. Cl.

| | |
|---|---|
| ***A61K 38/47*** | (2006.01) |
| ***A61K 38/16*** | (2006.01) |
| ***A61K 45/06*** | (2006.01) |
| ***A61K 31/573*** | (2006.01) |
| ***A61K 31/56*** | (2006.01) |
| ***A61K 38/21*** | (2006.01) |

(52) U.S. Cl.
CPC .............. *A61K 38/47* (2013.01); *A61K 31/56* (2013.01); *A61K 31/573* (2013.01); *A61K 38/162* (2013.01); *A61K 38/217* (2013.01); *A61K 45/06* (2013.01); *C12Y 302/01017* (2013.01)

(58) Field of Classification Search
None
See application file for complete search history.

(56) References Cited

U.S. PATENT DOCUMENTS

2002/0146402 A1* 10/2002 Fischetti ................ C12N 9/503 424/94.1
2013/0004476 A1* 1/2013 Grallert ................ C12N 9/2462 424/94.3

FOREIGN PATENT DOCUMENTS

WO WO 2009/035303 A2 3/2009
WO WO 2011/073437 A2 6/2011
WO WO 2012/150858 A1 11/2012

OTHER PUBLICATIONS

Lin et al., "Role of Bacterial Pathogens in Atopic Dermatitis", Clinic. Rev. Allerg. Immunol., 2007, vol. 33, pp. 167-177. DOI 10.1007/s12016-007-0044-5.*

Abaev, I., et al., "Staphylococcal Phage 2638A endolysin is lytic for *Staphylococcus aureus* and harbors an inter-lytic-domain secondary translational start site," *Applied Microbiology and Biotechnology*, 97(8): 3449-3456, Springer, Germany (2013).

Choudhury, R., et al. "Staphylococcal Infection, Antibiotic Resistance and Therapeutics," in Staphylococcal Infection, Antibiotic Resistance and Therapeutics, Antibiotic Resistant Bacteria—A Continuous Challenge in the New Millennium, Dr. Marina Pana (Ed.), pp. 247-272, InTech, Croatia (2012), Accessed at: http://cdn.intechopen.com/pdfs/34694/InTechStaphylococcal_infection_antibiotic_resistance_and_therapeutics.pdf, accessed on Apr. 11, 2016.

"Doorbraak in ontstekingsbestrijding," *Paradermica Tijdschrifi Voor Paramedische Dermatologie*, vol. Jun. 13, pp. 16-19, Paradermica, Netherlands (2013).

Fenton , M. et al., "Bacteriophage-Derived Peptidase $CHAP_K$ Eliminates and Prevents Staphylococcal Biofilms," *International Journal of Microbiology*, vol. 2013, Article ID: 625341, 8 pages, Hindawi Publishing Corporation, Egypt (2013).

Friedman, B-C., and Goldman, R.D., et al., "Anti-staphylococcal treatment in dermatitis," *Canadian Family Physician* 57(6): 669-671, The College of Family Physicians of Canada, Canada (2011).

Gladskin, "Bacterial skin balance," May 3, 2013, Accessed at: https://web.archive.org/web/20130503020820/http://www.gladskin.com/en/content/HowItWorks, accessed on Apr. 13, 2016.

Hung, S.H., et al., "Staphylococcus colonization in atopic dermatitis treated with fluticasone or tacrolimus with or without antibiotics," *Annals of Allergy, Asthma & Immunology* 98(1): 51-56, American College of Allergy, Asthma & Immunology, United States (2007).

International Search Report and Written Opinion for International Application No. PCT/NL2014/050470, European Patent Office, Netherlands, dated Oct. 30, 2014, 12 pages.

Loessner, M.J., et al., "C-terminal domains of *Listeria monocytogenes* bacteriophage murein hydrolases determine specific recognition and high-affinity binding to bacterial cell wall carbohydrates," *Molecular Microbiology* 44(2):335-49, Blackwell Science Ltd., United States (2002).

(Continued)

*Primary Examiner* — Suzanne M Noakes
(74) *Attorney, Agent, or Firm* — McDonnell Boehnen Hulbert & Berghoff LLP

(57) ABSTRACT

The invention relates to the field of medicine, specifically to the field of treatment of dermatitis or eczema, even more specifically to the field of treatment of atopic dermatitis. The invention relates to a novel composition and a novel kit of parts, both comprising an anti-inflammatory compound and a compound specifically targeting a bacterial cell, preferably a gram positive bacterial cell. The invention further relates to said composition and/or kit of parts for medical use, preferably for treating an individual suffering from eczema.

9 Claims, No Drawings

Specification includes a Sequence Listing.

(56) References Cited

OTHER PUBLICATIONS

A.C. Fluit, et al., "Killing and lysis of *Staphylococcus aureus* and other staphylococci by an endolysin," Department of Medical Microbiology, University Medical Center Utrecht, 2012.

David N. Abarbanel, et al., "Immunomodulatory effect of vancomycin on Treg in pediatric inflammatory bowel disease and primary sclerosing cholangitis," National Institutes of Health Public Access, Author Manuscript, Feb. 2013. J. Clin. Immun., 33(2), 397-406.

Maciej Siedlar, et al., "Vancomycin down-regulates lipopolysaccharide-induced tumour necrosis factor alpha (TNFα) production and TNFα-mRNA accumulation in human blood monocytes," Elsevier Science B.V., Immunopharmacology 35 (1997) 265-271.

* cited by examiner

COMBINATION TREATMENT FOR ATOPIC DERMATITIS

FIELD OF THE INVENTION

The invention relates to the field of medicine, specifically to the field of treatment of dermatitis or eczema, even more specifically to the field of treatment of atopic dermatitis. The invention relates to a novel composition and a novel kit of parts, both comprising an anti-inflammatory compound and a compound specifically targeting a bacterial cell, preferably a gram positive bacterial cell. The invention further relates to said composition and/or kit of parts for medical use, preferably for treating an individual suffering from eczema.

BACKGROUND OF THE INVENTION

Eczema is a common skin condition characterized by red, itchy skin and small blisters also known in the art as skin rash or rash or dermatitis. There is no cure for eczema, but there are many treatments, ranging from special diets to emollients and immunosuppressive ointments like e.g. corticosteroid ointment. While corticosteroids, such as hydrocortisone or clobetasol propionate (topical, oral or intradermal administration) usually bring about improvements, they also may have side effects. Prolonged use of topical corticosteroids is thought to increase the risk of side effects, the most common of which is the skin becoming thin and fragile (atrophy). Because of this, if used on the face or other delicate skin, a low-strength steroid should be used or applied less frequently. Additionally, high-strength steroids used over large areas, or under occlusion, may be absorbed into the body, causing hypothalamic-pituitary-adrenal axis suppression (HPA axis suppression).

Due to the impaired skin barrier in atopic dermatitis an increase in skin infections with bacteria such as *Staphylococcus aureus* or fungi might be the result. For more severe cases, dermatologists may also prescribe either topical or oral conventional antibiotics such as penicillin, streptomycin and chloramphenicol. The antibiotics prevent infection that can result from impaired skin barrier such as cracked skin. *S. aureus* colonization or infection is the most common cause of increased eczema severity. The effectiveness of antibiotic treatments varies from person to person. The well known disadvantages of conventional antibiotics are a-specificity, i.e. also non-pathogenic and/or beneficial bacteria are killed, and the risk of developing resistance, not only by the target bacterial cells but possibly also by other pathogenic bacteria. Furthermore, conventional, systemic antibiotic treatment can interact with other drugs, including contraceptive pills. Certain antibiotics cannot be combined with the use of alcohol. Accordingly, there is a need for improved treatment of eczema.

DESCRIPTION OF THE INVENTION

In a first aspect, the present invention provides for a novel composition comprising a first and a second compound, wherein said first compound is an anti-inflammatory compound and said second compound is a compound specifically targeting a bacterial cell, preferably a gram positive bacterial cell. Preferably, said gram positive bacterial cell is a *Staphylococcus*, more preferably a *Staphylococcus aureus*. Preferably, said composition is a medicament preferably for use in the treatment of eczema, most preferably for use in the treatment of atopic dermatitis, as further detailed herein. The state of the art for treating eczema is using immunosuppressive agents like corticosteroids and if indicated antibiotics topical or systemic. The present invention provides for a novel composition comprising both an anti-inflammatory compound and a compound specifically targeting a bacterial cell, preferably a gram positive bacterial cell, preferably a *Staphylococcus aureus*, which combats most, if not all, of the disadvantages of using either an effective dosage regime of a corticosteroid and/or a conventional antibiotic alone or in combination and provides a unexpected synergy. In comparison to the use of an immunosuppressive agent alone like a corticosteroid alone, a composition of the invention decreases the risk and/or is more effective by combating eczema-related and/or corticosteroid induced infections induced by a bacterial cell, such as a gram positive bacterial cell, preferably *Staphylococcus aureus*. Furthermore, in comparison to the use of a corticosteroid alone, a composition according to the invention may be as effective as using a corticosteroid alone while making use of a lower dosage and/or a shorter administration regimen resulting in a shorter exposure time of the corticosteroid thereby reducing possible side-effects like the risk of skin atrophy, hypothalamic-pituitary-adrenal axis suppression (HPA axis suppression) and/or (increased) skin infection.

In comparison to the use of a corticosteroid in combination with conventional antibiotics and/or conventional antibiotics alone, the composition of the present invention selectively specifically targets a bacterial cell, preferably a gram positive bacterial cell, preferably a *Staphylococcus*, more preferably a *Staphylococcus aureus*, without affecting surrounding commensal and/or beneficial microflora. In addition, the risk of developing resistance against antibiotics is diminished or at least reduced since lower amounts of antibiotics or even no antibiotics at all are used.

An agent that specifically targets a gram positive bacterial cell preferably is an agent that shows at least 2, 5, 10, 50 or 100 times higher lytic activity towards a gram positive bacterial cell as compared to a gram negative bacterial cell. Preferably, an agent that specifically targets a gram positive bacterial cell is an agent that does not affect a gram negative bacterial cell in a concentration that is affective in lysing a gram positive bacterial cell. An agent that specifically targets a *Staphylococcus* bacterial cell preferably is an agent that shows at least 2, 5, 10, 50 or 100 times higher lytic activity towards a *Staphylococcus* bacterial cell as compared to a non-*Staphylococcus* bacterial cell. Preferably, an agent that specifically targets a *Staphylococcus* bacterial cell is an agent that does not affect a non-*Staphylococcus* bacterial cell in a concentration that is effective in lysing a *Staphylococcus* bacterial cell. An agent that specifically targets a *Staphylococcus aureus* bacterial cell preferably is an agent that shows at least 2, 5, 10, 50 or 100 times higher lytic activity towards a *Staphylococcus aureus* bacterial cell as compared to a non-*Staphylococcus aureus* bacterial cell. Preferably, an agent that specifically targets a *Staphylococcus aureus* bacterial cell is an agent that does not affect a non-*Staphylococcus aureus* bacterial cell in a concentration that is effective in lysing a *Staphylococcus aureus* bacterial cell. Lytic activity is preferably assessed as exemplified herein.

Preferably, the invention provides a composition comprising a first and a second compound, wherein said first compound is an anti-inflammatory compound and said second compound is a compound specifically targeting a bacterial cell, preferably a gram positive bacterial cell, and wherein said second compound comprises at least one cell wall binding domain specifically binding the peptidoglycan cell wall of said bacterial cell, preferably gram positive bacterial cell. A cell wall-binding domain of the present invention is defined as an element, preferably a polypeptide within said second compound that directs said second compound to the bacterial wall of a bacterial cell.

A cell wall-binding domain encompassed within the present invention may be any cell wall-binding domain known by the person skilled in the art. Preferably, a cell wall-binding domain of the present invention is an element, preferably a polypeptide within said second compound, that directs said second compound to the peptidoglycan cell wall of a gram-positive bacterial cell, preferably the peptidoglycan cell wall of a *Staphylococcus* bacterial cell, more preferably the peptidoglycan cell wall of a *Staphylococcus aureus* bacterial cell.

Preferably, the invention provides a composition comprising a first and a second compound, wherein said first compound is an anti-inflammatory compound and said second compound is a compound specifically targeting a bacterial cell, preferably a gram positive bacterial cell, and wherein said second compound comprises at least one cell wall binding domain specifically binding the peptidoglycan cell wall of *Staphylococcus*, more preferably, a *Staphylococcus aureus*.

Binding of a domain to the peptidoglycan cell wall of *Staphylococcus* genera may be assessed using assays well known to the person skilled in the art. In a preferred embodiment, an immunohistochemical technique and/or a gene fusion technique resulting in labelled constructs are used for assessing specific binding of compounds such as peptides, polypeptides, proteins or bacteriophages to the peptidoglycan cell wall of *Staphylococcus* genera. Quantification methods of signals used in the above mentioned immunohistochemical or fusion techniques are well known in the art.

In one embodiment, *Staphylococcus* peptidoglycan cell wall-binding is quantified using a fluorescent fusion construct comprising a cell wall-domain of interest. Such a cell wall-binding assay is described in detail by Loessner et al (Molecular Microbiology 2002, 44(2): 335-349). In this assay a solution comprising said fluorescent fusion construct or a negative control, preferably Green Fluorescent Protein (GFP), is subjected to *Staphylococcus* cells, preferably *S. aureus* cells, more preferably *S. aureus* BB255 for an indicated time period where after the cells are sedimented by centrifugation together with the bound fluorescent fusion constructs. The fluorescent signal of the *Staphylococcus* cells exposed to a fluorescent fusion construct subtracted by the fluorescence signal of the *Staphylococcus* cells exposed to a negative control, preferably GFP, is a measure for cell binding as meant in this disclosure. Preferably, within the context of the invention, a domain is said to bind the peptidoglycan cell wall of *Staphylococcus* genera when using this assay an increase in fluorescent signal of the sedimented cells above the negative control as defined herein is detected. Preferably, the invention relates to a cell wall-binding domain which exhibits binding as defined herein of at least 50, 60, 70, 80, 90 or 100, 150 or 200% of peptidoglycan cell wall-binding of *S. aureus* bacteriophage Φ2638a endolysin (Ply2638 endolysin defined by SEQ ID NO: 2) preferably encoded by SEQ ID NO: 1. Preferably, a fusion construct as represented by SEQ ID NO: 95 and encoded by SEQ ID NO: 96 serves as a positive control in this assay. An overview of all sequences included and their SEQ ID NO is given in table 2.

Preferably, the invention provides a composition comprising a first and a second compound, wherein said first compound is an anti-inflammatory compound and said second compound is a compound specifically targeting a bacterial cell, preferably a gram positive bacterial cell, and wherein said second compound comprises at least one cell wall binding domain that originates from or is a homologue of a *Staphylococcus* phage endolysin, preferably said *Staphylococcus* phage endolysin is selected from, but not limited to, *S. aureus* bacteriophage Φ2638a endolysin, *S. aureus* bacteriophage Φ11 endolysin, *S. aureus* bacteriophage ΦTwort endolysin, *S. haemolyticus* JCSC1435, *S. aureus* Phage K endolysin, *S. warneri* phage WMY endolysin, *S. aureus* phage NM3 endolysin and *S. aureus* 80alpha endolysin.

Also preferred is a cell wall binding domain originating from or a homologue of *S. simulans* lysostaphin (represented by SEQ ID NO: 76, preferably encoded by SEQ ID NO: 75). A known homologue of *S. simulans* lysostaphin having cell wall binding properties is *S. capitis* ALE-1 enzyme.

Preferably, said cell wall binding domain has at least 80% identity to any of SEQ ID NO: 4, 6 or 8 and/or wherein said one or more enzymatic active domains has at least 80% identity to any of SEQ ID NO: 10, 12, 14, 16, 18, 98 or 100. A preferred cell wall-binding domain of the present invention is a cell wall-binding domain having at least 80, 81, 82, 83, 84, 85, 86, 87, 88, 89, 90, 91, 92, 93, 94, 95, 96, 97, 98, 99 or 100% identity with the cell wall binding domain of *S. simulans* lysostaphin defined herein by SEQ ID NO: 4 and preferably encoded by SEQ ID NO: 3. Also preferred is a cell wall-binding domain isolated from a native *Staphylococcus* bacteriophage endolysin. Also preferred is a cell wall-binding domain of the present invention that has at least 80, 81, 82, 83, 84, 85, 86, 87, 88, 89, 90, 91, 92, 93, 94, 95, 96, 97, 98, 99 or 100% identity with the cell wall-binding domain of *S. aureus* bacteriophage Φ2638a endolysin defined herein by SEQ ID NO: 6 and preferably encoded by SEQ ID NO: 5. Also preferred is a cell wall-binding domain isolated from a native *Staphylococcus aureus* phage phiNM3 endolysin. Preferably, a cell wall-binding domain of the present invention has at least 80, 81, 82, 83, 84, 85, 86, 87, 88, 89, 90, 91, 92, 93, 94, 95, 96, 97, 98, 99 or 100% identity with the cell wall-binding domain of *S. aureus* phage phiNM3 endolysin defined herein by SEQ ID NO: 8 and preferably encoded by SEQ ID NO: 7.

Preferably, the invention provides for a composition comprising a first and a second compound, wherein said first compound is an anti-inflammatory compound and said second compound is a compound specifically targeting a bacterial cell, preferably a gram positive bacterial cell, wherein said second compound comprises one or more enzymatic active domains exhibiting target bond specificity. 'An enzymatic active domain' is defined herein is a domain having lytic activity, preferably exhibiting peptidoglycan hydrolase activity. Lytic activity can be assessed by methods well known by the person skilled in the art. In an embodiment, lytic activity is assessed spectrophotometrically by measuring the drop in turbidity of substrate cell suspensions. Turbidity is assessed by measuring optical density at a wavelength of 595 nm, typically a culture as turbid when it exhibits an optical density of at least 0.3 OD at a wavelength of 595 nm. Preferably, lytic activity is assessed spectrophotometrically measuring the drop in turbidity of a *S. aureus* suspension, wherein turbidity is quantified by measuring $OD_{595}$ spectrophotometrically (Libra S22, Biochrom). More preferably, 200 nM polypeptide comprising an enzymatic active domain of the invention as identified herein is incubated together with an *S. aureus* suspension having an initial $OD_{595}$ of 1±0.05, as assessed spectrophotometrically (Libra S22, Biochrom), in PBS buffer pH 7.4, 120 mM sodium chloride for 30 min at 37° C. The drop in turbidity is calculated by subtracting the $OD_{595}$ after 30 min of incubation from the $OD_{595}$ before 30 min of incubation. Within the context of the invention a polypeptide comprising an enzymatic active domain of the invention as identified herein will be said to have lytic activity if, when using this assay, a drop in turbidity of at least 10, 20, 30, 40, 50 or 60% is detected. Preferably, a drop in turbidity of at least 70% is detected. Preferably, a polypeptide comprising an enzymatic active domain of the invention exhibits a lytic activity of at least 30, 40, 50, 60, 70, 80, 90, 100, 150 or 200% or more of a lytic activity of *S. aureus* bacteriophage Φ2638a endolysin (Ply2638 endolysin identified by SEQ ID NO: 2) preferably encoded by SEQ ID NO: 1.

Preferably, the invention provides for a composition comprising a first and a second compound, wherein said first compound is an anti-inflammatory compound and said second compound is a compound specifically targeting a bacterial cell, preferably a gram positive bacterial cell, wherein said second compound comprises one or more enzymatic active domains exhibiting target bond specificity, and wherein said target bond is an essential bond in a peptidoglycan layer of said bacterial cell, preferably gram positive bacterial cell. An essential bond in a peptidoglycan layer of a bacterial cell, preferably a gram-positive bacterial cell is defined herein as a linkage within said peptidoglycan that is essential for said peptidoglycan to provide said bacterial cell shape and a rigid structure resistance to osmotic shock. Preferably, said essential bond in a peptidoglycan layer of a gram-positive bacterial cell is a bond between a D-alanine of the stem peptide and a glycine of the cross-bridge peptide (defined herein also as a bond between an N-terminal alanine and a glycine), a bond in a pentaglycin cross-bridge (defined herein also as a pentyglycin bridge glycyl-glycyl bond, a bond between an N-acetylmuramoyl and an L-alanine or a bond between an N-acetylmuramine and a N-acetylglucosamine or between a N-acetlyglucosamine and an N-acetylmuramine. Other preferred essential bonds in a peptidoglycan layer of a gram-positive bacterial cell are a bond in a gamma-glutamyl stem peptide, a bond between an L-alanyl-iso-D-glutamic acid in a stem peptide and a bond between an iso-D-glutamic acid-L-Lysine in a stem peptide.

Most native *Staphylococcus* bacteriophage endolysins exhibiting peptidoglycan hydrolase activity consist of a C-terminal cell wall-binding domain (CBD), a central N-acetylmuramoyl-L-Alanine amidase domain, and an N-terminal alanyl-glycyl endopeptidase domain with cysteine, histidine-dependent amidohydrolases/peptidase (CHAP) homology, or in case of Ply2638, of an N-terminal glycyl-glycine endopeptidase domain with Peptidase_M23 homology, the latter three domains exhibiting peptidoglycan hydrolase activity each with distinct target bond specificity and generally named herein as enzymatically active domains. Preferably, said one or more enzymatic active domains is selected from or is a permutation of a domain of the group consisting of a cysteine, histidine dependent amidohydrolases/peptidase domain, an endopeptidase domain, an amidase domain and a glycosylhydrolase domain. Said glycosylhydrolase domain can be a muramidase domain or a glycosaminidase domain.

Preferably, said CHAP domain cleaves a bond between an N-terminal alanyl and a glycyl within a peptidoglycan layer. More preferably, said CHAP domain specifically cleaves a bond between an N-terminal alanyl and a glycyl within a peptidoglycan layer. Preferably, said endopeptidase domain cleaves pentaglycin bridge glycyl-glycyl bond within a peptidoglycan layer. More preferably, said endopeptidase domain specifically cleaves pentaglycin bridge glycyl-glycyl bond within a peptidoglycan layer. Preferably, said amidase domain cleaves a bond between a central N-acetlymuramoyl and an L-Alanine within a peptidoglycan layer. More preferably, said amidase domain specifically cleaves a bond between a central N-acetlymuramoyl and an L-Alanine within a peptidoglycan layer. Preferably, said murimidase domain cleaves a bond between an N-acetylmuramine and a N-acetylglucosamine within a peptidoglycan layer. More preferably, said murimidase domain specifically cleaves a bond between an N-acetylmuramine and a N-acetylglucosamine within a peptidoglycan layer. Preferably, said glucosaminidase domain cleaves a bond between an N-acetlyglucosamine and an N-acetylmuramine within a peptidoglycan layer. More preferably, said glucosaminidase domain specifically cleaves a bond between an N-acetlyglucosamine and an N-acetylmuramine within a peptidoglycan layer. Preferably said peptidoglycan layer is of a bacterial cell, preferably a gram positive bacterial cell, more preferably of a *Staphylococcus*, most preferably of a *Staphylococcus Aureus*. Preferably, the cleavage of a bond by an enzymatic active domain as defined herein is specific if such a bond is hydrolysed at least 2, 5, 10, 50 or a 100 times more efficient with said enzymatic active domain as compared to the hydrolyses of any other bond as defined herein above with said enzymatic active domain.

Preferably, a CHAP domain encompassed within the present invention originates from *Staphylococcus* phage K, *Staphylococcus* phage Twort and/or *S. aureus* bacteriophage phi 11. Preferably, a CHAP domain encompassed within the present invention, is a domain that has at least 80, 81, 82, 83, 84, 85, 86, 87, 88, 89, 90, 91, 92, 93, 94, 95, 96, 97, 98, 99 or 100% identity with SEQ ID NO: 10, 12 or 98 and/or is preferably encoded by SEQ ID NO: 9 or 11. Preferably, an endopeptidase domain encompassed within the present invention originates from *S. aureus* bacteriophage Φ2638a and/or *S. simulans*. Preferably, an endopeptidase domain encompassed by the present invention has at least 80, 81, 82, 83, 84, 85, 86, 87, 88, 89, 90, 91, 92, 93, 94, 95, 96, 97, 98, 99 or 100% identity with SEQ ID NO: 14 or 16 and/or is preferably encoded by SEQ ID NO: 13 or 15. Preferably, an amidase domain encompassed within the present invention originates from *S. aureus* bacteriophage Φ2638a or *S. aureus* bacteriophage phi 11. Preferably an amidase domain of the present invention has at least 80, 81, 82, 83, 84, 85, 86, 87, 88, 89, 90, 91, 92, 93, 94, 95, 96, 97, 98, 99 or 100% identity with SEQ ID NO: 18 or 100 and/or is preferably encoded by SEQ ID NO: 17 or 99.

Preferably, the invention provides for a composition comprising a first and a second compound, wherein said first compound is an anti-inflammatory compound and said second compound is a compound specifically targeting a bacterial cell, preferably a gram positive bacterial cell, wherein said second compound is a naturally occurring or mutant bacteriophage, a naturally occurring endolysin or a mutant polypeptide.

A naturally occurring bacteriophage of the present invention may be any bacteriophage specifically targeting and infecting a bacterial cell, preferably bacterial cell, preferably a *Staphylococcus*, most preferably a *Staphylococcus aureus*. Preferably, a naturally occurring bacteriophage of the present invention is selected from, but not limited to, a group consisting of *S. aureus* bacteriophage Φ2638a, *S. aureus* bacteriophage Φ11, *S. aureus* bacteriophage ΦTwort, *S. haemolyticus* JCSC1435, *S. aureus* Phage K, *S. warneri* phage WMY, *S. aureus* phage NM3 and *S. aureus* 80alpha. Said naturally occurring endolysin may be synthesized and/ or purified. A bacteriophage according to the invention may be a mutant, chimeric and/or recombinant bacteriophage. The person skilled in the art may construct a bacteriophage of the present invention by placing mutations in the genome and/or deleting and/or inserting coding sequences or parts thereof into the genome using methods known in the art. A naturally occurring endolysin may be any wild type or native endolysin exhibiting peptidoglycan hydrolase activity. Preferred is a *Staphylococcus* phage endolysin, preferably said *Staphylococcus* phage endolysin is selected from, but not limited to, the group consisting of *S. aureus* bacteriophage Φ2638a endolysin, *S. aureus* bacteriophage Φ11 endolysin, *S. aureus* bacteriophage ΦTwort endolysin, *S. haemolyticus* JCSC1435, *S. aureus* Phage K endolysin, *S. warneri* phage WMY endolysin, *S. aureus* phage NM3 endolysin and *S. aureus* 80alpha endolysin. Also preferred is *S. simulans* lysostaphin and/or a homologue of *S. simulans* lysostaphin such as *S. capitis* ALE-1 enzyme. Most native *Staphylococcus* bacteriophage endolysins exhibiting peptidoglycan hydrolase activity consist of a C-terminal cell wall-binding domain (CBD), a central N-acetylmuramoyl-L-Alanine amidase domain, and an N-terminal Alanyl-glycyl endopeptidase domain with CHAP homology, or in case of Ply2638, of an N-terminal endopeptidase domain with Peptidase_M23 homology, the latter three domains exhibiting peptidoglycan hydrolase activity each with distinct target bond specificity and generally named herein as enzymatically active domains.

A mutant polypeptide as encompassed within the present invention may be a chemically synthesized polypeptide or a recombinant or retrofitted polypeptide produced in vitro. A retrofitted construct is defined herein as a polynucleotide comprising heterologous nucleotide sequences. As used herein the term heterologous sequence or heterologous polynucleotide is one that is not naturally found operably linked as neighboring sequence of said first nucleotide sequence. As used herein, the term heterologous may mean recombinant. Recombinant refers to a genetic entity distinct from that generally found in nature. As applied to a nucleotide sequence or nucleic acid molecule, this means that said nucleotide sequence or nucleic acid molecule is the product of various combinations of cloning, restriction and/or ligation steps, and other procedures that result in the production of a construct that is distinct from a sequence or molecule found in nature. Preferably, a mutant polypeptide to the present invention comprises at least an enzymatic active domain and a cell binding domain as defined herein.

An endolysin or mutant polypeptide of the present invention may be in a purified form or may be comprised within a crude composition, preferably of biological origin, such as a bacterial lysate, yeast lysate, fungal lysate, sonicate or fixate. Alternatively, said endolysin or mutant polypeptide may be a chemically synthesized endolysin or polypeptide or a recombinant polypeptide produced in vitro.

An endolysin or mutant polypeptide of the present invention preferably comprises or consists of at least one enzymatic active domain and at least one cell binding domain and optionally a tag for ease of purification. Preferably, said tag is selected from, but is not limited to, the group consisting of a FLAG-tag, poly(His)-tag, HA-tag and Myc-tag. More preferably said tag is a 6×His-tag. Even more preferably, said tag is an N-terminal 6×His-tag (indicated herein as HXa) identical to SEQ ID NO: 74 and preferably encoded by SEQ ID NO: 73).

Preferably, a cell wall-binding domain according to the present invention is located on the C-terminal side of the enzymatic active domain within said naturally occurring endolysin or a mutant polypeptide. Preferably, said mutant naturally occurring or mutant polypeptide comprises at least two or more enzymatic active domains with distinct target bond specificities as distinct target bond specificities confer synergistic effects. In an embodiment of the invention, a composition comprises at least two distinct compounds targeting a bacterial cell, preferably a gram positive bacterial cell, preferably a *Staphylococcus*, more preferably a *Staphylococcus aureus*. Preferably said at least two distinct compounds are naturally occurring endolysin, which are optionally synthesized. Preferably said at least two distinct compounds are recombinant polypeptides each comprising a distinct enzymatic active domain and/or a different multiplicity of at least two distinct enzymatic active domains as defined herein below.

Preferably, the invention provides for a composition comprising a first and a second compound, wherein said first compound is an anti-inflammatory compound and said second compound is a compound specifically targeting a bacterial cell, preferably a gram positive bacterial cell, wherein said second compound is a recombinant polypeptide comprising a multiplicity of said one or more enzymatic active domains exhibiting target bond specificity. "Multiplicity" is to be understood as a number of copies and may be any integer varying from 1 to 20, preferably from 1 to 10, more preferably from 1 to 3, most preferably said multiplicity is 2, i.e. a duplicate. Polypeptides comprising a multiplicity of enzymatic active domains show superior lytic activity as compared to polypeptides comprising a single enzymatic active domain.

Preferably, said second compound is a polypeptide comprising and/or consisting of an enzymatic active domain, a cell wall binding and optionally a tag for ease of purification as defined herein, preferably said enzymatic active domain being a cysteine, histidine-dependent amidohydrolases/peptidase domain, an endopeptidase domain or an amidase domain, and preferably polypeptide comprises a multiplicity of said enzymatic active domain, preferably said multiplicity being 2, i.e. a duplicate. More preferably said polypeptide comprises and/or consists of a duplicated amidase domain and a cell wall binding domain and optionally a tag for ease of purification as defined herein, preferably said amidase is from *S. aureus* bacteriophage Φ2638a endolysin and said cell wall binding domain is of *S. simulans* lysostaphin. Most preferably said polypeptide comprises and/or consists of a duplicated endopeptidase domain and a cell wall binding domain and optionally a tag for ease of purification as defined herein, preferably said endopeptidase domain is a Peptidase_M23 domain of *S. simulans* lysostaphin and said cell wall binding domain is of *S. simulans* lysostaphin.

Preferably, said second compound is a polypeptide has at least 80, 81, 82, 83, 84, 85, 86, 87, 88, 89, 90, 91, 92, 93, 94, 95, 96, 97, 98, 99 or 100% identity with SEQ ID NO: SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 76, 78, 80, 82, 84, 86, 88, 90, 92, 94, 98 or 100 and/or is encoded by a polynucleotide having at least 80, 81, 82, 83, 84, 85, 86, 87, 88, 89, 90, 91, 92, 93, 94, 95, 96, 97, 98, 99 or 100% identity to any of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 75, 77, 79, 81, 83, 85, 87, 89, 91, 93, 97 or 99. Preferably, said polypeptide has at least 80, 81, 82, 83, 84, 85, 86, 87, 88, 89, 90, 91, 92, 93, 94, 95, 96, 97, 98, 99 or 100% identity with SEQ ID NO: 28, 34, 46, 52, 58 or 70, more preferably, said polypeptide has at least 80, 81, 82, 83, 84, 85, 86, 87, 88, 89, 90, 91, 92, 93, 94, 95, 96, 97, 98, 99 or 100% identity with SEQ ID NO: 28, 46, 52, or 70, even more preferably, said polypeptide has at least 80, 81, 82, 83, 84, 85, 86, 87, 88, 89, 90, 91, 92, 93, 94, 95, 96, 97, 98, 99 or 100% identity with SEQ ID NO: 46 or 70, most preferably said polypeptide has at least 80, 81, 82, 83, 84, 85, 86, 87, 88, 89, 90, 91, 92, 93, 94, 95, 96, 97, 98, 99 or 100% identity with SEQ ID NO: 70.

Preferably, the invention provides for a composition comprising a first and a second compound, wherein said first compound is an anti-inflammatory compound and said second compound is a compound specifically targeting a bacterial cell, preferably a gram positive bacterial cell, wherein said first compound is selected from the group consisting of a corticosteroid, a calcineurin inhibitor, an immunotherapeutic compound, a recombinant human IFN-gamma, a microbial probiotic, a cytokine modulator, an inflammatory cell recruitment blocker, and a T cell activation inhibitor. Preferred calcineurin inhibitors are FK506, tacrolimus and pimecrolimus. A preferred immunotherapeutic compound is omalizumab, a humanized IgG1 monoclonal antibody against IgE that recognizes and masks an epitope in the CH3 region of IgE responsible for binding to the high-affinity FcεR on mast cells and basophils. Preferred cytokine modulators are a soluble IL-4 receptor, an anti-IL-5 monoclonal antibody and a TNF inhibitor. Preferred inflammatory cell recruitment blockers are a chemokine receptor antagonist and a CLA inhibitor. Preferred T cell activation inhibitors are alefacept and efalizumab. Corticosteroids that may be used include, but are not limited to, betamethasone dipropionate, fluocinolone acetonide, betamethasone valerate, triamcinolone acetonide, clobetasol propionate, desoximetasone, diflorasone diacetate, amcinonide, flurandrenolide, hydrocortisone valerate, hydrocortisone butyrate, desonide, hydrocortisone and methylprednisolone acetate. A further preferred anti-inflammatory compound is dapsone which has both antimicrobial and anti-inflammatory properties.

In all embodiments of the present invention, the second compound specifically targeting a bacterial cell, preferably a gram positive bacterial cell may be comprised of a combination of a source of a first enzymatic active domain and a source of a second enzymatic active domain, wherein said first and second enzymatic active domains exhibit distinct target bond specificities and are comprised on a distinct first and second polypeptide, i.e. said first enzymatic active domain is comprised on a first polypeptide and said second enzymatic domain is comprised on a second polypeptide, wherein said first and second polypeptide each have a distinct amino acid sequence. In addition, the second compound according to the present invention may be comprised of a combination of a source of a first enzymatic active domain, a source of a second enzymatic active domain and a source of a third enzymatic active domain, wherein said first, second and third enzymatic active domain exhibit distinct target bond specificities and are comprised on a distinct first, second and third polypeptide, i.e. said first enzymatic active domain is comprised on a first polypeptide, said second enzymatic domain is comprised on a second polypeptide, and said third enzymatic domain is comprised on a third polypeptide, wherein said first, second and third polypeptide each have a distinct amino acid sequence. Furthermore, the second compound according to the present invention may be comprised of a combination of a source of a first enzymatic active domain, a source of a second enzymatic active domain, a source of a third enzymatic active domain, and a source of a further enzymatic active domain, wherein said first, second, third and further enzymatic active domain exhibit distinct target bond specificities and are comprised on a distinct first, second, third and further polypeptide, i.e. said first enzymatic active domain is comprised on a first polypeptide, said second enzymatic domain is comprised on a second polypeptide, said third enzymatic domain is comprised on a third polypeptide, and said further enzymatic active domain is comprised on a further polypeptide, wherein said first, second, third and further polypeptide each have a distinct amino acid sequence. A further enzymatic active domain is meant herein as a fourth, fifth, sixth, seventh, eighth, ninth, tenth or more enzymatic active domain, preferably a fourth enzymatic active domain. A further polypeptide is meant herein as a fourth, fifth, sixth, seventh, eighth, ninth, tenth or more polypeptide, preferably a fourth polypeptide.

The inventors surprisingly found for the second compound according to the invention, that simultaneous application of two or more enzymatically active domains with distinct target bond specificities confers synergistic effects. Surprisingly, this works not only when enzymatically active domains with different specificities are located on the same molecule as in native *Staphylococcus* endolysins, but works also when the enzymatically active domains with different specificities are separated on distinct polypeptides.

The benefit of having distinct enzymatic active domains located on separate individual polypeptides is that the resulting polypeptides are smaller which can be more easily produced. Furthermore, these smaller polypeptides have better diffusion properties in specific environments and can be more resistant to degradation and feature higher thermostability. Another advantage is that independent distinct enzymatic active domains located on separate distinct polypeptide molecules can be mixed and pooled in variable compositions, at a ratio that is best suited to hydrolyse the specific bacterial target cells. The second compound according to the invention comprised of a combination as described herein can be supplemented and/or complemented by the use of virtually any functional enzymatic active domain with virtually any target bond specificity from many different origins including phage lysins, bacteriocins, autolysins, or any other cell wall lytic enzymes.

Within the context of the second compound according to the present invention 'a combination' means that a source of a first enzymatic active domain and a source of a second enzymatic active domain are contemplated and encompassed. In addition, within the context of the second compound according to present invention 'a combination' means that a source of a first enzymatic active domain, a source of a second enzymatic active domain and optionally a source of a third and/or further enzymatic active domain are contemplated and encompassed. Each source may be together or present together or combined together or physically in contact with the other source forming one single composition. Each source may alternatively be comprised within a distinct composition. However the present invention provides the insight that both sources of a first and a second enzymatic active domain are preferably needed or are used in order to get an effect of the present invention as defined herein. If each source is not present in a same single composition, each source and/or each distinct composition comprising a source of a combination encompassing the second compound according to the present invention may be used sequentially or simultaneously.

'A source of a first enzymatic active domain', 'a source of a second enzymatic active domain', 'a source of a third enzymatic active domain' and 'a source of a further enzymatic active domain' preferably comprises a protein-based source, i.e. a polypeptide, a protein, digest of a protein and/or fragment of a protein or digest, or a source not being protein based, i.e. a nucleic acid encoding a protein or derived peptide or protein fragment. Below we define preferred sources of a first enzymatic active domain, a source of a second enzymatic active domain, a source of a third enzymatic active domain and a source of a further enzymatic active domain that are encompassed by the invention. When the second compound according to the invention relates to a combination of a source of a first enzymatic active domain, a source of a second enzymatic active domain and optionally a source of a third and/or further enzymatic active domain, each of the sources of a first enzymatic active domain defined herein may be combined with each of the sources of a second and optionally third and/or further enzymatic active domain defined herein. It is also encompassed by the present invention to use a combination of a source of a first enzymatic active domain being protein-based with a source of a second and optionally a third and/or further enzymatic active domain being not protein-based, and vice versa.

'Comprised on distinct polypeptides' is meant herein as any of said first, second and optionally third and/or further enzymatic active domain is comprised on a polypeptide which is distinct from the polypeptide that any of the other of said first, second and optionally third and/or further enzymatic active domain is comprised on.

In all embodiments according to the invention, a polypeptide can be a natural polypeptide or an isolated polypeptide, preferably an isolated polypeptide. A nucleic acid according to the present invention may be a natural nucleic acid or an isolated nucleic acid, preferably an isolated nucleic acid. A nucleic acid construct according to the present invention can be a natural or an isolated construct, preferably an isolated nucleic acid construct.

Preferably, a first, a second and optionally a third and/or further enzymatic active domain together encompassing the second compound according to the present invention is a domain selected from the group consisting of a cysteine, histidine-dependent amidohydrolases/peptidase (CHAP) domain, an endopeptidase domain, and an amidase domain; all preferably as described previously herein.

Preferably, a first, second, third and/or further polypeptide together encompassing the second compound according to the present invention comprises a different multiplicity of a first, second, third and/or further enzymatic active domain according to the present invention. A "multiplicity" is herein defined as a number of copies. A "different multiplicity" is defined herein as a multiplicity or number of copies of a specific enzymatic active domain according to the invention, i.e. a first, second, third or further enzymatic active domain as defined herein, comprised within a specific polypeptide of the invention, i.e. a first, second, third or further polypeptide as defined herein, to be different form a multiplicity or number of copies of that same enzymatic active domain within another polypeptide of the combination encompassing the second compound of the invention. For example, a combination encompassing the second compound of the present invention comprises a first polypeptide comprising a specific number of copies of a first enzymatic active domain, and a second polypeptide comprising a different number of copies of said first enzymatic active domain. Furthermore, said first polypeptide of said exemplified combination encompassing the second compound of the present invention may further comprise a specific number of copies of second enzymatic active domain, which is different from the number of copies of said second enzymatic active domain as comprised on said second polypeptide of said combination. Furthermore, any further polypeptide of said exemplified combination encompassing the second compound of the present invention may comprise a number of copies of further enzymatic active domain, which is different from the number of copies of said further enzymatic active domain as comprised on said first and second polypeptide of said combination. Although a combination of distinct polypeptides each comprising a single distinct enzymatic active domain showed synergistic lytic activity as compared to the lytic activity of each separate polypeptide, it was surprisingly found by the present inventors that polypeptides comprising a multiplicity of enzymatic active domains show superior lytic activity as compared to polypeptides comprising a single enzymatic active domain.

Moreover, a combination of distinct enzymatic domains on distinct polypeptides wherein at least one of said distinct polypeptides comprises a multiplicity of enzymatic active domains was found superior over a combination wherein all said distinct polypeptides comprise a single distinct enzymatic active domain. Moreover, a combination encompassing the second compound according to the present invention, wherein a first, second, third and/or further polypeptide comprise a multiplicity of a first, second, third and/or further enzymatic active domain according to the present invention, respectively, was found superior over a combination encompassing the second compound according to the present invention, wherein said first, second, third and/or further polypeptide comprise a single copy of said first, second, third and/or further enzymatic active domain, respectively, and preferably wherein said multiplicity, as defined herein, is 2, i.e. a duplicate. In a preferred embodiment, the synergistic effect of a combination encompassing the second compound according to the present invention, wherein a first, second, third and/or further polypeptide according to the present invention comprise a multiplicity of a first, second, third and/or further enzymatic active domain according to the present invention, respectively, was found superior over a combination encompassing the second compound according to the present invention, wherein said first, second, third and further polypeptide comprise a single copy of said first, second, third and further enzymatic active domain, respectively, and preferably wherein said multiplicity, as defined herein below, is 2, i.e. a duplicate.

Preferably, a first and/or second polypeptide of a combination encompassing the second compound according to the present invention, comprises a different multiplicity of a first and/or second enzymatic active domain according to the present invention. Multiplicity of said first and second domain is defined as previously herein as a number of copies, preferably indicated by k, l, n and p, of said first and second domain indicated as follows:

k indicates the number of copies of said first enzymatic active domain on said first polypeptide;

l indicates the number of copies of said second enzymatic active domain on said first polypeptide;

n indicates the number of copies of said first enzymatic active domain on said second polypeptide;

p indicates the number of copies of said second enzymatic active domain on said second polypeptide;

and wherein k and p are independent integers from 1-10, 1-9, 1-8, 1-7, 1-6, 1-5, 1-4, 1-3, or preferably 1-2, and l and n are independent integers from 0-10, 0-9, 0-8, 0-7, 0-6, 0-5, 0-4, 0-3, or preferably 0-2, and wherein k is a different integer than n and/or l is a different integer than p, most preferably k and p are 2 and l and n are 0.

Preferably, a first, second and third polypeptide encompassing the second compound of the present invention comprise a different multiplicity of a first, second and third enzymatic active domain according to the present invention.

Multiplicity of said first, second and third domain is defined as previously herein as a number of copies, preferably indicated by k, l, m, n, p, q, r, s and t, of said first, second and third domain indicated as follows:

k indicates the number of copies of said first enzymatic active domain on said first polypeptide;

l indicates the number of copies of said second enzymatic active domain on said first polypeptide;

m indicates the number of copies of said third enzymatic active domain on said first polypeptide;

n indicates the number of copies of said first enzymatic active domain on said second polypeptide;

p indicates the number of copies of said second enzymatic active domain on said second polypeptide;

q indicates the number of copies of said third enzymatic active domain on said second polypeptide;

r indicates the number of copies of said first enzymatic active domain on said third polypeptide;

s indicates the number of copies of said second enzymatic active domain on said third polypeptide;

t indicates the number of copies of said third enzymatic active domain on said third polypeptide;

and wherein k, p and t are independent integers from 1-10, 1-9, 1-8, 1-7, 1-6, 1-5, 1-4, 1-3, or preferably 1-2, and l, m, n, q, r, and s are independent integers from 0-10, 0-9, 0-8, 0-7, 0-6, 0-5, 0-4, 0-3, or preferably 0-2, and wherein k is a different integer than n and/or r, and/or l is a different integer than p and/or s, and/or t is a different integer than m or q, most preferably k, p and t are 2 and l, m, n, q, r, and s are 0.

Preferably, a first, second, third and further polypeptide encompassing the second compound of the present invention comprise a different multiplicity of a first, second, third and further enzymatic active domain according to the present invention. Multiplicity of said further enzymatic active domain in view of said first, second and third enzymatic active domain is to be construed herein in an analogous manner as defined herein above for a first, second and third enzymatic active domain.

Preferably a first, second, third or further polypeptide encompassing the second compound according to the present invention has a length of at least 140, 150, 160, 170, 180, 190, 200, 210, 220, 230, 240, 250, 260, 270, 280, 290, 300, 310, 320 or 330 amino acids and/or a length of at most 850, 800, 750, 700, 650, 600, 550, 500, 490, 480, 470, 460, 450, 440, 430, 420, 410, 400, 390, 380 or 370 amino acids. More preferably, a first, second or third polypeptide encompassing the second compound according to the present invention has a length of 140-850, 140-800, 140-750, 140-700, 140-650, 140-600, 140-550 140-500, 140-490, 140-480, 140-470, 140-460, 140-450, 140-440, 140-430, 140-420, 140-410, 140-400, 140-390, 140-380, 140-370, 150-850, 160-850, 170-850, 180-850, 190-850, 200-850, 210-850, 220-850, 230-850, 240-850, 250-850, 260-850, 270-850, 280-850, 290-850, 300-850, 310-850, 320-850 or 330-850 amino acids.

Preferably a first and second polypeptide encompassing the second compound according to the present invention each have a length of at least 140, 150, 160, 170, 180, 190, 200, 210, 220, 230, 240, 250, 260, 270, 280, 290, 300, 310, 320 or 330 amino acids and/or a length of at most 800, 850, 700, 650, 600, 550, 500, 490, 480, 470, 460, 450, 440, 430, 420, 410, 400, 390, 380 or 370 amino acids. More preferably, a first and second polypeptide according to the present invention each have a length of 140-850, 140-800, 140-750, 140-700, 140-650, 140-600, 140-550 140-500, 140-490, 140-480, 140-470, 140-460, 140-450, 140-440, 140-430, 140-420, 140-410, 140-400, 140-390, 140-380, 140-370, 150-850, 160-850, 170-850, 180-850, 190-850, 200-850, 210-850, 220-850, 230-850, 240-850, 250-850, 260-850, 270-850, 280-850, 290-850, 300-850, 310-850, 320-850 or 330-850 amino acids.

Preferably a first, second and third polypeptide encompassing the second compound according to the present invention each have a length of at least 140, 150, 160, 170, 180, 190, 200, 210, 220, 230, 240, 250, 260, 270, 280, 290, 300, 310, 320 or 330 amino acids and/or a length of at most 800, 850, 700, 650, 600, 550, 500, 490, 480, 470, 460, 450, 440, 430, 420, 410, 400, 390, 380 or 370 amino acids. More preferably, a first, second and third polypeptides encompassing the second compound according to the present invention each have a length of 140-850, 140-800, 140-750, 140-700, 140-650, 140-600, 140-550 140-500, 140-490, 140-480, 140-470, 140-460, 140-450, 140-440, 140-430, 140-420, 140-410, 140-400, 140-390, 140-380, 140-370, 150-850, 160-850, 170-850, 180-850, 190-850, 200-850, 210-850, 220-850, 230-850, 240-850, 250-850, 260-850, 270-850, 280-850, 290-850, 300-850, 310-850, 320-850 or 330-850 amino acids.

Preferably a first, second, third and further polypeptide encompassing the second compound according to the present invention each have a length of at least 140, 150, 160, 170, 180, 190, 200, 210, 220, 230, 240, 250, 260, 270, 280, 290, 300, 310, 320 or 330 amino acids and/or a length of at most 800, 850, 700, 650, 600, 550, 500, 490, 480, 470, 460, 450, 440, 430, 420, 410, 400, 390, 380 or 370 amino acids. More preferably, a first, second, third and further polypeptides encompassing the second compound according to the present invention each have a length of 140-850, 140-800, 140-750, 140-700, 140-650, 140-600, 140-550 140-500, 140-490, 140-480, 140-470, 140-460, 140-450, 140-440, 140-430, 140-420, 140-410, 140-400, 140-390, 140-380, 140-370, 150-850, 160-850, 170-850, 180-850, 190-850, 200-850, 210-850, 220-850, 230-850, 240-850, 250-850, 260-850, 270-850, 280-850, 290-850, 300-850, 310-850, 320-850 or 330-850 amino acids.

An embodiment provides a combination of a source of a first and a second enzymatic active domain encompassing the second compound according to the present invention, wherein said first and second enzymatic active domains are comprised on distinct, first and second polypeptides of the present invention, wherein said first polypeptide is free of said second enzymatic active domain and said second polypeptide is free of said first enzymatic active domain. Moreover, provided is a combination according to the present invention, wherein l and n are 0.

Another embodiment provides a combination of a source of a first, second and third enzymatic active domain encompassing the second compound according to the present invention, wherein said first, second and third enzymatic active domains are comprised on distinct, first, second and third polypeptides, wherein said first polypeptide is free of said second and third enzymatic active domain, said second polypeptide is free of said first and third enzymatic active domain, and said third polypeptide is free of said first and second enzymatic active domain. Moreover, provided is a combination according to the present invention, wherein l, m, n, q, r and s are 0. Even more preferably, the present invention provides a combination encompassing the second compound according to the present invention, wherein l, m, n, q, r and s are 0 and k, p and t are 2.

Another embodiment provides a combination of a source of a first, second, third and further enzymatic active domain encompassing the second compound according to the present invention, wherein said first, second, third and further enzymatic active domains are comprised on a distinct, first, second, third and further polypeptide, respectively, wherein preferably said first polypeptide is free of said second, third and further enzymatic active domain;

preferably said second polypeptide is free of said first, third and further enzymatic active domain;

preferably said third polypeptide is free of said first, second and further enzymatic active domain; and, preferably said further polypeptide is free of said first, second and third enzymatic active domain.

Preferably said first, second, third and further enzymatic active domain are comprised within said first, second, third and further polypeptide, respectively, in duplicate, i.e. wherein the multiplicity as identified herein is 2. Also encompassed is a combination encompassing the second compound according to the present invention, wherein a first, second and/or third polypeptide according to the present invention are not free of a first, second and/or third enzymatic active domain according to the present invention, but said first, second and/or third polypeptide differ in multiplicity of said first, second and/or third enzymatic active domain. Moreover, encompassed is a combination encompassing the second compound according to the present invention, wherein at least one of k, l, m, n p, q, r, s or t is 2 and wherein any of the other k, l, m, n p, q, r, s and/or t is 1 or 0.

Preferred is a combination encompassing the second compound according to the present invention, wherein a first, second, third and/or further polypeptide is a polypeptide that has at least 80, 81, 82, 83, 84, 85, 86, 87, 88, 89, 90, 91, 92, 93, 94, 95, 96, 97, 98, 99 or 100% identity with a polypeptide selected from the group consisting of SEQ ID NO: 26, 28, 30, 32, 34, 36, 38, 40, 42, 44, 46, 48, 50, 52, 54, 56, 58, 60, 62, 64, 66, 68, 70, 72, 76, 78, 80, 82, 84, 86, 88, 90, 92, 94, 98 or 100.

Within the context of the present invention, several preferred, non-limiting, combinations encompassing the second compound according to the invention are envisaged, which are listed here below.

Preferred is a combination of a source of first enzymatic active domain and a second enzymatic active domain, wherein said first and second enzymatic active domains are comprised on distinct first and second polypeptides, and wherein said first enzymatic active domain is a cysteine, histidine-dependent amidohydrolases/peptidase domain and said second enzymatic active domain is an endopeptidase domain or wherein said first enzymatic active domain is a cysteine, histidine-dependent amidohydrolases/peptidase domain and said second enzymatic active domain is amidase domain or wherein said first enzymatic active domain is an endopeptidase domain and said second enzymatic active domain is amidase domain, wherein said distinct first and second each further comprises a cell wall-binding domain, and wherein each of said distinct first and second polypeptides comprises a multiplicity of said first or second enzymatic active domain, preferably said multiplicity being 2, i.e. a duplicate.

Also preferred is a combination of a source of first and second enzymatic active domain, wherein said first and second enzymatic active domains are comprised on distinct first and second polypeptides, and wherein said first enzymatic domain is histidine-dependent amidohydrolases/peptidase domain and said second enzymatic active domain is an endopeptidase domain or said first enzymatic active domain is a cysteine, histidine-dependent amidohydrolases/peptidase domain and said second enzymatic active domain is amidase domain or said first enzymatic active domain is an endopeptidase domain and said second enzymatic active domain is amidase domain, and wherein said first and second polypeptide each further comprise a cell wall binding domain.

Also preferred is a combination of a source of first enzymatic active domain and a second enzymatic active domain, wherein said first and second enzymatic active domains are comprised on distinct first and second polypeptides, and wherein said first enzymatic active domain is a cysteine, histidine-dependent amidohydrolases/peptidase domain and said second enzymatic active domain is an endopeptidase domain, and wherein said combination further comprises a source of a third enzymatic active domain comprised on a distinct third polypeptide, wherein said third enzymatic active domain is an amidase domain and said distinct first, second and third polypeptide each further comprises a cell wall-binding domain, and wherein each of said distinct first, second and third polypeptides comprises a multiplicity of said first, second or third enzymatic active domain, preferably said multiplicity being 2, i.e. a duplicate.

Also preferred is a combination of a source of first, second and third enzymatic active domain, wherein said first, second and third enzymatic active domains are comprised on distinct first, second and third polypeptides, and wherein said first enzymatic domain is histidine-dependent amidohydrolases/peptidase domain, said second enzymatic active domain is an endopeptidase domain and said third enzymatic active domain is an amidase domain, and wherein said first, second and third polypeptide each further comprise a cell wall binding domain.

Also preferred is a combination wherein, a first enzymatic active domain according to the present invention has at least 80, 81, 82, 83, 84, 85, 86, 87, 88, 89, 90, 91, 92, 93, 94, 95, 96, 97, 98, 99 or 100% identity with SEQ ID NO: 10 and a second enzymatic active domain according to the present invention as at least 80, 81, 82, 83, 84, 85, 86, 87, 88, 89, 90, 91, 92, 93, 94, 95, 96, 97, 98, 99 or 100% identity with SEQ ID NO: 16.

Also preferred is a combination wherein, a first enzymatic active domain according to the present invention has at least 80, 81, 82, 83, 84, 85, 86, 87, 88, 89, 90, 91, 92, 93, 94, 95, 96, 97, 98, 99 or 100% identity with SEQ ID NO: 10 and a second enzymatic active domain according to the present invention as at least 80, 81, 82, 83, 84, 85, 86, 87, 88, 89, 90, 91, 92, 93, 94, 95, 96, 97, 98, 99 or 100% identity with SEQ ID NO: 18.

Also preferred is a combination wherein, a first enzymatic active domain according to the present invention has at least 80, 81, 82, 83, 84, 85, 86, 87, 88, 89, 90, 91, 92, 93, 94, 95, 96, 97, 98, 99 or 100% identity with SEQ ID NO: 16 and a second enzymatic active domain according to the present invention as at least 80, 81, 82, 83, 84, 85, 86, 87, 88, 89, 90, 91, 92, 93, 94, 95, 96, 97, 98, 99 or 100% identity with SEQ ID NO: 18.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 34 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 46.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 34 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 46 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 70.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 52.

More preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 70 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 46.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 70 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 34.

More preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 70 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 52 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 34.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 52 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 46.

Also preferred is a combination wherein, a first enzymatic active domain according to the present invention has at least 80, 81, 82, 83, 84, 85, 86, 87, 88, 89, 90, 91, 92, 93, 94, 95, 96, 97, 98, 99 or 100% identity with SEQ ID NO: 10, a second enzymatic active domain according to the present invention as at least 80, 81, 82, 83, 84, 85, 86, 87, 88, 89, 90, 91, 92, 93, 94, 95, 96, 97, 98, 99 or 100% identity with SEQ ID NO: 16 and a third enzymatic active domain according to the present invention has at least 80, 81, 82, 83, 84, 85, 86, 87, 88, 89, 90, 91, 92, 93, 94, 95, 96, 97, 98, 99 or 100% identity with SEQ ID NO: 18.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 34, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 46 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 32, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 44 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 26.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 34, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 46 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 26.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 36, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 48 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 30.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 32, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 46 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 26.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 34, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 44 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 26.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 32, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 44 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 32, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 46 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 34, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 44 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 70 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 70 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 50.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 56, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 68 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 50.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 60, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 72 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 54.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 56, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 70 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 50.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 68 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 50.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 56, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 68 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 65, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 70 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 68 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 70 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 34, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 70 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 46 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 34, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 46 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 46 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination wherein, a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 34, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 70 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 28.

It is to be understood that a combination as described herein encompassing the second compound according to the present invention includes mixtures of a source of a first, a source of a second and optionally a source of a third and/or further enzymatic active domain according to in varying ratios. Preferably, such combination comprises a source a first and a source a second enzymatic active domain according to the present invention, wherein said first and second enzymatic active domain are present in equimolar amounts. Also preferred is a combination comprising a source a first, a source a second and a source a third enzymatic active domain according to the present invention, wherein said first, second and third enzymatic active domain are present in equimolar amounts. Also preferred is a combination comprising a source of a first, a source of a second, a source of a third and a source of a further enzymatic active domain according to the present invention, wherein said first, second, third and further enzymatic active domain are present in equimolar amounts.

In a second aspect, the invention provides for a kit of parts comprising:

a) a first vial containing a first composition comprising a first compound as defined in the first aspect of the invention; and, b) a second vial containing a second composition comprising a second compound as defined in the first aspect of the invention; and optionally, c) instructions for use, preferably comprising a dosage regime.

Preferably, said kit of parts, more specifically said first and second composition of said kit of parts, is for use as a medicament, preferably for use in the treatment of eczema, more preferably for use in the treatment of atopic dermatitis, as further detailed herein. A dosage regime is to be understood herein as an instruction for administration to an individual in the need thereof, preferably an instruction indicating an administration route, administration frequency and administration dosage, and optionally an instruction for admixing said first and second compound just before administration, as required for treatment, preferably required for treatment of eczema, more preferably for treatment of atopic dermatitis. Preferred administration routes, frequencies and dosages are further detailed herein. In an embodiment, said first composition according to a second aspect and/or said second composition according to a second aspect of the present invention is administered separately, preferably as part of an overall treatment regimen. In an alternative embodiment, said first composition according to a second aspect and said second composition according to a second aspect of the present invention are stored separately, and admixed just before administration. Preferably, "just before" is to be understood herein as less than 120, 60, 30, 15, 5, 4, 3, 2 or 1 minutes before administration, preferably less than 5 minutes before administration.

Said first and said second vial may be any vial, bottle, tube, ampoule, container, flask or the like, suitable for storing said first and second composition as defined herein, respectively. Preferably said first and/or second vial has a volume of between 0.1 and 500 mL, preferably between 1 and 100 mL, more preferably of about 5, 10, 50 or 100 mL.

In a third aspect, the invention provides for a method of treatment comprising the administration of a composition according to the first aspect of the invention and/or the sequential or simultaneous administration of a first and second compound of a kit of parts according to the second aspect of the invention.

Preferably, said method of treatment is a method for preventing, delaying and/or curing an infectious disease, such as, but not limited to, a skin infection, mastitis, pneumonia, meningitis, endocarditis, Toxic Shock Syndrome (TSS), sepsis, septicemia, bacteremia, or osteomyelitis. Preferably, said skin infection is selected from the group of acne, rosacea, pimples, impetigo, boils, furuncles, cellulitis folliculitis, psoriasis, carbuncles, scaled skin syndrome and abscesses. Preferably, said method of treatment is a method for preventing, delaying and/or curing eczema such as atopic dermatitis, allergic contact eczema, contact eczema, dyshidrotic eczema, neurodermatitis, nummular eczema, seborrheic eczema, stasis dermatitis, preferably atopic dermatitis. Preferably, said method of treatment is topical treatment of a skin infection and/or eczema as identified herein, more preferably atopic dermatitis.

Encompassed in the present invention is a composition according to the first aspect of the invention and/or a kit of parts according to second aspect of the invention, for use as a medicament. Preferably, said composition according to the first aspect of the invention and/or said kit of parts according to second aspect of the invention is for preventing, delaying and/or curing an infectious disease, such as, but not limited to, a skin infection, mastitis, pneumonia, meningitis, endocarditis, Toxic Shock Syndrome (TSS), sepsis, septicemia, bacteremia, or osteomyelitis. Preferably, said skin infection is selected from the group of acne, rosacea, pimples, impetigo, boils, furuncles, cellulitis, folliculitis, psoriasis, carbuncles, scaled skin syndrome and abscesses. Preferably, said composition according to the first aspect of the invention and/or said kit of parts according to the second aspect of the invention is for use preventing, delaying and/or curing of eczema such as atopic dermatitis, allergic contact eczema, contact exzema, dyshidrotic eczema, neurodermatitis, nummular eczema, seborrheic eczema, stasis dermatitis, preferably atopic dermatitis.

Also encompassed in the present invention is the use of a composition according to the first aspect of the invention and/or a kit of parts according to second aspect of the invention for the manufacture of a medicament. Preferably, said medicament is for preventing, delaying and/or curing an infectious disease, such as, but not limited to, a skin infection, mastitis, pneumonia, meningitis, endocarditis, Toxic Shock Syndrome (TSS), sepsis, septicemia, bacteremia, or osteomyelitis. Preferably, said skin infection is selected from the group of acne, rosacea, pimples, impetigo, boils, furuncles, cellulitis, folliculitis, psoriasis, carbuncles, scaled skin syndrome and abscesses. Preferably, said medicament is a medicament for preventing, delaying and/or curing eczema such as atopic dermatitis, allergic contact eczema, contact eczema, dyshidrotic eczema, neurodermatitis, nummular eczema, seborrheic eczema, stasis dermatitis, preferably atopic dermatitis.

Preferably, said composition according to the first aspect, a first composition of a kit of parts according to the second aspect and/or a second composition of a kit of parts according to the second aspect and/or medicament as defined herein is a topical formulation understood herein as a formulation, including a microencapsulated formulation, being suitable for topical administration and may be in the form of a cream, ointment, solution, powder, spray, aerosol, capsule, solid or gel, and/or may be bonded to a solid surface, e.g. by immobilization with affinity ligands or through ionic/hydrophobic interactions and covalent immobilization.

A composition according to the first aspect of the invention and/or a first and/or second composition of a kit of parts according to the second aspect of the invention may also form part of a body wash, soap, application stick or cosmetic.

A composition according to the first aspect and/or a second composition of a kit of parts according to the second aspect and/or a mixture resulting from admixing said first and second composition of a kit of parts according to the second aspect just before administration as earlier indicated herein, is preferably said to be active, functional or therapeutically active when it decreases the amount of bacterial cells, preferably gram positive bacterial cells, more preferably the amount of *Staphylococcus* bacterial cells, most preferably the amount of *Staphylococcus aureus* bacterial cells, present in a patient or in a cell of said patient or in a cell line or in a cell free in vitro system and preferably means that 99%, 90%, 80%, 70%, 60%, 50%, 40%, 30%, 20%, 10%, 5% or less of the initial amount of said bacterial cells is still detectable. More preferably, no bacterial cell, preferably no gram positive bacterial cell, more preferably no *Staphylococcus* bacterial cell, most preferably no *Staphylococcus aureus* bacterial cell, is detectable. In this paragraph, the expression "amount of bacterial cells" preferably means viable bacterial cells. Staphylococci of all genera may be detected using standard techniques known by the artisan such as immunohistochemical techniques using *Staphylococcus* specific antibodies, tube coagulase tests that detect staphylocoagulase or "free coagulase", detection of surface proteins such as clumping factor (slide coagulase test) and/or protein A (commercial latex tests). Viable Staphylococci may be detected using standard techniques known by the artisan such as microbiological bacterial culture techniques and/or real-time quantitative reverse transcription polymerase chain reaction to assay for bacterial mRNA. A decrease in amount of bacterial cells according to the present invention is preferably assessed in a tissue or in a cell of an individual or a patient by comparison to the amount present in said individual or patient before treatment with said composition or polypeptide of the invention. Alternatively, the comparison can be made with a tissue or cell of said individual or patient which has not yet been treated with said composition or polypeptide in case the treatment is local.

Preferably a composition according to the first aspect of the invention and/or a second composition of a kit of parts of the second aspect of the invention, and/or a resulting mixture resulting from admixing the first and second composition of the kit of part of the second aspect of the invention just before administration as identified herein before comprises an amount of a second compound as defined herein which is therapeutically active as earlier identified herein. Preferably, said composition is for topic administration to an individual in the need thereof, preferably to a patient suffering from eczema, and comprises said second compound in an effective amount, preferably a concentration of 0.001-10% by weight of the total composition. Depending on the specific activity of the second compound, the effective amount may be as low about a few micrograms/ml such as about 1, 2, 3, 4, 5, 6, 7, 8, 9, 10 microgram/ml to about several milligrams/ml such as about 1, 2, 3, 4, 5, 6, 7, 8, 9, 10 milligram/ml Preferably a composition according to the first aspect of the invention and/or a first composition of a kit of parts of the second aspect of the invention, and/or a resulting mixture resulting from admixing the first and second composition of the kit of part of the second aspect of the invention just before administration as identified herein before is a composition for topic application for the treatment of eczema comprising an anti-inflammatory compound, selected from, but not limited to, a corticosteroid a calcineurin inhibitor, an immunotherapeutic compound, a recombinant human IFN-gamma, a microbial probiotic, a cytokine modulator, an inflammatory cell recruitment blocker, a T cell activation inhibitor, or a combination of these. Preferably, said composition is for topic administration to an individual in the need thereof, preferably to a patient suffering from eczema, and comprises said anti-inflammatory compound compound in an effective amount, preferably in the range of 0.01 to 10% by weight of the total composition, preferably in the range of 0.05 to 5%, more preferably in a range of 0.05 to 2.5%, even more preferably in a range of 0.1 to 1%.

Preferably a composition according to the first aspect of the invention and/or a first composition of a kit of parts of the second aspect of the invention, and/or a resulting mixture resulting from admixing the first and second composition of the kit of part of the second aspect of the invention just before administration as identified herein before is a composition for topic application for the treatment of eczema comprising a corticosteroid in the range of 0.05 to 5%, by weight of the total composition preferably in a range of 0.05 to 2.5% more preferably in a range of 0.1 to 1%, even more preferably comprising about 0.05% clobetasol propionate, about 0.05% halobetasol propionate, about 0.1% fluocinonide, about 0.05% diflorasone diacetate, about 0.1% mometasone furoate, about 0.1% halcinonide, about 0.25% desoximetasone, about 0.05% fluocinonide, about 0.05% desoximetasone, about 0.1% clocortolone pivalate, about 0.1% mometasone furoate, about 0.1% triamcinolone acetonide, about 0.1% betamethasone valerate, about 0.025% fluocinolone acetonide, about 0.05% fluticasone propionate, about 0.1% prednicarbate, about 0.1% hydrocortisone probutate, about 0.1% triamcinolone acetonide, about 0.05% alclometasone dipropionate, about 0.05% desonide, about 0.025% triamcinolone acetonide, about 0.1% hydrocortisone butyrate, about 0.01% fluocinolone acetonide, about 1% hydrocortisone acetate, about 2% hydrocortisone, about 2.5% hydrocortisone and/or 0.5-1% hydrocortisone. About is defined herein as a value minus or plus 10% of the indicated value.

A composition according to the first aspect, a first composition of a kit of parts according to the second aspect and/or a second composition of a kit of parts according to the second aspect and/or medicament as defined herein may be in the liquid, solid or semi-liquid or semi-solid form, preferably further comprising a pharmaceutical acceptable carrier, excipient and/or stabilizer. Examples of pharmaceutically acceptable carriers, excipients and stabilizers include, but are not limited to, buffers such as phosphate, citrate, and other organic acids; antioxidants including ascorbic acid; low molecular weight polypeptides; proteins, such as serum albumin and gelatin; hydrophilic polymers such as polyvinylpyrrolidone; amino acids such as glycine, glutamine, asparagine, arginine or lysine; monosaccharides, disaccharides, and other carbohydrates including glucose mannose, or dextrins; chelating agents such as EDTA; sugar alcohols such as mannitol or sorbitol; salt-forming counterions such as sodium; and/or nonionic surfactants such as polysorbate (TWEEN™), polyethylene glycol (PEG), and poloxamers (PLURONICS™); and polymer thickeners such as hydrophilic and hydroalcoholic gelling agents frequently used in the cosmetic and pharmaceutical industries, preferably a gelling agent comprises between about 0.2% and about 4% by weight composition. A composition according to the first aspect, a first composition of a kit of parts according to the second aspect and/or a second composition of a kit of parts according to the second aspect and/or medicament as defined herein can also include a lubricant, a wetting agent, a sweetener, a flavoring agent, an emulsifier, a suspending agent, a sun screen such as, but not limited to, titanium dioxide or methyl cinnamate, and/or a preservative, in addition to the above ingredients, preferably a preservative is present as about 0.05% to 0.5% by weight of the total composition. A composition according to the first aspect, a first composition of a kit of parts according to the second aspect and/or a second composition of a kit of parts according to the second aspect and/or medicament as defined herein can also include a carrier which are known in the art (such as a carbohydrate and a sugar-alcohol) to aid in the exposure of the skin to a medicament.

Preferably, a composition according to the first aspect, a first composition of a kit of parts according to the second aspect and/or a second composition of a kit of parts according to the second aspect and/or a medicament as defined herein further comprises and additional active ingredient. An additional active ingredient may be any of, but is not limited to, an anti-inflammatory agent; a standard or conventional antibiotic agent such as, but not limited to penicillin, synthetic penicillins, bacitracin, methicillin, cephalosporin, polymyxin, cefaclor, Cefadroxil, cefamandole nafate, cefazolin, cefixime, cefmetazole, cefonioid, cefoperazone, ceforanide, cefotanme, cefotaxime, cefotetan, cefoxitin, cefpodoxime proxetil, ceftazidime, ceftizoxime, ceftriaxone, cefriaxone moxalactam, cefuroxime, cephalexin, cephalosporin C, cephalosporin C sodium salt, cephalothin, cephalothin sodium salt, cephapirin, cephradine, cefuroximeaxetil, dihydratecephalothin, moxalactam, loracarbef mafate and/or chelating agents; an antifungal, such as, but not limited to, oxiconazole nitrate, ciclopirox olamine, ketoconazole, miconazole nitrate and butoconazole nitrate; an anti-androgen, such as, but not limited to, flutamide and/or finasterid; a local anesthetic agent, such as, but not limited to tetracaine, tetracaine hydrochloride, lidocaine, lidocaine hydrochloride, dyclonine, dyclonine hydrochloride, dimethisoquin hydrochloride, dibucaine, dibucaine hydrochloride, butambenpicrate and/or pramoxine hydrochloride; and dapsone which has both antimicrobial and anti-inflammatory properties. Preferred weight percentages of antimicrobial agents are 0.1% to 10% weight of the total composition. Preferred weight percentages for local anesthetics are 0.025% to 5% by weight of the total composition.

A composition according to the first aspect, a first composition according to a second aspect and/or a second composition according to a second aspect and/or medicament as defined herein can be used to treat animals, including humans, suffering from any of the an infectious diseases and/or eczema as identified herein above, preferably from atopic dermatitis.

A preferred route of administration of said composition and/or said medicament is any suitable route of administration that can be used to administer said composition according to the first aspect, said first composition according to a second aspect and/or said second composition according to a second aspect and/or medicament as defined herein including but not limited to: oral, aerosol or other device for delivery to the lungs, nasal spray, intravenous, intramuscular, intraperitoneal, intrathecal, vaginal, rectal, topical, lumbar puncture, intrathecal, and direct application to the brain and/or meninges. Preferably, said composition according to the first aspect, said first composition according to a second aspect and/or said second composition according to a second aspect and/or medicament as defined herein are administered topical, preferably at the side of infection and/or lesion and/or, in the case of eczema, preferably at the side of skin rash.

A preferred administration frequency of said composition and/or said medicament is once or twice a day, preferably to the area of the skin affected by the disease or the side of lesion known in the art as the side of rash. Preferably said treatment is continued as long as required for the rash to be cleared. Preferably said treatment is continued for 2 to 3 days, for 7 to 10 days and/or for 2 to 3 weeks. Preferably a total amount of composition for topic application is administered as identified herein resulting in a total application of about 1 gram of corticosteroid to the person in the need thereof.

A preferred dosage of administration of said composition and/or said medicament is a dosage containing an effective total amount of said first and second compound resulting in the prevention, delay and/or cure of an infectious disease and/or eczema as earlier identified herein, preferably eczema, more preferably atopic dermatitis.

Definitions

"Sequence identity" or "identity" in the context of amino acid- or nucleic acid-sequence is herein defined as a relationship between two or more amino acid (peptide, polypeptide, or protein) sequences or two or more nucleic acid (nucleotide, polynucleotide) sequences, as determined by comparing the sequences. In the art, "identity" also means the degree of sequence relatedness between amino acid or nucleotide sequences, as the case may be, as determined by the match between strings of such sequences. Within the present invention, sequence identity with a particular sequence preferably means sequence identity over the entire length of said particular polypeptide or polynucleotide sequence. The sequence information as provided herein should not be so narrowly construed as to require inclusion of erroneously identified bases. The skilled person is capable of identifying such erroneously identified bases and knows how to correct for such errors.

"Similarity" between two amino acid sequences is determined by comparing the amino acid sequence and its conserved amino acid substitutes of one peptide or polypeptide to the sequence of a second peptide or polypeptide. In a preferred embodiment, identity or similarity is calculated over the whole SEQ ID NO as identified herein. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

A polynucleotide is represented by a nucleotide sequence. A polypeptide is represented by an amino acid sequence. A nucleic acid construct is defined as a polynucleotide which is isolated from a naturally occurring gene or which has been modified to contain segments of polynucleotides which are combined or juxtaposed in a manner which would not otherwise exist in nature. Optionally, a polynucleotide present in a nucleic acid construct is operably linked to one or more control sequences, which direct the production or expression of said peptide or polypeptide in a cell or in a subject.

As used herein the term "heterologous sequence" or "heterologous nucleic acid" is one that is not naturally found operably linked as neighboring sequence of said first nucleotide sequence. As used herein, the term "heterologous" may mean "recombinant". "Recombinant" refers to a genetic entity distinct from that generally found in nature. As applied to a nucleotide sequence or nucleic acid molecule, this means that said nucleotide sequence or nucleic acid molecule is the product of various combinations of cloning, restriction and/or ligation steps, and other procedures that result in the production of a construct that is distinct from a sequence or molecule found in nature.

"Operably linked" is defined herein as a configuration in which a control sequence is appropriately placed at a position relative to the nucleotide sequence coding for the polypeptide of the invention such that the control sequence directs the production/expression of the peptide or polypeptide of the invention in a cell and/or in a subject.

"Operably linked" may also be used for defining a configuration in which a sequence is appropriately placed at a position relative to another sequence coding for a functional domain such that a chimeric polypeptide is encoded in a cell and/or in a subject.

Expression will be understood to include any step involved in the production of the peptide or polypeptide including, but not limited to, transcription, post-transcriptional modification, translation, post-translational modification and secretion.

Optionally, a promoter represented by a nucleotide sequence present in a nucleic acid construct is operably linked to another nucleotide sequence encoding a peptide or polypeptide as identified herein.

The term "transformation" refers to a permanent or transient genetic change induced in a cell following the incorporation of new DNA (i.e. DNA exogenous to the cell). When the cell is a bacterial cell, as is intended in the current invention, the term usually refers to an extrachromosomal, self-replicating vector which harbors a selectable antibiotic resistance.

An expression vector may be any vector which can be conveniently subjected to recombinant DNA procedures and can bring about the expression of a nucleotide sequence encoding a polypeptide of the invention in a cell and/or in a subject. As used herein, the term "promoter" refers to a nucleic acid fragment that functions to control the transcription of one or more genes or nucleic acids, located upstream with respect to the direction of transcription of the transcription initiation site of the gene. It is related to the binding site identified by the presence of a binding site for DNA-dependent RNA polymerase, transcription initiation sites, and any other DNA sequences, including, but not limited to, transcription factor binding sites, repressor and activator protein binding sites, and any other sequences of nucleotides known to one skilled in the art to act directly or indirectly to regulate the amount of transcription from the promoter. Within the context of the invention, a promoter preferably ends at nucleotide −1 of the transcription start site (TSS).

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

The term "control sequences" is defined herein to include all components, which are necessary or advantageous for the expression of a polypeptide. Each control sequence may be native or foreign to the nucleic acid sequence encoding the polypeptide. Such control sequences include, but are not limited to, a leader, optimal translation initiation sequences (as described in Kozak, 1991, J. Biol. Chem. 266:19867-19870), a polyadenylation sequence, a pro-peptide sequence, a pre-pro-peptide sequence, a promoter, a signal sequence, and a transcription terminator. At a minimum, the control sequences include a promoter, and transcriptional and translational stop signals.

The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence, which is recognized by a host cell for expression of the nucleic acid sequence. The promoter sequence contains transcriptional control sequences, which mediate the expression of the polypeptide. The promoter may be any nucleic acid sequence, which shows transcriptional activity in the cell including mutant, truncated, and hybrid promoters, and may be obtained from genes encoding extracellular or intracellular polypeptides either homologous or heterologous to the cell.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator, which is functional in the cell, may be used in the present invention.

The control sequence may also be a suitable leader sequence, a non-translated region of a mRNA which is important for translation by the host cell. The leader sequence is operably linked to the 5' terminus of the nucleic acid sequence encoding the polypeptide. Any leader sequence, which is functional in the cell, may be used in the present invention.

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence, which is functional in the cell, may be used in the present invention.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a product or a composition or a nucleic acid molecule or a peptide or polypeptide of a nucleic acid construct or vector or cell as defined herein may comprise additional component(s) than the ones specifically identified; said additional component(s) not altering the unique characteristic of the invention. In addition, reference to an element by the indefinite article "a" or "an" does not exclude the possibility that more than one of the elements is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

Examples

Use of Corticosteroids and a Compound Specifically Targeting *S. aureus* (Staphefekt™)

In several forms of dermatitis, courses of topical corticosteroid therapy are used to suppress symptoms of local inflammation. However, corticosteroids do not treat the underlying cause of the inflammation, and symptoms are known to return eventually. It was hypothesized that a second compound according to the present invention would be effective in combination with corticosteroid treatment. As a second compound according to the invention, a compound specifically targeting *S. aureus* was used. The compound Staphefekt™ (Gladskin™) was obtained from Micreos Human Health B.V., The Netherlands. Since Staphefekt™ eradicates *S. aureus* as an etiological factor of local inflammation, it was speculated that during Staphefekt™ treatment less corticosteroids would be needed to alleviate symptoms. To study the use of corticosteroid during Staphefekt™ treatment, corticosteroid use and symptom relief was monitored in eight patients, of whom the treatment of several kinds of dermatitis with Staphefekt™ was guided and observed by a physician (table 1). In the six cases where *S. aureus* was found, symptoms diminished during treatment with Staphefekt™, and patients reported less need of corticosteroids anamnestically. In one patient with severe constitutional eczema, the burden of *S. aureus* carriership was high and symptoms diminished only moderately with Staphefek™, necessitating the unchanged use of corticosteroids and eventually even immune suppression with Neoral. In one case where no *S. aureus* was found, Staphefekt™ had no effect on symptoms and corticosteroid use remained unchanged.

The use of corticosteroids was not completely abandoned in the successfully treated patients, especially with the recurrence of symptoms after ceasing Staphefekt™ use. This suggests that a quick relief of symptoms at the stage of local inflammation is best achieved by combining symptomatic corticosteroid therapy with eradication of etiological *S. aureus* carriership by Staphefekt™.

The reduced need for corticosteroids as observed in customer feedback, questionnaires and the present physician guided Staphefekt™ study clearly indicates that a lower dose or shorter course of corticosteroids would be effective in combination therapy with a second compound according to the present invention, in casu Staphefekt™.

TABLE 1

Physician guided Staphefekt ™ cases.

| gender (age) | treatment indication | site | *S. aureus* carriership | relief of symptoms | corticosteroid use during treatment |
|---|---|---|---|---|---|
| male (22) | eczema | neck/face | +++ | moderate | unchanged corticosteroid use, Neoral because of relapse |
| male (32) | eczema | face | − | yes | less need |
| female (16) | eczema | arm, knee | + | yes | no need |
| female (19) | peri-oral dermatitis | peri-oral | + | yes | less need until relapse |
| female (16) | eczema | arm | − | no | unchanged |
| male (28) | contact dermatitis | hands | +++ | yes | less need |
| male (57) | contact dermatitis | hands | + | yes | no need |
| female (30) | eczema | arm | + | yes | less need |

TABLE 2

SEQ ID NO overview table

| SEQ ID NO | Name construct | organism |
|---|---|---|
| 1 | Ply2638 endolysin CDS | Bacteriophage 2638A |
| 2 | Ply2638 endolysin PRT | Bacteriophage 2638A |
| 3 | CWT-LST CDS | *S. simulans* |
| 4 | CWT-LST PRT | *S. simulans* |
| 5 | CBD2638 CDS | Bacteriophage 2638A |
| 6 | CBD2638 PRT | Bacteriophage 2638A |
| 7 | CWT-NM3 CDS | S. aureus phage phiNM3 |
|  | CWT-NM3 PRT | S. aureus phage phiNM3 |
| 9 | CHAPK CDS | *S. phage K* |
| 10 | CHAPK PRT | *S. phage K* |
| 11 | CHAP-ϕTwort CDS | *S. phage* Twort |
| 12 | CHAP-ϕTwort PRT | *S. phage* Twort |
| 13 | M23-2638 CDS | Bacteriophage 2638A |
| 14 | M23-2638 PRT | Bacteriophage 2638A |
| 15 | M23-LST CDS | *S. simulans* |
| 16 | M23-LST PRT | *S. simulans* |
| 17 | Ami2638 CDS | Bacteriophage 2638A |
| 18 | Ami2638 PRT | Bacteriophage 2638A |
| 19 | CHAPK_CHAPK_CWT-LST CDS | artificial construct |
| 20 | CHAPK_CHAPK_CWT-LST PRT | artificial construct |
| 21 | M23-LST_M23-LST_CWT-LST CDS | artificial construct |
| 22 | M23-LST_M23-LST_CWT-LST PRT | artificial construct |
| 23 | Ami2638_ami2638_CWT-LST CDS | artificial construct |
| 24 | Ami2638_ami2638_CWT-LST PRT | artificial construct |
| 25 | HXaAmi2638_CBD2638 CDS | artificial construct |
| 26 | HXaAmi2638_CBD2638 PRT | artificial construct |
| 27 | HXaAmi2638_CWT-LST CDS | artificial construct |
| 28 | HXaAmi2638_CWT-LST PRT | artificial construct |
| 29 | HXaAmi2638_CWT-NM3 CDS | artificial construct |
| 30 | HXaAmi2638_CWT-NM3 PRT | artificial construct |
| 31 | HXaCHAPK_CBD2638 CDS | artificial construct |
| 32 | HXaCHAPK_CBD2638 PRT | artificial construct |
| 33 | HXaCHAPK_CWT-LST CDS | artificial construct |
| 34 | HXaCHAPK_CWT-LST PRT | artificial construct |
| 35 | HXaCHAPK_CWT-NM3 CDS | artificial construct |
| 36 | HXaCHAPK_CWT-NM3 PRT | artificial construct |
| 37 | HXaCHAPTw_CBD2638 CDS | artificial construct |
| 38 | HXaCHAPTw_CBD2638 PRT | artificial construct |
| 39 | HXaCHAPTw_CWT-LST CDS | artificial construct |

TABLE 2-continued

SEQ ID NO overview table

| SEQ ID NO | Name construct | organism |
|---|---|---|
| 40 | HXaCHAPTw_CWT-LST PRT | artificial construct |
| 41 | HXaCHAPTw_CWT-NM3 CDS | artificial construct |
| 42 | HXaCHAPTw_CWT-NM3 PRT | artificial construct |
| 43 | HXaM23-LST_CBD2638 CDS | artificial construct |
| 44 | HXaM23-LST_CBD2638 PRT | artificial construct |
| 45 | HXaM23-LST_CWT-LST CDS | artificial construct |
| 46 | HXaM23-LST_CWT-LST PRT | artificial construct |
| 47 | HXaM23-LST_CWT-NM3 CDS | artificial construct |
| 48 | HXaM23-LST_CWT-NM3 PRT | artificial construct |
| 49 | HXaAmi2638_Ami2638_CBD2638 CDS | artificial construct |
| 50 | HXaAmi2638_Ami2638_CBD2638 PRT | artificial construct |
| 51 | HXaAmi2638_Ami2638_CWT-LST CDS | artificial construct |
| 52 | HXaAmi2638_Ami2638_CWT-LST PRT | artificial construct |
| 53 | HXaAmi2638_Ami2638_CWT-NM3 CDS | artificial construct |
| 54 | HXaAmi2638_Ami2638_CWT-NM3 PRT | artificial construct |
| 55 | HXaCHAPK_CHAPK_CBD2638 CDS | artificial construct |
| 56 | HXaCHAPK_CHAPK_CBD2638 PRT | artificial construct |
| 57 | HXaCHAPK_CHAPK_CWT-LST CDS | artificial construct |
| 58 | HXaCHAPK_CHAPK_CWT-LST PRT | artificial construct |
| 59 | HXaCHAPK_CHAPK_CWT-NM3 CDS | artificial construct |
| 60 | HXaCHAPK_CHAPK_CWT-NM3 PRT | artificial construct |
| 61 | HXaCHAPTw_CHAPTw_CBD2638 CDS | artificial construct |
| 62 | HXaCHAPTw_CHAPTw_CBD2638 PRT | artificial construct |
| 63 | HXaCHAPTw_CHAPTw_CWT-LST CDS | artificial construct |
| 64 | HXaCHAPTw_CHAPTw_CWT-LST PRT | artificial construct |
| 65 | HXaCHAPTw_CHAPTw_CWT-NM3 CDS | artificial construct |
| 66 | HXaCHAPTw_CHAPTw_CWT-NM3 PRT | artificial construct |
| 67 | HXaM23-LST_M23-LST_CBD2638 CDS | artificial construct |
| 68 | HXaM23-LST_M23-LST_CBD2638 PRT | artificial construct |
| 69 | HXaM23-LST_M23-LST_CWT-LST CDS | artificial construct |
| 70 | HXaM23-LST_M23-LST_CWT-LST PRT | artificial construct |
| 71 | HXaM23-LST_M23-LST_CWT-NM3 CDS | artificial construct |
| 72 | HXaM23-LST_M23-LST_CWT-NM3 PRT | artificial construct |
| 73 | His-tag with linker CDS | artificial construct |
| 74 | His-tag with linker PRT | artificial construct |
| 75 | LST CDS | *S. simulans* |
| 76 | LST PRT | *S. simulans* |
| 77 | HXaCHAP11_M23-2638_Ami2638_CBD2638 CDS | artificial construct |
| 78 | HXaCHAP11_M23-2638_Ami2638_CBD2638 PRT | artificial construct |
| 79 | HXaAmi11_M23-2638_Ami2638_CBD2638 CDS | artificial construct |
| 80 | HXaAmi11_M23-2638_Ami2638_CBD2638 PRT | artificial construct |
| 81 | HXaCHAPTw_Ami2638_M23-LST_CBD2638 CDS | artificial construct |
| 82 | HXaCHAPTw_Ami2638_M23-LST_CBD2638 PRT | artificial construct |
| 83 | HXaM23-LST_Ami2638_CBD2638 CDS | artificial construct |
| 84 | HXaM23-LST_Ami2638_CBD2638 PRT | artificial construct |
| 85 | HXaM23-2638_Ami2638_CBD2638_CBD2638 CDS | artificial construct |
| 86 | HXaM23-2638_Ami2638_CBD2638_CBD2638 PRT | artificial construct |
| 87 | HXaM23-2638_CBD2638 CDS | artificial construct |
| 88 | HXaM23-2638_CBD2638 PRT | artificial construct |
| 89 | HXaPly2638-Ply2638 CDS | artificial construct |
| 90 | HXaPly2638-Ply2638 PRT | artificial construct |
| 91 | HXaCHAPTw_Ami2638_M23-LST_CWT-LST CDS | artificial construct |
| 92 | HXaCHAPTw_Ami2638_M23-LST_CWT-LST PRT | artificial construct |
| 93 | HXaLST_LST CDS | artificial construct |
| 94 | HXaLST_LST PRT | artificial construct |
| 95 | HXaGFP_CBD2638 CDS | artificial construct |
| 96 | HXaGFP_CBD2638 PRT | artificial construct |
| 97 | CHAPϕ11 CDS | *S. aureus* phage phi 11 |
| 98 | CHAPϕ11 PRT | *S. aureus* phage phi 11 |
| 99 | Amiϕ11 CDS | *S. aureus* phage phi 11 |
| 100 | Amiϕ11 PRT | *S. aureus* phage phi 11 |

The invention claimed is:

1. A composition comprising a first and a second compound, wherein: the first compound is an anti-inflammatory compound; and the second compound is a compound specifically targeting a bacterial cell that comprises at least one cell wall binding domain specifically binding the peptidoglycan cell wall of said bacterial cell and is a polypeptide that has at least 80% identity with SEQ ID NO: 84, that comprises at least one cell wall binding domain that has at least 80% identity to SEQ ID NO: 6, and further comprises one or more enzymatic active domains that have at least 80% identity to SEQ ID NO: 16.

2. A kit of parts comprising:

a) a first composition comprising a first compound, wherein the first compound is an anti-inflammatory compound; and, b) a second composition comprising a second compound, wherein the second compound is a compound specifically targeting a bacterial cell that comprises at least one cell wall binding domain specifically binding the peptidoglycan cell wall of said bacterial cell and is a polypeptide that has at least 80% identity with SEQ ID NO: 84, that comprises at least one cell wall binding domain that has at least 80% identity to any of SEQ ID NO: 6, and further comprises one or more enzymatic active domains that have at least 80% identity to SEQ ID NO: 16; and optionally, c) instructions for use, preferably comprising a dosage regime.

3. A method of treating an infectious disease in a patient in need thereof comprising administering to the patient the composition of according to claim 1.

4. A method of treating an infectious disease in a patient in need thereof comprising sequentially or simultaneously administering to the patient the first and second compound comprised in the kit of claim 2.

5. The composition of claim 1, wherein said bacterial cell is a *Staphylococcus*.

6. The composition of claim 1, wherein said first compound is selected from the group consisting of a corticosteroid, a calcineurin inhibitor, an immunotherapeutic compound, a recombinant human IFN-gamma, a microbial probiotic, a cytokine modulator, an inflammatory cell recruitment blocker, and a T cell activation inhibitor.

7. The method of claim 3, wherein the patient is a human.

8. The method of claim 4, wherein the patient is a human.

9. The composition of claim 1, wherein the composition is a topical formulation.

* * * * *

SEQUENCE LISTING

```
<160> NUMBER OF SEQ ID NOS: 100

<210> SEQ ID NO 1
<211> LENGTH: 1461
<212> TYPE: DNA
<213> ORGANISM: Staphylococcus bacteriophage 2638A
```

<400> SEQUENCE: 1

```
atgctaactg ctattgacta tcttacgaaa aaaggttgga aaatatcatc tgaccctcgc     60
acttacgatg gttaccctaa aaactacggc tacagaaatt accatgaaaa cggcattaat    120
tatgatgagt tttgtggtgg ttatcataga gcttttgatg tttacagtaa cgaaactaac    180
gacgtgcctg ctgttactag cggaacagtt attgaagcaa acgattacgg taattttggt    240
ggtacattcg ttattagaga cgctaacgat aacgattgga tatatgggca tctacaacgt    300
ggctcaatgc gatttgttgt aggcgacaaa gtcaatcaag gtgacattat tggtttacaa    360
ggtaatagca actattacga caatcctatg agtgtacatt tacatttaca attacgccct    420
aaagacgcaa agaaagatga aaaatcacaa gtatgtagtg gtttggctat ggaaaaatat    480
gacattacaa atttaaatgc taaacaagat aaatcaaaga atgggagcgt gaaagagttg    540
aaacatatct attcaaacca tattaaaggt aacaagatta cagcaccaaa acctagtatt    600
caaggtgtgg tcatccacaa tgattatggt agtatgacac ctagtcaata cttaccatgg    660
ttatatgcac gtgagaataa cggtacacac gttaacggtt gggctagtgt ttatgcaaat    720
agaaacgaag tgctttggta tcatccgaca gactacgtag agtggcattg tggtaatcaa    780
tgggcaaatg ctaacttaat cggatttgaa gtgtgtgagt cgtatcctgg tagaatctcg    840
gacaaattat tcttagaaaa tgaagaagcg acattgaaag tagctgcgga tgtgatgaag    900
tcgtacggat taccagttaa tcgcaacact gtacgtctgc ataacgaatt cttcggaact    960
tcttgtccac atcgttcgtg ggacttgcat gttggcaaag gtgagcctta cacaactact   1020
aatattaata aaatgaaaga ctacttcatc aaacgcatca aacattatta tgacggtgga   1080
aagctagaag taagcaaagc agcaactatc aaacaatctg acgttaagca agaagttaaa   1140
aagcaagaag caaaacaaat tgtgaaagca acagattgga aacagaataa agatggcatt   1200
tggtataaag ctgaacatgc ttcgttcaca gtgacagcac cagagggaat tatcacaaga   1260
tacaaaggtc cttggactgg tcacccacaa gctggtgtat tacaaaaagg tcaaacgatt   1320
aaatatgatg aggttcaaaa atttgacggt catgtttggg tatcgtggga aacgtttgag   1380
ggcgaaactg tatacatgcc ggtacgcaca tgggacgcta aaactggtaa agttggtaag   1440
ttgtggggcg aaattaaata a                                              1461
```

<210> SEQ ID NO 2
<211> LENGTH: 486
<212> TYPE: PRT
<213> ORGANISM: Staphylococcus bacteriophage 2638A

<400> SEQUENCE: 2

```
Met Leu Thr Ala Ile Asp Tyr Leu Thr Lys Lys Gly Trp Lys Ile Ser
1               5                   10                  15

Ser Asp Pro Arg Thr Tyr Asp Gly Tyr Pro Lys Asn Tyr Gly Tyr Arg
            20                  25                  30

Asn Tyr His Glu Asn Gly Ile Asn Tyr Asp Glu Phe Cys Gly Gly Tyr
        35                  40                  45

His Arg Ala Phe Asp Val Tyr Ser Asn Glu Thr Asn Asp Val Pro Ala
    50                  55                  60

Val Thr Ser Gly Thr Val Ile Glu Ala Asn Asp Tyr Gly Asn Phe Gly
65                  70                  75                  80

Gly Thr Phe Val Ile Arg Asp Ala Asn Asp Asn Asp Trp Ile Tyr Gly
                85                  90                  95
```

```
His Leu Gln Arg Gly Ser Met Arg Phe Val Val Gly Asp Lys Val Asn
            100                 105                 110

Gln Gly Asp Ile Ile Gly Leu Gln Gly Asn Ser Asn Tyr Tyr Asp Asn
        115                 120                 125

Pro Met Ser Val His Leu His Leu Gln Leu Arg Pro Lys Asp Ala Lys
    130                 135                 140

Lys Asp Glu Lys Ser Gln Val Cys Ser Gly Leu Ala Met Glu Lys Tyr
145                 150                 155                 160

Asp Ile Thr Asn Leu Asn Ala Lys Gln Asp Lys Ser Lys Asn Gly Ser
                165                 170                 175

Val Lys Glu Leu Lys His Ile Tyr Ser Asn His Ile Lys Gly Asn Lys
            180                 185                 190

Ile Thr Ala Pro Lys Pro Ser Ile Gln Gly Val Val Ile His Asn Asp
        195                 200                 205

Tyr Gly Ser Met Thr Pro Ser Gln Tyr Leu Pro Trp Leu Tyr Ala Arg
    210                 215                 220

Glu Asn Asn Gly Thr His Val Asn Gly Trp Ala Ser Val Tyr Ala Asn
225                 230                 235                 240

Arg Asn Glu Val Leu Trp Tyr His Pro Thr Asp Tyr Val Glu Trp His
                245                 250                 255

Cys Gly Asn Gln Trp Ala Asn Ala Asn Leu Ile Gly Phe Glu Val Cys
            260                 265                 270

Glu Ser Tyr Pro Gly Arg Ile Ser Asp Lys Leu Phe Leu Glu Asn Glu
        275                 280                 285

Glu Ala Thr Leu Lys Val Ala Ala Asp Val Met Lys Ser Tyr Gly Leu
    290                 295                 300

Pro Val Asn Arg Asn Thr Val Arg Leu His Asn Glu Phe Phe Gly Thr
305                 310                 315                 320

Ser Cys Pro His Arg Ser Trp Asp Leu His Val Gly Lys Gly Glu Pro
                325                 330                 335

Tyr Thr Thr Thr Asn Ile Asn Lys Met Lys Asp Tyr Phe Ile Lys Arg
            340                 345                 350

Ile Lys His Tyr Tyr Asp Gly Gly Lys Leu Glu Val Ser Lys Ala Ala
        355                 360                 365

Thr Ile Lys Gln Ser Asp Val Lys Gln Glu Val Lys Lys Gln Glu Ala
    370                 375                 380

Lys Gln Ile Val Lys Ala Thr Asp Trp Lys Gln Asn Lys Asp Gly Ile
385                 390                 395                 400

Trp Tyr Lys Ala Glu His Ala Ser Phe Thr Val Thr Ala Pro Glu Gly
                405                 410                 415

Ile Ile Thr Arg Tyr Lys Gly Pro Trp Thr Gly His Pro Gln Ala Gly
            420                 425                 430

Val Leu Gln Lys Gly Gln Thr Ile Lys Tyr Asp Glu Val Gln Lys Phe
        435                 440                 445

Asp Gly His Val Trp Val Ser Trp Glu Thr Phe Glu Gly Glu Thr Val
    450                 455                 460

Tyr Met Pro Val Arg Thr Trp Asp Ala Lys Thr Gly Lys Val Gly Lys
465                 470                 475                 480

Leu Trp Gly Glu Ile Lys
                485
```

<210> SEQ ID NO 3
<211> LENGTH: 279
<212> TYPE: DNA

```
<213> ORGANISM: Staphylococcus simulans

<400> SEQUENCE: 3

tggaaaacaa acaaatatgg cacactatat aaatcagagt cagctagctt cacacctaat      60

acagatataa taacaagaac gactggtcca tttagaagca tgccgcagtc aggagtctta     120

aaagcaggtc aaacaattca ttatgatgaa gtgatgaaac aagacggtca tgtttgggta     180

ggttatacag gtaacagtgg ccaacgtatt tacttgcctg taagaacatg gaataaatct     240

actaatactt taggtgttct tggggaact ataaagtga                             279


<210> SEQ ID NO 4
<211> LENGTH: 92
<212> TYPE: PRT
<213> ORGANISM: Staphylococcus simulans

<400> SEQUENCE: 4

Trp Lys Thr Asn Lys Tyr Gly Thr Leu Tyr Lys Ser Glu Ser Ala Ser
1               5                   10                  15

Phe Thr Pro Asn Thr Asp Ile Ile Thr Arg Thr Thr Gly Pro Phe Arg
            20                  25                  30

Ser Met Pro Gln Ser Gly Val Leu Lys Ala Gly Gln Thr Ile His Tyr
        35                  40                  45

Asp Glu Val Met Lys Gln Asp Gly His Val Trp Val Gly Tyr Thr Gly
    50                  55                  60

Asn Ser Gly Gln Arg Ile Tyr Leu Pro Val Arg Thr Trp Asn Lys Ser
65                  70                  75                  80

Thr Asn Thr Leu Gly Val Leu Trp Gly Thr Ile Lys
                85                  90


<210> SEQ ID NO 5
<211> LENGTH: 285
<212> TYPE: DNA
<213> ORGANISM: Staphylococcus bacteriophage 2638A

<400> SEQUENCE: 5

tggaaacaga ataaagatgg catttggtat aaagctgaac atgcttcgtt cacagtgaca      60

gcaccagagg gaattatcac aagatacaaa ggtccttgga ctggtcaccc acaagctggt     120

gtattacaaa aaggtcaaac gattaaatat gatgaggttc aaaaatttga cggtcatgtt     180

tgggtatcgt gggaaacgtt tgagggcgaa actgtataca tgccggtacg cacatgggac     240

gctaaaactg gtaaagttgg taagttgtgg ggcgaaatta aataa                     285


<210> SEQ ID NO 6
<211> LENGTH: 94
<212> TYPE: PRT
<213> ORGANISM: Staphylococcus bacteriophage 2638A

<400> SEQUENCE: 6

Trp Lys Gln Asn Lys Asp Gly Ile Trp Tyr Lys Ala Glu His Ala Ser
1               5                   10                  15

Phe Thr Val Thr Ala Pro Glu Gly Ile Ile Thr Arg Tyr Lys Gly Pro
            20                  25                  30

Trp Thr Gly His Pro Gln Ala Gly Val Leu Gln Lys Gly Gln Thr Ile
        35                  40                  45

Lys Tyr Asp Glu Val Gln Lys Phe Asp Gly His Val Trp Val Ser Trp
    50                  55                  60

Glu Thr Phe Glu Gly Glu Thr Val Tyr Met Pro Val Arg Thr Trp Asp
```

```
65                  70                  75                  80

Ala Lys Thr Gly Lys Val Gly Lys Leu Trp Gly Glu Ile Lys
                85                  90


<210> SEQ ID NO 7
<211> LENGTH: 282
<212> TYPE: DNA
<213> ORGANISM: Staphylococcus bacteriophage phiNM3

<400> SEQUENCE: 7

ggtaaatctg caagtaaaat aacagttgga agtaaagcgc cttataacct taaatggtca      60

aaaggtgctt attttaatgc gaaaatcgac ggcttaggtg ctacttcagc cactagatac     120

ggtgataatc gtactaacta tagattcgat gttggacagg ctgtatacgc gcctggaaca     180

ttaatatatg tgtttgaaat tatagatggt tggtgtcgca tttattggaa caatcataat     240

gagtggatat ggcatgagag attgattgtg aaagaagtgt tt                        282


<210> SEQ ID NO 8
<211> LENGTH: 94
<212> TYPE: PRT
<213> ORGANISM: Staphylococcus bacteriophage phiNM3

<400> SEQUENCE: 8

Gly Lys Ser Ala Ser Lys Ile Thr Val Gly Ser Lys Ala Pro Tyr Asn
1               5                   10                  15

Leu Lys Trp Ser Lys Gly Ala Tyr Phe Asn Ala Lys Ile Asp Gly Leu
            20                  25                  30

Gly Ala Thr Ser Ala Thr Arg Tyr Gly Asp Asn Arg Thr Asn Tyr Arg
        35                  40                  45

Phe Asp Val Gly Gln Ala Val Tyr Ala Pro Gly Thr Leu Ile Tyr Val
    50                  55                  60

Phe Glu Ile Ile Asp Gly Trp Cys Arg Ile Tyr Trp Asn Asn His Asn
65                  70                  75                  80

Glu Trp Ile Trp His Glu Arg Leu Ile Val Lys Glu Val Phe
                85                  90


<210> SEQ ID NO 9
<211> LENGTH: 585
<212> TYPE: DNA
<213> ORGANISM: Staphylococcus bacteriophage K

<400> SEQUENCE: 9

atggctaaga ctcaagcaga aataaataaa cgtttagatg cttatgcaaa aggaacagta      60

gatagccctt acagagttaa aaaagctaca agttatgacc catcatttgg tgtaatggaa     120

gcaggagcca ttgatgcaga tggttactat cacgctcagt gtcaagacct tattacagac     180

tatgttttat ggttaacaga taataaagtt agaacttggg gtaatgctaa agaccaaatt     240

aaacagagtt atggtactgg atttaaaata catgaaaata aaccttctac tgtacctaaa     300

aaaggttgga ttgcggtatt tacatccggt agttatgaac agtggggtca cataggtatt     360

gtatatgatg gaggtaatac ttctacattt actattttag agcaaaactg gaatggttat     420

gctaataaaa aacctacaaa acgtgtagat aattattacg gattaactca cttcattgaa     480

atacctgtaa aagcaggaac tactgttaaa aaagaaacag ctaagaaaag cgcaagtaaa     540

acgcctgcac ctaaaaagaa agcaacacta aaagtttcta agaat                     585


<210> SEQ ID NO 10
```

```
<211> LENGTH: 195
<212> TYPE: PRT
<213> ORGANISM: Staphylococcus bacteriophage K

<400> SEQUENCE: 10

Met Ala Lys Thr Gln Ala Glu Ile Asn Lys Arg Leu Asp Ala Tyr Ala
1               5                   10                  15

Lys Gly Thr Val Asp Ser Pro Tyr Arg Val Lys Lys Ala Thr Ser Tyr
            20                  25                  30

Asp Pro Ser Phe Gly Val Met Glu Ala Gly Ala Ile Asp Ala Asp Gly
        35                  40                  45

Tyr Tyr His Ala Gln Cys Gln Asp Leu Ile Thr Asp Tyr Val Leu Trp
    50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Glu Gln Trp Gly His Ile Gly Ile Val Tyr Asp Gly Gly Asn Thr Ser
        115                 120                 125

Thr Phe Thr Ile Leu Glu Gln Asn Trp Asn Gly Tyr Ala Asn Lys Lys
    130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Lys Ala Thr Leu Lys Val
            180                 185                 190

Ser Lys Asn
        195


<210> SEQ ID NO 11
<211> LENGTH: 420
<212> TYPE: DNA
<213> ORGANISM: Staphylococcus bacteriophage Twort

<400> SEQUENCE: 11

atgaaaaccc tgaaacaagc agagtcctac attaagagta aagtaaatac aggaactgat      60

tttgatggtt tatatgggta tcagtgtatg gacttagcag tagattatat ttaccatgta     120

acagatggta aaataagaat gtggggtaat gctaaggatg cgataaataa ctcttttggt     180

ggtactgcta cggtatataa aaactaccct gcttttagac ctaagtacgg tgatgtagtc     240

gtatggacta ctggtaattt tgcaacttat ggtcatatcg caatagttac taaccctgac     300

ccttatggag accttcaata tgttacagtt cttgaacaaa actggaacgg taacgggatt     360

tataaaaccg agttagctac aatcagaaca cacgattaca caggaattac acattttatt     420


<210> SEQ ID NO 12
<211> LENGTH: 140
<212> TYPE: PRT
<213> ORGANISM: Staphylococcus bacteriophage Twort

<400> SEQUENCE: 12

Met Lys Thr Leu Lys Gln Ala Glu Ser Tyr Ile Lys Ser Lys Val Asn
1               5                   10                  15

Thr Gly Thr Asp Phe Asp Gly Leu Tyr Gly Tyr Gln Cys Met Asp Leu
```

```
            20                  25                  30

Ala Val Asp Tyr Ile Tyr His Val Thr Asp Gly Lys Ile Arg Met Trp
        35                  40                  45

Gly Asn Ala Lys Asp Ala Ile Asn Asn Ser Phe Gly Gly Thr Ala Thr
    50                  55                  60

Val Tyr Lys Asn Tyr Pro Ala Phe Arg Pro Lys Tyr Gly Asp Val Val
65                  70                  75                  80

Val Trp Thr Thr Gly Asn Phe Ala Thr Tyr Gly His Ile Ala Ile Val
                85                  90                  95

Thr Asn Pro Asp Pro Tyr Gly Asp Leu Gln Tyr Val Thr Val Leu Glu
            100                 105                 110

Gln Asn Trp Asn Gly Asn Gly Ile Tyr Lys Thr Glu Leu Ala Thr Ile
        115                 120                 125

Arg Thr His Asp Tyr Thr Gly Ile Thr His Phe Ile
    130                 135                 140


<210> SEQ ID NO 13
<211> LENGTH: 438
<212> TYPE: DNA
<213> ORGANISM: Staphylococcus bacteriophage 2638A

<400> SEQUENCE: 13

atgctaactg ctattgacta tcttacgaaa aaaggttgga aaatatcatc tgaccctcgc      60

acttacgatg gttaccctaa aaactacggc tacagaaatt accatgaaaa cggcattaat     120

tatgatgagt tttgtggtgg ttatcataga gcttttgatg tttacagtaa cgaaactaac     180

gacgtgcctg ctgttactag cggaacagtt attgaagcaa acgattacgg taattttggt     240

ggtacattcg ttattagaga cgctaacgat aacgattgga tatatgggca tctacaacgt     300

ggctcaatgc gatttgttgt aggcgacaaa gtcaatcaag gtgacattat tggtttacaa     360

ggtaatagca actattacga caatcctatg agtgtacatt tacatttaca attacgccct     420

aaagacgcaa agaaagat                                                   438


<210> SEQ ID NO 14
<211> LENGTH: 146
<212> TYPE: PRT
<213> ORGANISM: Staphylococcus bacteriophage 2638A

<400> SEQUENCE: 14

Met Leu Thr Ala Ile Asp Tyr Leu Thr Lys Lys Gly Trp Lys Ile Ser
1               5                   10                  15

Ser Asp Pro Arg Thr Tyr Asp Gly Tyr Pro Lys Asn Tyr Gly Tyr Arg
            20                  25                  30

Asn Tyr His Glu Asn Gly Ile Asn Tyr Asp Glu Phe Cys Gly Gly Tyr
        35                  40                  45

His Arg Ala Phe Asp Val Tyr Ser Asn Glu Thr Asn Asp Val Pro Ala
    50                  55                  60

Val Thr Ser Gly Thr Val Ile Glu Ala Asn Asp Tyr Gly Asn Phe Gly
65                  70                  75                  80

Gly Thr Phe Val Ile Arg Asp Ala Asn Asp Asn Asp Trp Ile Tyr Gly
                85                  90                  95

His Leu Gln Arg Gly Ser Met Arg Phe Val Val Gly Asp Lys Val Asn
            100                 105                 110

Gln Gly Asp Ile Ile Gly Leu Gln Gly Asn Ser Asn Tyr Tyr Asp Asn
        115                 120                 125
```

-continued

```
Pro Met Ser Val His Leu His Leu Gln Leu Arg Pro Lys Asp Ala Lys
    130                 135                 140

Lys Asp
145


<210> SEQ ID NO 15
<211> LENGTH: 420
<212> TYPE: DNA
<213> ORGANISM: Staphylococcus simulans

<400> SEQUENCE: 15

gctgcaacac atgaacattc agcacaatgg ttgaataatt acaaaaaagg atatggttac      60

ggtccttatc cattaggtat aaatggcggt atgcactacg gagttgattt ttttatgaat     120

attggaacac cagtaaaagc tatttcaagc ggaaaaatag ttgaagctgg ttggagtaat     180

tacggaggag gtaatcaaat aggtcttatt gaaaatgatg gagtgcatag acaatggtat     240

atgcatctaa gtaaatataa tgttaaagta ggagattatg tcaaagctgg tcaaataatc     300

ggttggtctg gaagcactgg ttattctaca gcaccacatt tacacttcca aagaatggtt     360

aattcatttt caaattcaac tgcccaagat ccaatgcctt tcttaaagag cgcaggatat     420


<210> SEQ ID NO 16
<211> LENGTH: 140
<212> TYPE: PRT
<213> ORGANISM: Staphylococcus simulans

<400> SEQUENCE: 16

Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Ile Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Ser Phe Ser Asn Ser Thr Ala
        115                 120                 125

Gln Asp Pro Met Pro Phe Leu Lys Ser Ala Gly Tyr
    130                 135                 140


<210> SEQ ID NO 17
<211> LENGTH: 510
<212> TYPE: DNA
<213> ORGANISM: Staphylococcus bacteriophage 2638A

<400> SEQUENCE: 17

ggtaacaaga ttacagcacc aaaacctagt attcaaggtg tggtcatcca caatgattat      60

ggtagtatga cacctagtca atacttacca tggttatatg cacgtgagaa taacggtaca     120

cacgttaacg gttgggctag tgtttatgca aatagaaacg aagtgctttg gtatcatccg     180

acagactacg tagagtggca ttgtggtaat caatgggcaa atgctaactt aatcggattt     240
```

```
gaagtgtgtg agtcgtatcc tggtagaatc tcggacaaat tattcttaga aaatgaagaa    300

gcgacattga aagtagctgc ggatgtgatg aagtcgtacg gattaccagt taatcgcaac    360

actgtacgtc tgcataacga attcttcgga acttcttgtc cacatcgttc gtgggacttg    420

catgttggca aaggtgagcc ttacacaact actaatatta ataaaatgaa agactacttc    480

atcaaacgca tcaaacatta ttatgacggt                                      510
```

<210> SEQ ID NO 18
<211> LENGTH: 169
<212> TYPE: PRT
<213> ORGANISM: Staphylococcus bacteriophage 2638A

<400> SEQUENCE: 18

```
Asn Lys Ile Thr Ala Pro Lys Pro Ser Ile Gln Gly Val Val Ile His
1               5                   10                  15

Asn Asp Tyr Gly Ser Met Thr Pro Ser Gln Tyr Leu Pro Trp Leu Tyr
            20                  25                  30

Ala Arg Glu Asn Asn Gly Thr His Val Asn Gly Trp Ala Ser Val Tyr
        35                  40                  45

Ala Asn Arg Asn Glu Val Leu Trp Tyr His Pro Thr Asp Tyr Val Glu
    50                  55                  60

Trp His Cys Gly Asn Gln Trp Ala Asn Ala Asn Leu Ile Gly Phe Glu
65                  70                  75                  80

Val Cys Glu Ser Tyr Pro Gly Arg Ile Ser Asp Lys Leu Phe Leu Glu
                85                  90                  95

Asn Glu Glu Ala Thr Leu Lys Val Ala Ala Asp Val Met Lys Ser Tyr
            100                 105                 110

Gly Leu Pro Val Asn Arg Asn Thr Val Arg Leu His Asn Glu Phe Phe
        115                 120                 125

Gly Thr Ser Cys Pro His Arg Ser Trp Asp Leu His Val Gly Lys Gly
    130                 135                 140

Glu Pro Tyr Thr Thr Thr Asn Ile Asn Lys Met Lys Asp Tyr Phe Ile
145                 150                 155                 160

Lys Arg Ile Lys His Tyr Tyr Asp Gly
                165
```

<210> SEQ ID NO 19
<211> LENGTH: 1407
<212> TYPE: DNA
<213> ORGANISM: artificial
<220> FEATURE:
<223> OTHER INFORMATION: artificial construct

<400> SEQUENCE: 19

```
atggctaaga ctcaagcaga aataaataaa cgtttagatg cttatgcaaa aggaacagta     60

gatagccctt acagagttaa aaaagctaca agttatgacc catcatttgg tgtaatggaa    120

gcaggagcca ttgatgcaga tggttactat cacgctcagt gtcaagacct tattacagac    180

tatgttttat ggttaacaga taataaagtt agaacttggg gtaatgctaa agaccaaatt    240

aaacagagtt atggtactgg atttaaaata catgaaaata aaccttctac tgtacctaaa    300

aaaggttgga ttgcggtatt tacatccggt agttatgaac agtggggtca cataggtatt    360

gtatatgatg gaggtaatac ttctacattt actattttag agcaaaactg gaatggttat    420

gctaataaaa aacctacaaa acgtgtagat aattattacg gattaactca cttcattgaa    480

atacctgtaa aagcaggaac tactgttaaa aaagaaacag ctaagaaaag cgcaagtaaa    540
```

```
acgcctgcac ctaaaaagaa agcaacacta aaagtttcta agaatgagct catggctaag    600

actcaagcag aaataaataa acgtttagat gcttatgcaa aaggaacagt agatagccct    660

tacagagtta aaaaagctac aagttatgac ccatcatttg gtgtaatgga agcaggagcc    720

attgatgcag atggttacta tcacgctcag tgtcaagacc ttattacaga ctatgtttta    780

tggttaacag ataataaagt tagaacttgg ggtaatgcta aagaccaaat taaacagagt    840

tatggtactg gatttaaaat acatgaaaat aaaccttcta ctgtacctaa aaaaggttgg    900

attgcggtat ttacatccgg tagttatgaa cagtggggtc acataggtat tgtatatgat    960

ggaggtaata cttctacatt tactatttta gagcaaaact ggaatggtta tgctaataaa   1020

aaacctacaa aacgtgtaga taattattac ggattaactc acttcattga aatacctgta   1080

aaagcaggaa aagcaggtgg tacagtaact ccaacgccga atacaggttg gaaaacaaac   1140

aaatatggca cactatataa atcagagtca gctagcttca cacctaatac agatataata   1200

acaagaacga ctggtccatt tagaagcatg ccgcagtcag gagtcttaaa agcaggtcaa   1260

acaattcatt atgatgaagt gatgaaacaa gacggtcatg tttgggtagg ttatacaggt   1320

aacagtggcc aacgtattta cttgcctgta agaacatgga ataaatctac taatacttta   1380

ggtgttcttt ggggaactat aaagtaa                                       1407
```

<210> SEQ ID NO 20
<211> LENGTH: 468
<212> TYPE: PRT
<213> ORGANISM: artificial
<220> FEATURE:
<223> OTHER INFORMATION: artificial construct

<400> SEQUENCE: 20

```
Met Ala Lys Thr Gln Ala Glu Ile Asn Lys Arg Leu Asp Ala Tyr Ala
1               5                   10                  15

Lys Gly Thr Val Asp Ser Pro Tyr Arg Val Lys Lys Ala Thr Ser Tyr
            20                  25                  30

Asp Pro Ser Phe Gly Val Met Glu Ala Gly Ala Ile Asp Ala Asp Gly
        35                  40                  45

Tyr Tyr His Ala Gln Cys Gln Asp Leu Ile Thr Asp Tyr Val Leu Trp
    50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Glu Gln Trp Gly His Ile Gly Ile Val Tyr Asp Gly Gly Asn Thr Ser
        115                 120                 125

Thr Phe Thr Ile Leu Glu Gln Asn Trp Asn Gly Tyr Ala Asn Lys Lys
    130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Lys Ala Thr Leu Lys Val
            180                 185                 190

Ser Lys Asn Glu Leu Met Ala Lys Thr Gln Ala Glu Ile Asn Lys Arg
        195                 200                 205
```

```
Leu Asp Ala Tyr Ala Lys Gly Thr Val Asp Ser Pro Tyr Arg Val Lys
    210                 215                 220

Lys Ala Thr Ser Tyr Asp Pro Ser Phe Gly Val Met Glu Ala Gly Ala
225                 230                 235                 240

Ile Asp Ala Asp Gly Tyr Tyr His Ala Gln Cys Gln Asp Leu Ile Thr
                245                 250                 255

Asp Tyr Val Leu Trp Leu Thr Asp Asn Lys Val Arg Thr Trp Gly Asn
            260                 265                 270

Ala Lys Asp Gln Ile Lys Gln Ser Tyr Gly Thr Gly Phe Lys Ile His
        275                 280                 285

Glu Asn Lys Pro Ser Thr Val Pro Lys Lys Gly Trp Ile Ala Val Phe
    290                 295                 300

Thr Ser Gly Ser Tyr Glu Gln Trp Gly His Ile Gly Ile Val Tyr Asp
305                 310                 315                 320

Gly Gly Asn Thr Ser Thr Phe Thr Ile Leu Glu Gln Asn Trp Asn Gly
                325                 330                 335

Tyr Ala Asn Lys Lys Pro Thr Lys Arg Val Asp Asn Tyr Tyr Gly Leu
            340                 345                 350

Thr His Phe Ile Glu Ile Pro Val Lys Ala Gly Lys Ala Gly Gly Thr
        355                 360                 365

Val Thr Pro Thr Pro Asn Thr Gly Trp Lys Thr Asn Lys Tyr Gly Thr
    370                 375                 380

Leu Tyr Lys Ser Glu Ser Ala Ser Phe Thr Pro Asn Thr Asp Ile Ile
385                 390                 395                 400

Thr Arg Thr Thr Gly Pro Phe Arg Ser Met Pro Gln Ser Gly Val Leu
                405                 410                 415

Lys Ala Gly Gln Thr Ile His Tyr Asp Glu Val Met Lys Gln Asp Gly
            420                 425                 430

His Val Trp Val Gly Tyr Thr Gly Asn Ser Gly Gln Arg Ile Tyr Leu
        435                 440                 445

Pro Val Arg Thr Trp Asn Lys Ser Thr Asn Thr Leu Gly Val Leu Trp
    450                 455                 460

Gly Thr Ile Lys
465
```

<210> SEQ ID NO 21
<211> LENGTH: 1209
<212> TYPE: DNA
<213> ORGANISM: artificial
<220> FEATURE:
<223> OTHER INFORMATION: artificial construct

<400> SEQUENCE: 21

```
gctgcaacac atgaacattc agcacaatgg ttgaataatt acaaaaaagg atatggttac      60

ggtccttatc cattaggtat aaatggcggt atgcactacg gagttgattt ttttatgaat     120

attggaacac cagtaaaagc tatttcaagc ggaaaaatag ttgaagctgg ttggagtaat     180

tacggaggag gtaatcaaat aggtcttatt gaaaatgatg gagtgcatag acaatggtat     240

atgcatctaa gtaaatataa tgttaaagta ggagattatg tcaaagctgg tcaaataatc     300

ggttggtctg gaagcactgg ttattctaca gcaccacatt tacacttcca aagaatggtt     360

aattcatttt caaattcaac tgcccaagat ccaatgcctt tcttaaagag cgcaggatat     420

ggaaaagcag gtggtacagt aactccaacg ccgaatacag gtgagctcgc tgcaacacat     480

gaacattcag cacaatggtt gaataattac aaaaaaggat atggttacgg tccttatcca     540
```

```
ttaggtataa atggcggtat gcactacgga gttgattttt ttatgaatat tggaacacca    600

gtaaaagcta tttcaagcgg aaaaatagtt gaagctggtt ggagtaatta cggaggaggt    660

aatcaaatag gtcttattga aaatgatgga gtgcatagac aatggtatat gcatctaagt    720

aaatataatg ttaaagtagg agattatgtc aaagctggtc aaataatcgg ttggtctgga    780

agcactggtt attctacagc accacattta cacttccaaa gaatggttaa ttcattttca    840

aattcaactg cccaagatcc aatgcctttc ttaaagagcg caggatatgg aaaagcaggt    900

ggtacagtaa ctccaacgcc gaatacaggt tggaaaacaa acaaatatgg cacactatat    960

aaatcagagt cagctagctt cacacctaat acagatataa taacaagaac gactggtcca   1020

tttagaagca tgccgcagtc aggagtctta aaagcaggtc aaacaattca ttatgatgaa   1080

gtgatgaaac aagacggtca tgtttgggta ggttatacag gtaacagtgg ccaacgtatt   1140

tacttgcctg taagaacatg gaataaatct actaatactt taggtgttct ttggggaact   1200

ataaagtaa                                                           1209
```

<210> SEQ ID NO 22
<211> LENGTH: 402
<212> TYPE: PRT
<213> ORGANISM: artificial
<220> FEATURE:
<223> OTHER INFORMATION: artificial construct

<400> SEQUENCE: 22

```
Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Ile Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Ser Phe Ser Asn Ser Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Glu Leu Ala Ala Thr His
145                 150                 155                 160

Glu His Ser Ala Gln Trp Leu Asn Asn Tyr Lys Lys Gly Tyr Gly Tyr
                165                 170                 175

Gly Pro Tyr Pro Leu Gly Ile Asn Gly Gly Met His Tyr Gly Val Asp
            180                 185                 190

Phe Phe Met Asn Ile Gly Thr Pro Val Lys Ala Ile Ser Ser Gly Lys
        195                 200                 205

Ile Val Glu Ala Gly Trp Ser Asn Tyr Gly Gly Gly Asn Gln Ile Gly
    210                 215                 220

Leu Ile Glu Asn Asp Gly Val His Arg Gln Trp Tyr Met His Leu Ser
225                 230                 235                 240
```

```
Lys Tyr Asn Val Lys Val Gly Asp Tyr Val Lys Ala Gly Gln Ile Ile
                245                 250                 255

Gly Trp Ser Gly Ser Thr Gly Tyr Ser Thr Ala Pro His Leu His Phe
            260                 265                 270

Gln Arg Met Val Asn Ser Phe Ser Asn Ser Thr Ala Gln Asp Pro Met
        275                 280                 285

Pro Phe Leu Lys Ser Ala Gly Tyr Gly Lys Ala Gly Gly Thr Val Thr
    290                 295                 300

Pro Thr Pro Asn Thr Gly Trp Lys Thr Asn Lys Tyr Gly Thr Leu Tyr
305                 310                 315                 320

Lys Ser Glu Ser Ala Ser Phe Thr Pro Asn Thr Asp Ile Ile Thr Arg
                325                 330                 335

Thr Thr Gly Pro Phe Arg Ser Met Pro Gln Ser Gly Val Leu Lys Ala
            340                 345                 350

Gly Gln Thr Ile His Tyr Asp Glu Val Met Lys Gln Asp Gly His Val
        355                 360                 365

Trp Val Gly Tyr Thr Gly Asn Ser Gly Gln Arg Ile Tyr Leu Pro Val
    370                 375                 380

Arg Thr Trp Asn Lys Ser Thr Asn Thr Leu Gly Val Leu Trp Gly Thr
385                 390                 395                 400

Ile Lys
```

<210> SEQ ID NO 23
<211> LENGTH: 1686
<212> TYPE: DNA
<213> ORGANISM: artificial
<220> FEATURE:
<223> OTHER INFORMATION: artificial construct

<400> SEQUENCE: 23

```
gcaaagaaag atgaaaaatc acaagtatgt agtggtttgg ctatggaaaa atatgacatt      60

acaaatttaa atgctaaaca agataaatca aagaatggga gcgtgaaaga gttgaaacat     120

atctattcaa accatattaa aggtaacaag attacagcac caaaacctag tattcaaggt     180

gtggtcatcc acaatgatta tggtagtatg acacctagtc aatacttacc atggttatat     240

gcacgtgaga ataacggtac acacgttaac ggttgggcta gtgtttatgc aaatagaaac     300

gaagtgcttt ggtatcatcc gacagactac gtagagtggc attgtggtaa tcaatgggca     360

aatgctaact taatcggatt tgaagtgtgt gagtcgtatc ctggtagaat ctcggacaaa     420

ttattcttag aaaatgaaga agcgacattg aaagtagctg cggatgtgat gaagtcgtac     480

ggattaccag ttaatcgcaa cactgtacgt ctgcataacg aattcttcgg aacttcttgt     540

ccacatcgtt cgtgggactt gcatgttggc aaaggtgagc cttacacaac tactaatatt     600

aataaaatga aagactactt catcaaacgc atcaaacatt attatgacgg tgagctcgca     660

aagaaagatg aaaaatcaca agtatgtagt ggtttggcta tggaaaaata tgacattaca     720

aatttaaatg ctaaacaaga taaatcaaag aatgggagcg tgaaagagtt gaaacatatc     780

tattcaaacc atattaaagg taacaagatt acagcaccaa aacctagtat tcaaggtgtg     840

gtcatccaca atgattatgg tagtatgaca cctagtcaat acttaccatg gttatatgca     900

cgtgagaata acggtacaca cgttaacggt tgggctagtg tttatgcaaa tagaaacgaa     960

gtgctttggt atcatccgac agactacgta gagtggcatt gtggtaatca atgggcaaat    1020

gctaacttaa tcggatttga agtgtgtgag tcgtatcctg gtagaatctc ggacaaatta    1080

ttcttagaaa atgaagaagc gacattgaaa gtagctgcgg atgtgatgaa gtcgtacgga    1140
```

```
ttaccagtta atcgcaacac tgtacgtctg cataacgaat tcttcggaac ttcttgtcca   1200

catcgttcgt gggacttgca tgttggcaaa ggtgagcctt acacaactac taatattaat   1260

aaaatgaaag actacttcat caaacgcatc aaacattatt atgacggtgg aaagctagaa   1320

gtaagcaaag cagcaactat caaacaatct gacgttaagc aagaagttaa aaagcaagaa   1380

gcaaaacaaa ttgtgaaagc aacagattgg aaaacaaaca aatatggcac actatataaa   1440

tcagagtcag ctagcttcac acctaataca gatataataa caagaacgac tggtccattt   1500

agaagcatgc cgcagtcagg agtcttaaaa gcaggtcaaa caattcatta tgatgaagtg   1560

atgaaacaag acggtcatgt ttgggtaggt tatacaggta acagtggcca acgtatttac   1620

ttgcctgtaa gaacatggaa taaatctact aatactttag gtgttctttg ggaactata    1680

aagtaa                                                              1686
```

<210> SEQ ID NO 24
<211> LENGTH: 561
<212> TYPE: PRT
<213> ORGANISM: artificial
<220> FEATURE:
<223> OTHER INFORMATION: artificial construct

<400> SEQUENCE: 24

```
Ala Lys Lys Asp Glu Lys Ser Gln Val Cys Ser Gly Leu Ala Met Glu
1               5                   10                  15

Lys Tyr Asp Ile Thr Asn Leu Asn Ala Lys Gln Asp Lys Ser Lys Asn
            20                  25                  30

Gly Ser Val Lys Glu Leu Lys His Ile Tyr Ser Asn His Ile Lys Gly
        35                  40                  45

Asn Lys Ile Thr Ala Pro Lys Pro Ser Ile Gln Gly Val Val Ile His
    50                  55                  60

Asn Asp Tyr Gly Ser Met Thr Pro Ser Gln Tyr Leu Pro Trp Leu Tyr
65                  70                  75                  80

Ala Arg Glu Asn Asn Gly Thr His Val Asn Gly Trp Ala Ser Val Tyr
                85                  90                  95

Ala Asn Arg Asn Glu Val Leu Trp Tyr His Pro Thr Asp Tyr Val Glu
            100                 105                 110

Trp His Cys Gly Asn Gln Trp Ala Asn Ala Asn Leu Ile Gly Phe Glu
        115                 120                 125

Val Cys Glu Ser Tyr Pro Gly Arg Ile Ser Asp Lys Leu Phe Leu Glu
    130                 135                 140

Asn Glu Glu Ala Thr Leu Lys Val Ala Ala Asp Val Met Lys Ser Tyr
145                 150                 155                 160

Gly Leu Pro Val Asn Arg Asn Thr Val Arg Leu His Asn Glu Phe Phe
                165                 170                 175

Gly Thr Ser Cys Pro His Arg Ser Trp Asp Leu His Val Gly Lys Gly
            180                 185                 190

Glu Pro Tyr Thr Thr Thr Asn Ile Asn Lys Met Lys Asp Tyr Phe Ile
        195                 200                 205

Lys Arg Ile Lys His Tyr Tyr Asp Gly Glu Leu Ala Lys Lys Asp Glu
    210                 215                 220

Lys Ser Gln Val Cys Ser Gly Leu Ala Met Glu Lys Tyr Asp Ile Thr
225                 230                 235                 240

Asn Leu Asn Ala Lys Gln Asp Lys Ser Lys Asn Gly Ser Val Lys Glu
                245                 250                 255
```

```
Leu Lys His Ile Tyr Ser Asn His Ile Lys Gly Asn Lys Ile Thr Ala
            260                 265                 270

Pro Lys Pro Ser Ile Gln Gly Val Val Ile His Asn Asp Tyr Gly Ser
        275                 280                 285

Met Thr Pro Ser Gln Tyr Leu Pro Trp Leu Tyr Ala Arg Glu Asn Asn
    290                 295                 300

Gly Thr His Val Asn Gly Trp Ala Ser Val Tyr Ala Asn Arg Asn Glu
305                 310                 315                 320

Val Leu Trp Tyr His Pro Thr Asp Tyr Val Glu Trp His Cys Gly Asn
                325                 330                 335

Gln Trp Ala Asn Ala Asn Leu Ile Gly Phe Glu Val Cys Glu Ser Tyr
            340                 345                 350

Pro Gly Arg Ile Ser Asp Lys Leu Phe Leu Glu Asn Glu Glu Ala Thr
        355                 360                 365

Leu Lys Val Ala Ala Asp Val Met Lys Ser Tyr Gly Leu Pro Val Asn
    370                 375                 380

Arg Asn Thr Val Arg Leu His Asn Glu Phe Phe Gly Thr Ser Cys Pro
385                 390                 395                 400

His Arg Ser Trp Asp Leu His Val Gly Lys Gly Glu Pro Tyr Thr Thr
                405                 410                 415

Thr Asn Ile Asn Lys Met Lys Asp Tyr Phe Ile Lys Arg Ile Lys His
            420                 425                 430

Tyr Tyr Asp Gly Gly Lys Leu Glu Val Ser Lys Ala Ala Thr Ile Lys
        435                 440                 445

Gln Ser Asp Val Lys Gln Glu Val Lys Lys Gln Glu Ala Lys Gln Ile
    450                 455                 460

Val Lys Ala Thr Asp Trp Lys Thr Asn Lys Tyr Gly Thr Leu Tyr Lys
465                 470                 475                 480

Ser Glu Ser Ala Ser Phe Thr Pro Asn Thr Asp Ile Ile Thr Arg Thr
                485                 490                 495

Thr Gly Pro Phe Arg Ser Met Pro Gln Ser Gly Val Leu Lys Ala Gly
            500                 505                 510

Gln Thr Ile His Tyr Asp Glu Val Met Lys Gln Asp Gly His Val Trp
        515                 520                 525

Val Gly Tyr Thr Gly Asn Ser Gly Gln Arg Ile Tyr Leu Pro Val Arg
    530                 535                 540

Thr Trp Asn Lys Ser Thr Asn Thr Leu Gly Val Leu Trp Gly Thr Ile
545                 550                 555                 560

Lys
```

<210> SEQ ID NO 25
<211> LENGTH: 1131
<212> TYPE: DNA
<213> ORGANISM: artificial
<220> FEATURE:
<223> OTHER INFORMATION: artificial construct

<400> SEQUENCE: 25

```
atgagaggat cgcatcacca tcaccatcac ggatctggct ctggatctgg tatcgaggga      60

aggccttata atggaactgg atccgcatgc gagctcgcaa agaaagatga aaaatcacaa     120

gtatgtagtg gtttggctat ggaaaaatat gacattacaa atttaaatgc taaacaagat     180

aaatcaaaga atgggagcgt gaaagagttg aaacatatct attcaaacca tattaaaggt     240

aacaagatta cagcaccaaa acctagtatt caaggtgtgg tcatccacaa tgattatggt     300
```

```
agtatgacac ctagtcaata cttaccatgg ttatatgcac gtgagaataa cggtacacac    360

gttaacggtt gggctagtgt ttatgcaaat agaaacgaag tgctttggta tcatccgaca    420

gactacgtag agtggcattg tggtaatcaa tgggcaaatg ctaacttaat cggatttgaa    480

gtgtgtgagt cgtatcctgg tagaatctcg gacaaattat tcttagaaaa tgaagaagcg    540

acattgaaag tagctgcgga tgtgatgaag tcgtacggat taccagttaa tcgcaacact    600

gtacgtctgc ataacgaatt cttcggaact tcttgtccac atcgttcgtg ggacttgcat    660

gttggcaaag gtgagcctta cacaactact aatattaata aaatgaaaga ctacttcatc    720

aaacgcatca aacattatta tgacggtgga aagctagaag taagcaaagc agcaactatc    780

aaacaatctg acgttaagca agaagttaaa aagcaagaag caaaacaaat tgtgaaagca    840

acagattgga aacagaataa agatggcatt tggtataaag ctgaacatgc ttcgttcaca    900

gtgacagcac cagagggaat tatcacaaga tacaaaggtc cttggactgg tcacccacaa    960

gctggtgtat tacaaaaagg tcaaacgatt aaatatgatg aggttcaaaa atttgacggt   1020

catgtttggg tatcgtggga aacgtttgag ggcgaaactg tatacatgcc ggtacgcaca   1080

tgggacgcta aaactggtaa agttggtaag ttgtggggcg aaattaaata a            1131
```

```
<210> SEQ ID NO 26
<211> LENGTH: 376
<212> TYPE: PRT
<213> ORGANISM: artificial
<220> FEATURE:
<223> OTHER INFORMATION: artificial construct

<400> SEQUENCE: 26

Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Ala Lys Lys Asp Glu Lys Ser Gln Val Cys Ser Gly Leu Ala Met Glu
        35                  40                  45

Lys Tyr Asp Ile Thr Asn Leu Asn Ala Lys Gln Asp Lys Ser Lys Asn
    50                  55                  60

Gly Ser Val Lys Glu Leu Lys His Ile Tyr Ser Asn His Ile Lys Gly
65                  70                  75                  80

Asn Lys Ile Thr Ala Pro Lys Pro Ser Ile Gln Gly Val Val Ile His
                85                  90                  95

Asn Asp Tyr Gly Ser Met Thr Pro Ser Gln Tyr Leu Pro Trp Leu Tyr
            100                 105                 110

Ala Arg Glu Asn Asn Gly Thr His Val Asn Gly Trp Ala Ser Val Tyr
        115                 120                 125

Ala Asn Arg Asn Glu Val Leu Trp Tyr His Pro Thr Asp Tyr Val Glu
    130                 135                 140

Trp His Cys Gly Asn Gln Trp Ala Asn Ala Asn Leu Ile Gly Phe Glu
145                 150                 155                 160

Val Cys Glu Ser Tyr Pro Gly Arg Ile Ser Asp Lys Leu Phe Leu Glu
                165                 170                 175

Asn Glu Glu Ala Thr Leu Lys Val Ala Ala Asp Val Met Lys Ser Tyr
            180                 185                 190

Gly Leu Pro Val Asn Arg Asn Thr Val Arg Leu His Asn Glu Phe Phe
        195                 200                 205

Gly Thr Ser Cys Pro His Arg Ser Trp Asp Leu His Val Gly Lys Gly
    210                 215                 220
```

```
Glu Pro Tyr Thr Thr Thr Asn Ile Asn Lys Met Lys Asp Tyr Phe Ile
225                 230                 235                 240

Lys Arg Ile Lys His Tyr Tyr Asp Gly Gly Lys Leu Glu Val Ser Lys
                245                 250                 255

Ala Ala Thr Ile Lys Gln Ser Asp Val Lys Gln Glu Val Lys Lys Gln
            260                 265                 270

Glu Ala Lys Gln Ile Val Lys Ala Thr Asp Trp Lys Gln Asn Lys Asp
        275                 280                 285

Gly Ile Trp Tyr Lys Ala Glu His Ala Ser Phe Thr Val Thr Ala Pro
    290                 295                 300

Glu Gly Ile Ile Thr Arg Tyr Lys Gly Pro Trp Thr Gly His Pro Gln
305                 310                 315                 320

Ala Gly Val Leu Gln Lys Gly Gln Thr Ile Lys Tyr Asp Glu Val Gln
                325                 330                 335

Lys Phe Asp Gly His Val Trp Val Ser Trp Glu Thr Phe Glu Gly Glu
            340                 345                 350

Thr Val Tyr Met Pro Val Arg Thr Trp Asp Ala Lys Thr Gly Lys Val
        355                 360                 365

Gly Lys Leu Trp Gly Glu Ile Lys
    370                 375
```

<210> SEQ ID NO 27
<211> LENGTH: 1125
<212> TYPE: DNA
<213> ORGANISM: artificial
<220> FEATURE:
<223> OTHER INFORMATION: artificial construct

<400> SEQUENCE: 27

```
atgagaggat cgcatcacca tcaccatcac ggatctggct ctggatctgg tatcgaggga      60

aggccttata atggaactgg atccgcatgc gagctcgcaa agaaagatga aaaatcacaa     120

gtatgtagtg gtttggctat ggaaaaatat gacattacaa atttaaatgc taaacaagat     180

aaatcaaaga atgggagcgt gaaagagttg aaacatatct attcaaacca tattaaaggt     240

aacaagatta cagcaccaaa acctagtatt caaggtgtgg tcatccacaa tgattatggt     300

agtatgacac ctagtcaata cttaccatgg ttatatgcac gtgagaataa cggtacacac     360

gttaacggtt gggctagtgt ttatgcaaat agaaacgaag tgctttggta tcatccgaca     420

gactacgtag agtggcattg tggtaatcaa tgggcaaatg ctaacttaat cggatttgaa     480

gtgtgtgagt cgtatcctgg tagaatctcg gacaaattat tcttagaaaa tgaagaagcg     540

acattgaaag tagctgcgga tgtgatgaag tcgtacggat taccagttaa tcgcaacact     600

gtacgtctgc ataacgaatt cttcggaact tcttgtccac atcgttcgtg ggacttgcat     660

gttggcaaag gtgagcctta cacaactact aatattaata aaatgaaaga ctacttcatc     720

aaacgcatca aacattatta tgacggtgga aagctagaag taagcaaagc agcaactatc     780

aaacaatctg acgttaagca agaagttaaa aagcaagaag caaaacaaat tgtgaaagca     840

acagattgga aacaaacaa atatggcaca ctatataaat cagagtcagc tagcttcaca     900

cctaatacag atataataac aagaacgact ggtccattta gaagcatgcc gcagtcagga     960

gtcttaaaag caggtcaaac aattcattat gatgaagtga tgaaacaaga cggtcatgtt    1020

tgggtaggtt atacaggtaa cagtggccaa cgtatttact tgcctgtaag aacatggaat    1080

aaatctacta atactttagg tgttctttgg ggaactataa agtaa                    1125
```

<210> SEQ ID NO 28
<211> LENGTH: 374
<212> TYPE: PRT
<213> ORGANISM: artificial
<220> FEATURE:
<223> OTHER INFORMATION: artificial construct

<400> SEQUENCE: 28

```
Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Ala Lys Lys Asp Glu Lys Ser Gln Val Cys Ser Gly Leu Ala Met Glu
        35                  40                  45

Lys Tyr Asp Ile Thr Asn Leu Asn Ala Lys Gln Asp Lys Ser Lys Asn
    50                  55                  60

Gly Ser Val Lys Glu Leu Lys His Ile Tyr Ser Asn His Ile Lys Gly
65                  70                  75                  80

Asn Lys Ile Thr Ala Pro Lys Pro Ser Ile Gln Gly Val Val Ile His
                85                  90                  95

Asn Asp Tyr Gly Ser Met Thr Pro Ser Gln Tyr Leu Pro Trp Leu Tyr
            100                 105                 110

Ala Arg Glu Asn Asn Gly Thr His Val Asn Gly Trp Ala Ser Val Tyr
        115                 120                 125

Ala Asn Arg Asn Glu Val Leu Trp Tyr His Pro Thr Asp Tyr Val Glu
    130                 135                 140

Trp His Cys Gly Asn Gln Trp Ala Asn Ala Asn Leu Ile Gly Phe Glu
145                 150                 155                 160

Val Cys Glu Ser Tyr Pro Gly Arg Ile Ser Asp Lys Leu Phe Leu Glu
                165                 170                 175

Asn Glu Glu Ala Thr Leu Lys Val Ala Ala Asp Val Met Lys Ser Tyr
            180                 185                 190

Gly Leu Pro Val Asn Arg Asn Thr Val Arg Leu His Asn Glu Phe Phe
        195                 200                 205

Gly Thr Ser Cys Pro His Arg Ser Trp Asp Leu His Val Gly Lys Gly
    210                 215                 220

Glu Pro Tyr Thr Thr Thr Asn Ile Asn Lys Met Lys Asp Tyr Phe Ile
225                 230                 235                 240

Lys Arg Ile Lys His Tyr Tyr Asp Gly Gly Lys Leu Glu Val Ser Lys
                245                 250                 255

Ala Ala Thr Ile Lys Gln Ser Asp Val Lys Gln Glu Val Lys Lys Gln
            260                 265                 270

Glu Ala Lys Gln Ile Val Lys Ala Thr Asp Trp Lys Thr Asn Lys Tyr
        275                 280                 285

Gly Thr Leu Tyr Lys Ser Glu Ser Ala Ser Phe Thr Pro Asn Thr Asp
    290                 295                 300

Ile Ile Thr Arg Thr Thr Gly Pro Phe Arg Ser Met Pro Gln Ser Gly
305                 310                 315                 320

Val Leu Lys Ala Gly Gln Thr Ile His Tyr Asp Glu Val Met Lys Gln
                325                 330                 335

Asp Gly His Val Trp Val Gly Tyr Thr Gly Asn Ser Gly Gln Arg Ile
            340                 345                 350

Tyr Leu Pro Val Arg Thr Trp Asn Lys Ser Thr Asn Thr Leu Gly Val
        355                 360                 365
```

```
Leu Trp Gly Thr Ile Lys
    370

<210> SEQ ID NO 29
<211> LENGTH: 1131
<212> TYPE: DNA
<213> ORGANISM: artificial
<220> FEATURE:
<223> OTHER INFORMATION: artificial construct

<400> SEQUENCE: 29

atgagaggat cgcatcacca tcaccatcac ggatctggct ctggatctgg tatcgaggga     60

aggccttata atggaactgg atccgcatgc gagctcgcaa agaaagatga aaaatcacaa    120

gtatgtagtg gtttggctat ggaaaaatat gacattacaa atttaaatgc taaacaagat    180

aaatcaaaga atgggagcgt gaaagagttg aaacatatct attcaaacca tattaaaggt    240

aacaagatta cagcaccaaa acctagtatt caaggtgtgg tcatccacaa tgattatggt    300

agtatgacac ctagtcaata cttaccatgg ttatatgcac gtgagaataa cggtacacac    360

gttaacggtt gggctagtgt ttatgcaaat agaaacgaag tgctttggta tcatccgaca    420

gactacgtag agtggcattg tggtaatcaa tgggcaaatg ctaacttaat cggatttgaa    480

gtgtgtgagt cgtatcctgg tagaatctcg gacaaattat tcttagaaaa tgaagaagcg    540

acattgaaag tagctgcgga tgtgatgaag tcgtacggat taccagttaa tcgcaacact    600

gtacgtctgc ataacgaatt cttcggaact tcttgtccac atcgttcgtg ggacttgcat    660

gttggcaaag gtgagcctta cacaactact aatattaata aaatgaaaga ctacttcatc    720

aaacgcatca aacattatta tgacggtgga aagctagaag taagcaaagc agcaactatc    780

aaacaatctg acgttaagca agaagttaaa aagcaagaag caaaacaaat tgtgaaagca    840

acagatggta aatctgcaag taaaataaca gttggaagta aagcgcctta taaccttaaa    900

tggtcaaaag gtgcttattt taatgcgaaa atcgacggct taggtgctac ttcagccact    960

agatacggtg ataatcgtac taactataga ttcgatgttg gacaggctgt atacgcgcct   1020

ggaacattaa tatatgtgtt tgaaattata gatggttggt gtcgcattta ttggaacaat   1080

cataatgagt ggatatggca tgagagattg attgtgaaag aagtgtttta a            1131


<210> SEQ ID NO 30
<211> LENGTH: 376
<212> TYPE: PRT
<213> ORGANISM: artificial
<220> FEATURE:
<223> OTHER INFORMATION: artificial construct

<400> SEQUENCE: 30

Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Ala Lys Lys Asp Glu Lys Ser Gln Val Cys Ser Gly Leu Ala Met Glu
        35                  40                  45

Lys Tyr Asp Ile Thr Asn Leu Asn Ala Lys Gln Asp Lys Ser Lys Asn
    50                  55                  60

Gly Ser Val Lys Glu Leu Lys His Ile Tyr Ser Asn His Ile Lys Gly
65                  70                  75                  80

Asn Lys Ile Thr Ala Pro Lys Pro Ser Ile Gln Gly Val Val Ile His
                85                  90                  95
```

```
Asn Asp Tyr Gly Ser Met Thr Pro Ser Gln Tyr Leu Pro Trp Leu Tyr
            100                 105                 110

Ala Arg Glu Asn Asn Gly Thr His Val Asn Gly Trp Ala Ser Val Tyr
        115                 120                 125

Ala Asn Arg Asn Glu Val Leu Trp Tyr His Pro Thr Asp Tyr Val Glu
    130                 135                 140

Trp His Cys Gly Asn Gln Trp Ala Asn Ala Asn Leu Ile Gly Phe Glu
145                 150                 155                 160

Val Cys Glu Ser Tyr Pro Gly Arg Ile Ser Asp Lys Leu Phe Leu Glu
                165                 170                 175

Asn Glu Glu Ala Thr Leu Lys Val Ala Ala Asp Val Met Lys Ser Tyr
            180                 185                 190

Gly Leu Pro Val Asn Arg Asn Thr Val Arg Leu His Asn Glu Phe Phe
        195                 200                 205

Gly Thr Ser Cys Pro His Arg Ser Trp Asp Leu His Val Gly Lys Gly
    210                 215                 220

Glu Pro Tyr Thr Thr Thr Asn Ile Asn Lys Met Lys Asp Tyr Phe Ile
225                 230                 235                 240

Lys Arg Ile Lys His Tyr Tyr Asp Gly Gly Lys Leu Glu Val Ser Lys
                245                 250                 255

Ala Ala Thr Ile Lys Gln Ser Asp Val Lys Gln Glu Val Lys Lys Gln
            260                 265                 270

Glu Ala Lys Gln Ile Val Lys Ala Thr Asp Gly Lys Ser Ala Ser Lys
        275                 280                 285

Ile Thr Val Gly Ser Lys Ala Pro Tyr Asn Leu Lys Trp Ser Lys Gly
    290                 295                 300

Ala Tyr Phe Asn Ala Lys Ile Asp Gly Leu Gly Ala Thr Ser Ala Thr
305                 310                 315                 320

Arg Tyr Gly Asp Asn Arg Thr Asn Tyr Arg Phe Asp Val Gly Gln Ala
                325                 330                 335

Val Tyr Ala Pro Gly Thr Leu Ile Tyr Val Phe Glu Ile Ile Asp Gly
            340                 345                 350

Trp Cys Arg Ile Tyr Trp Asn Asn His Asn Glu Trp Ile Trp His Glu
        355                 360                 365

Arg Leu Ile Val Lys Glu Val Phe
    370                 375
```

<210> SEQ ID NO 31
<211> LENGTH: 975
<212> TYPE: DNA
<213> ORGANISM: artificial
<220> FEATURE:
<223> OTHER INFORMATION: artificial construct

<400> SEQUENCE: 31

```
atgagaggat cgcatcacca tcaccatcac ggatctggct ctggatctgg tatcgaggga      60

aggccttata atggaactgg atccgcatgc gagctcatgg ctaagactca agcagaaata     120

aataaacgtt tagatgctta tgcaaaagga acagtagata gcccttacag agttaaaaaa     180

gctacaagtt atgacccatc atttggtgta atggaagcag gagccattga tgcagatggt     240

tactatcacg ctcagtgtca agaccttatt acagactatg ttttatggtt aacagataat     300

aaagttagaa cttggggtaa tgctaaagac caaattaaac agagttatgg tactggattt     360

aaaatacatg aaaataaacc ttctactgta cctaaaaaag gttggattgc ggtatttaca     420

tccggtagtt atgaacagtg ggtcacata ggtattgtat atgatggagg taatacttct     480
```

```
acatttacta ttttagagca aaactggaat ggttatgcta ataaaaaacc tacaaaacgt    540

gtagataatt attacggatt aactcacttc attgaaatac ctgtaaaagc aggaaagcta    600

gaagtaagca aagcagcaac tatcaaacaa tctgacgtta agcaagaagt taaaaagcaa    660

gaagcaaaac aaattgtgaa agcaacagat tggaaacaga ataaagatgg catttggtat    720

aaagctgaac atgcttcgtt cacagtgaca gcaccagagg gaattatcac aagatacaaa    780

ggtccttgga ctggtcaccc acaagctggt gtattacaaa aaggtcaaac gattaaatat    840

gatgaggttc aaaaatttga cggtcatgtt tgggtatcgt gggaaacgtt tgagggcgaa    900

actgtataca tgccggtacg cacatgggac gctaaaactg gtaaagttgg taagttgtgg    960

ggcgaaatta aataa                                                      975
```

<210> SEQ ID NO 32
<211> LENGTH: 324
<212> TYPE: PRT
<213> ORGANISM: artificial
<220> FEATURE:
<223> OTHER INFORMATION: artificial construct

<400> SEQUENCE: 32

```
Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Met Ala Lys Thr Gln Ala Glu Ile Asn Lys Arg Leu Asp Ala Tyr Ala
        35                  40                  45

Lys Gly Thr Val Asp Ser Pro Tyr Arg Val Lys Lys Ala Thr Ser Tyr
    50                  55                  60

Asp Pro Ser Phe Gly Val Met Glu Ala Gly Ala Ile Asp Ala Asp Gly
65                  70                  75                  80

Tyr Tyr His Ala Gln Cys Gln Asp Leu Ile Thr Asp Tyr Val Leu Trp
                85                  90                  95

Leu Thr Asp Asn Lys Val Arg Thr Trp Gly Asn Ala Lys Asp Gln Ile
            100                 105                 110

Lys Gln Ser Tyr Gly Thr Gly Phe Lys Ile His Glu Asn Lys Pro Ser
        115                 120                 125

Thr Val Pro Lys Lys Gly Trp Ile Ala Val Phe Thr Ser Gly Ser Tyr
    130                 135                 140

Glu Gln Trp Gly His Ile Gly Ile Val Tyr Asp Gly Gly Asn Thr Ser
145                 150                 155                 160

Thr Phe Thr Ile Leu Glu Gln Asn Trp Asn Gly Tyr Ala Asn Lys Lys
                165                 170                 175

Pro Thr Lys Arg Val Asp Asn Tyr Tyr Gly Leu Thr His Phe Ile Glu
            180                 185                 190

Ile Pro Val Lys Ala Gly Lys Leu Glu Val Ser Lys Ala Ala Thr Ile
        195                 200                 205

Lys Gln Ser Asp Val Lys Gln Glu Val Lys Lys Gln Glu Ala Lys Gln
    210                 215                 220

Ile Val Lys Ala Thr Asp Trp Lys Gln Asn Lys Asp Gly Ile Trp Tyr
225                 230                 235                 240

Lys Ala Glu His Ala Ser Phe Thr Val Thr Ala Pro Glu Gly Ile Ile
                245                 250                 255

Thr Arg Tyr Lys Gly Pro Trp Thr Gly His Pro Gln Ala Gly Val Leu
            260                 265                 270
```

```
Gln Lys Gly Gln Thr Ile Lys Tyr Asp Glu Val Gln Lys Phe Asp Gly
        275                 280                 285

His Val Trp Val Ser Trp Glu Thr Phe Glu Gly Glu Thr Val Tyr Met
    290                 295                 300

Pro Val Arg Thr Trp Asp Ala Lys Thr Gly Lys Val Gly Lys Leu Trp
305                 310                 315                 320

Gly Glu Ile Lys


<210> SEQ ID NO 33
<211> LENGTH: 912
<212> TYPE: DNA
<213> ORGANISM: artificial
<220> FEATURE:
<223> OTHER INFORMATION: artificial construct

<400> SEQUENCE: 33

atgagaggat cgcatcacca tcaccatcac ggatctggct ctggatctgg tatcgaggga     60

aggccttata atggaactgg atccgcatgc gagctcatgg ctaagactca agcagaaata    120

aataaacgtt tagatgctta tgcaaaagga acagtagata gcccttacag agttaaaaaa    180

gctacaagtt atgacccatc atttggtgta atggaagcag gagccattga tgcagatggt    240

tactatcacg ctcagtgtca agaccttatt acagactatg ttttatggtt aacagataat    300

aaagttagaa cttggggtaa tgctaaagac caaattaaac agagttatgg tactggattt    360

aaaatacatg aaaataaacc ttctactgta cctaaaaaag gttggattgc ggtatttaca    420

tccggtagtt atgaacagtg ggggtcacata ggtattgtat atgatggagg taatacttct    480

acatttacta ttttagagca aaactggaat ggttatgcta ataaaaaacc tacaaaacgt    540

gtagataatt attacggatt aactcacttc attgaaatac ctgtaaaagc aggaaaagca    600

ggtggtacag taactccaac gccgaataca ggttggaaaa caaacaaata tggcacacta    660

tataaatcag agtcagctag cttcacacct aatacagata taataacaag aacgactggt    720

ccatttagaa gcatgccgca gtcaggagtc ttaaaagcag gtcaaacaat tcattatgat    780

gaagtgatga aacaagacgg tcatgtttgg gtaggttata caggtaacag tggccaacgt    840

atttacttgc ctgtaagaac atggaataaa tctactaata ctttaggtgt tctttgggga    900

actataaagt aa                                                        912


<210> SEQ ID NO 34
<211> LENGTH: 303
<212> TYPE: PRT
<213> ORGANISM: artificial
<220> FEATURE:
<223> OTHER INFORMATION: artificial construct

<400> SEQUENCE: 34

Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Met Ala Lys Thr Gln Ala Glu Ile Asn Lys Arg Leu Asp Ala Tyr Ala
        35                  40                  45

Lys Gly Thr Val Asp Ser Pro Tyr Arg Val Lys Lys Ala Thr Ser Tyr
    50                  55                  60

Asp Pro Ser Phe Gly Val Met Glu Ala Gly Ala Ile Asp Ala Asp Gly
65                  70                  75                  80
```

```
Tyr Tyr His Ala Gln Cys Gln Asp Leu Ile Thr Asp Tyr Val Leu Trp
                85                  90                  95

Leu Thr Asp Asn Lys Val Arg Thr Trp Gly Asn Ala Lys Asp Gln Ile
            100                 105                 110

Lys Gln Ser Tyr Gly Thr Gly Phe Lys Ile His Glu Asn Lys Pro Ser
        115                 120                 125

Thr Val Pro Lys Lys Gly Trp Ile Ala Val Phe Thr Ser Gly Ser Tyr
    130                 135                 140

Glu Gln Trp Gly His Ile Gly Ile Val Tyr Asp Gly Gly Asn Thr Ser
145                 150                 155                 160

Thr Phe Thr Ile Leu Glu Gln Asn Trp Asn Gly Tyr Ala Asn Lys Lys
                165                 170                 175

Pro Thr Lys Arg Val Asp Asn Tyr Tyr Gly Leu Thr His Phe Ile Glu
            180                 185                 190

Ile Pro Val Lys Ala Gly Lys Ala Gly Gly Thr Val Thr Pro Thr Pro
        195                 200                 205

Asn Thr Gly Trp Lys Thr Asn Lys Tyr Gly Thr Leu Tyr Lys Ser Glu
    210                 215                 220

Ser Ala Ser Phe Thr Pro Asn Thr Asp Ile Ile Thr Arg Thr Thr Gly
225                 230                 235                 240

Pro Phe Arg Ser Met Pro Gln Ser Gly Val Leu Lys Ala Gly Gln Thr
                245                 250                 255

Ile His Tyr Asp Glu Val Met Lys Gln Asp Gly His Val Trp Val Gly
            260                 265                 270

Tyr Thr Gly Asn Ser Gly Gln Arg Ile Tyr Leu Pro Val Arg Thr Trp
        275                 280                 285

Asn Lys Ser Thr Asn Thr Leu Gly Val Leu Trp Gly Thr Ile Lys
    290                 295                 300
```

<210> SEQ ID NO 35
<211> LENGTH: 966
<212> TYPE: DNA
<213> ORGANISM: artificial
<220> FEATURE:
<223> OTHER INFORMATION: artificial construct

<400> SEQUENCE: 35

```
atgagaggat cgcatcacca tcaccatcac ggatctggct ctggatctgg tatcgaggga     60

aggccttata atggaactgg atccgcatgc gagctcatgg ctaagactca agcagaaata    120

aataaacgtt tagatgctta tgcaaaagga acagtagata gcccttacag agttaaaaaa    180

gctacaagtt atgacccatc atttggtgta atggaagcag gagccattga tgcagatggt    240

tactatcacg ctcagtgtca agaccttatt acagactatg ttttatggtt aacagataat    300

aaagttagaa cttggggtaa tgctaaagac caaattaaac agagttatgg tactggattt    360

aaaatacatg aaaataaacc ttctactgta cctaaaaaag gttggattgc ggtatttaca    420

tccggtagtt atgaacagtg ggtcacata ggtattgtat atgatggagg taatacttct     480

acatttacta ttttagagca aaactggaat ggttatgcta ataaaaaacc tacaaaacgt    540

gtagataatt attacggatt aactcacttc attgaaatac ctgtaaaagc aggaactact    600

gttaaaaaag aaacagctaa gaaaagcgca agtaaaacgc ctgcacctaa aaagaaagca    660

acactaaaag tttctaagaa tggtaaatct gcaagtaaaa taacagttgg aagtaaagcg    720

ccttataacc ttaaatggtc aaaaggtgct tattttaatg cgaaaatcga cggcttaggt    780

gctacttcag ccactagata cggtgataat cgtactaact atagattcga tgttggacag    840
```

```
gctgtatacg cgcctggaac attaatatat gtgtttgaaa ttatagatgg ttggtgtcgc    900

atttattgga acaatcataa tgagtggata tggcatgaga gattgattgt gaaagaagtg    960

ttttaa                                                               966


<210> SEQ ID NO 36
<211> LENGTH: 321
<212> TYPE: PRT
<213> ORGANISM: artificial
<220> FEATURE:
<223> OTHER INFORMATION: artificial construct

<400> SEQUENCE: 36

Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Met Ala Lys Thr Gln Ala Glu Ile Asn Lys Arg Leu Asp Ala Tyr Ala
        35                  40                  45

Lys Gly Thr Val Asp Ser Pro Tyr Arg Val Lys Lys Ala Thr Ser Tyr
    50                  55                  60

Asp Pro Ser Phe Gly Val Met Glu Ala Gly Ala Ile Asp Ala Asp Gly
65                  70                  75                  80

Tyr Tyr His Ala Gln Cys Gln Asp Leu Ile Thr Asp Tyr Val Leu Trp
                85                  90                  95

Leu Thr Asp Asn Lys Val Arg Thr Trp Gly Asn Ala Lys Asp Gln Ile
            100                 105                 110

Lys Gln Ser Tyr Gly Thr Gly Phe Lys Ile His Glu Asn Lys Pro Ser
        115                 120                 125

Thr Val Pro Lys Lys Gly Trp Ile Ala Val Phe Thr Ser Gly Ser Tyr
    130                 135                 140

Glu Gln Trp Gly His Ile Gly Ile Val Tyr Asp Gly Gly Asn Thr Ser
145                 150                 155                 160

Thr Phe Thr Ile Leu Glu Gln Asn Trp Asn Gly Tyr Ala Asn Lys Lys
                165                 170                 175

Pro Thr Lys Arg Val Asp Asn Tyr Tyr Gly Leu Thr His Phe Ile Glu
            180                 185                 190

Ile Pro Val Lys Ala Gly Thr Thr Val Lys Lys Glu Thr Ala Lys Lys
        195                 200                 205

Ser Ala Ser Lys Thr Pro Ala Pro Lys Lys Lys Ala Thr Leu Lys Val
    210                 215                 220

Ser Lys Asn Gly Lys Ser Ala Ser Lys Ile Thr Val Gly Ser Lys Ala
225                 230                 235                 240

Pro Tyr Asn Leu Lys Trp Ser Lys Gly Ala Tyr Phe Asn Ala Lys Ile
                245                 250                 255

Asp Gly Leu Gly Ala Thr Ser Ala Thr Arg Tyr Gly Asp Asn Arg Thr
            260                 265                 270

Asn Tyr Arg Phe Asp Val Gly Gln Ala Val Tyr Ala Pro Gly Thr Leu
        275                 280                 285

Ile Tyr Val Phe Glu Ile Ile Asp Gly Trp Cys Arg Ile Tyr Trp Asn
    290                 295                 300

Asn His Asn Glu Trp Ile Trp His Glu Arg Leu Ile Val Lys Glu Val
305                 310                 315                 320

Phe
```

<210> SEQ ID NO 37
<211> LENGTH: 927
<212> TYPE: DNA
<213> ORGANISM: artificial
<220> FEATURE:
<223> OTHER INFORMATION: artificial construct

<400> SEQUENCE: 37

```
atgagaggat cgcatcacca tcaccatcac ggatctggct ctggatctgg tatcgaggga     60

aggccttata atggaactgg atccgcatgc gagctcatga aaccctgaa acaagcagag    120

tcctacatta agagtaaagt aaatacagga actgattttg atggtttata tgggtatcag    180

tgtatggact tagcagtaga ttatatttac catgtaacag atggtaaaat aagaatgtgg    240

ggtaatgcta aggatgcgat aaataactct tttggtggta ctgctacggt atataaaaac    300

taccctgctt ttagacctaa gtacggtgat gtagtcgtat ggactactgg taattttgca    360

acttatggtc atatcgcaat agttactaac cctgaccctt atggagacct tcaatatgtt    420

acagttcttg aacaaaactg gaacggtaac gggatttata aaaccgagtt agctacaatc    480

agaacacacg attacacagg aattacacat tttattagac ctaactttgc tactgaatca    540

agtgtaaaaa agaaagatac aaagaaaaaa ccaaaaccat caaatagaga tggaataaat    600

aaagataaaa ttgtatatga tagaactaat attaattaca attggaaaca gaataaagat    660

ggcatttggt ataaagctga acatgcttcg ttcacagtga cagcaccaga gggaattatc    720

acaagataca aaggtccttg gactggtcac ccacaagctg gtgtattaca aaaaggtcaa    780

acgattaaat atgatgaggt tcaaaaattt gacggtcatg tttgggtatc gtgggaaacg    840

tttgagggcg aaactgtata catgccggta cgcacatggg acgctaaaac tggtaaagtt    900

ggtaagttgt ggggcgaaat taaataa                                      927
```

<210> SEQ ID NO 38
<211> LENGTH: 308
<212> TYPE: PRT
<213> ORGANISM: artificial
<220> FEATURE:
<223> OTHER INFORMATION: artificial construct

<400> SEQUENCE: 38

```
Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Met Lys Thr Leu Lys Gln Ala Glu Ser Tyr Ile Lys Ser Lys Val Asn
        35                  40                  45

Thr Gly Thr Asp Phe Asp Gly Leu Tyr Gly Tyr Gln Cys Met Asp Leu
    50                  55                  60

Ala Val Asp Tyr Ile Tyr His Val Thr Asp Gly Lys Ile Arg Met Trp
65                  70                  75                  80

Gly Asn Ala Lys Asp Ala Ile Asn Asn Ser Phe Gly Gly Thr Ala Thr
                85                  90                  95

Val Tyr Lys Asn Tyr Pro Ala Phe Arg Pro Lys Tyr Gly Asp Val Val
            100                 105                 110

Val Trp Thr Thr Gly Asn Phe Ala Thr Tyr Gly His Ile Ala Ile Val
        115                 120                 125

Thr Asn Pro Asp Pro Tyr Gly Asp Leu Gln Tyr Val Thr Val Leu Glu
    130                 135                 140
```

```
Gln Asn Trp Asn Gly Asn Gly Ile Tyr Lys Thr Glu Leu Ala Thr Ile
145                 150                 155                 160

Arg Thr His Asp Tyr Thr Gly Ile Thr His Phe Ile Arg Pro Asn Phe
                165                 170                 175

Ala Thr Glu Ser Ser Val Lys Lys Lys Asp Thr Lys Lys Lys Pro Lys
            180                 185                 190

Pro Ser Asn Arg Asp Gly Ile Asn Lys Asp Lys Ile Val Tyr Asp Arg
        195                 200                 205

Thr Asn Ile Asn Tyr Asn Trp Lys Gln Asn Lys Asp Gly Ile Trp Tyr
    210                 215                 220

Lys Ala Glu His Ala Ser Phe Thr Val Thr Ala Pro Glu Gly Ile Ile
225                 230                 235                 240

Thr Arg Tyr Lys Gly Pro Trp Thr Gly His Pro Gln Ala Gly Val Leu
                245                 250                 255

Gln Lys Gly Gln Thr Ile Lys Tyr Asp Glu Val Gln Lys Phe Asp Gly
            260                 265                 270

His Val Trp Val Ser Trp Glu Thr Phe Glu Gly Glu Thr Val Tyr Met
        275                 280                 285

Pro Val Arg Thr Trp Asp Ala Lys Thr Gly Lys Val Gly Lys Leu Trp
    290                 295                 300

Gly Glu Ile Lys
305
```

<210> SEQ ID NO 39
<211> LENGTH: 921
<212> TYPE: DNA
<213> ORGANISM: artificial
<220> FEATURE:
<223> OTHER INFORMATION: artificial construct

<400> SEQUENCE: 39

```
atgagaggat cgcatcacca tcaccatcac ggatctggct ctggatctgg tatcgaggga     60

aggccttata atggaactgg atccgcatgc gagctcatga aaaccctgaa acaagcagag    120

tcctacatta agagtaaagt aaatacagga actgattttg atggtttata tgggtatcag    180

tgtatggact tagcagtaga ttatatttac catgtaacag atggtaaaat aagaatgtgg    240

ggtaatgcta aggatgcgat aaataactct tttggtggta ctgctacggt atataaaaac    300

taccctgctt ttagacctaa gtacggtgat gtagtcgtat ggactactgg taattttgca    360

acttatggtc atatcgcaat agttactaac cctgaccctt atggagacct tcaatatgtt    420

acagttcttg aacaaaactg gaacggtaac gggatttata aaaccgagtt agctacaatc    480

agaacacacg attacacagg aattacacat tttattagac ctaactttgc tactgaatca    540

agtgtaaaaa agaaagatac aaagaaaaaa ccaaaaccat caaatagaga tggaataaat    600

aaagataaaa ttgtatatga tagaactaat attaattaca attggaaaac aaacaaatat    660

ggcacactat ataaatcaga gtcagctagc ttcacaccta atacagatat aataacaaga    720

acgactggtc catttagaag catgccgcag tcaggagtct taaaagcagg tcaaacaatt    780

cattatgatg aagtgatgaa acaagacggt catgtttggg taggttatac aggtaacagt    840

ggccaacgta tttacttgcc tgtaagaaca tggaataaat ctactaatac tttaggtgtt    900

ctttggggaa ctataaagta a                                               921
```

<210> SEQ ID NO 40
<211> LENGTH: 306
<212> TYPE: PRT

```
<213> ORGANISM: artificial
<220> FEATURE:
<223> OTHER INFORMATION: artificial construct

<400> SEQUENCE: 40

Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Met Lys Thr Leu Lys Gln Ala Glu Ser Tyr Ile Lys Ser Lys Val Asn
        35                  40                  45

Thr Gly Thr Asp Phe Asp Gly Leu Tyr Gly Tyr Gln Cys Met Asp Leu
    50                  55                  60

Ala Val Asp Tyr Ile Tyr His Val Thr Asp Gly Lys Ile Arg Met Trp
65                  70                  75                  80

Gly Asn Ala Lys Asp Ala Ile Asn Asn Ser Phe Gly Gly Thr Ala Thr
                85                  90                  95

Val Tyr Lys Asn Tyr Pro Ala Phe Arg Pro Lys Tyr Gly Asp Val Val
            100                 105                 110

Val Trp Thr Thr Gly Asn Phe Ala Thr Tyr Gly His Ile Ala Ile Val
        115                 120                 125

Thr Asn Pro Asp Pro Tyr Gly Asp Leu Gln Tyr Val Thr Val Leu Glu
    130                 135                 140

Gln Asn Trp Asn Gly Asn Gly Ile Tyr Lys Thr Glu Leu Ala Thr Ile
145                 150                 155                 160

Arg Thr His Asp Tyr Thr Gly Ile Thr His Phe Ile Arg Pro Asn Phe
                165                 170                 175

Ala Thr Glu Ser Ser Val Lys Lys Lys Asp Thr Lys Lys Lys Pro Lys
            180                 185                 190

Pro Ser Asn Arg Asp Gly Ile Asn Lys Asp Lys Ile Val Tyr Asp Arg
        195                 200                 205

Thr Asn Ile Asn Tyr Asn Trp Lys Thr Asn Lys Tyr Gly Thr Leu Tyr
    210                 215                 220

Lys Ser Glu Ser Ala Ser Phe Thr Pro Asn Thr Asp Ile Ile Thr Arg
225                 230                 235                 240

Thr Thr Gly Pro Phe Arg Ser Met Pro Gln Ser Gly Val Leu Lys Ala
                245                 250                 255

Gly Gln Thr Ile His Tyr Asp Glu Val Met Lys Gln Asp Gly His Val
            260                 265                 270

Trp Val Gly Tyr Thr Gly Asn Ser Gly Gln Arg Ile Tyr Leu Pro Val
        275                 280                 285

Arg Thr Trp Asn Lys Ser Thr Asn Thr Leu Gly Val Leu Trp Gly Thr
    290                 295                 300

Ile Lys
305


<210> SEQ ID NO 41
<211> LENGTH: 927
<212> TYPE: DNA
<213> ORGANISM: artificial
<220> FEATURE:
<223> OTHER INFORMATION: artificial construct

<400> SEQUENCE: 41

atgagaggat cgcatcacca tcaccatcac ggatctggct ctggatctgg tatcgaggga      60

aggccttata atggaactgg atccgcatgc gagctcatga aaaccctgaa acaagcagag     120
```

```
tcctacatta agagtaaagt aaatacagga actgattttg atggtttata tgggtatcag    180

tgtatggact tagcagtaga ttatatttac catgtaacag atggtaaaat aagaatgtgg    240

ggtaatgcta aggatgcgat aaataactct tttggtggta ctgctacggt atataaaaac    300

taccctgctt ttagacctaa gtacggtgat gtagtcgtat ggactactgg taattttgca    360

acttatggtc atatcgcaat agttactaac cctgaccctt atggagacct tcaatatgtt    420

acagttcttg aacaaaactg gaacggtaac gggatttata aaaccgagtt agctacaatc    480

agaacacacg attacacagg aattacacat tttattagac ctaactttgc tactgaatca    540

agtgtaaaaa agaaagatac aaagaaaaaa ccaaaaccat caaatagaga tggaataaat    600

aaagataaaa ttgtatatga tagaactaat attaattaca atggtaaatc tgcaagtaaa    660

ataacagttg gaagtaaagc gccttataac cttaaatggt caaaaggtgc ttattttaat    720

gcgaaaatcg acggcttagg tgctacttca gccactagat acggtgataa tcgtactaac    780

tatagattcg atgttggaca ggctgtatac gcgcctggaa cattaatata tgtgtttgaa    840

attatagatg gttggtgtcg catttattgg aacaatcata atgagtggat atggcatgag    900

agattgattg tgaaagaagt gttttaa                                        927
```

<210> SEQ ID NO 42
<211> LENGTH: 308
<212> TYPE: PRT
<213> ORGANISM: artificial
<220> FEATURE:
<223> OTHER INFORMATION: artificial construct

<400> SEQUENCE: 42

```
Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Met Lys Thr Leu Lys Gln Ala Glu Ser Tyr Ile Lys Ser Lys Val Asn
        35                  40                  45

Thr Gly Thr Asp Phe Asp Gly Leu Tyr Gly Tyr Gln Cys Met Asp Leu
    50                  55                  60

Ala Val Asp Tyr Ile Tyr His Val Thr Asp Gly Lys Ile Arg Met Trp
65                  70                  75                  80

Gly Asn Ala Lys Asp Ala Ile Asn Asn Ser Phe Gly Gly Thr Ala Thr
                85                  90                  95

Val Tyr Lys Asn Tyr Pro Ala Phe Arg Pro Lys Tyr Gly Asp Val Val
            100                 105                 110

Val Trp Thr Thr Gly Asn Phe Ala Thr Tyr Gly His Ile Ala Ile Val
        115                 120                 125

Thr Asn Pro Asp Pro Tyr Gly Asp Leu Gln Tyr Val Thr Val Leu Glu
    130                 135                 140

Gln Asn Trp Asn Gly Asn Gly Ile Tyr Lys Thr Glu Leu Ala Thr Ile
145                 150                 155                 160

Arg Thr His Asp Tyr Thr Gly Ile Thr His Phe Ile Arg Pro Asn Phe
                165                 170                 175

Ala Thr Glu Ser Ser Val Lys Lys Lys Asp Thr Lys Lys Lys Pro Lys
            180                 185                 190

Pro Ser Asn Arg Asp Gly Ile Asn Lys Asp Lys Ile Val Tyr Asp Arg
        195                 200                 205

Thr Asn Ile Asn Tyr Asn Gly Lys Ser Ala Ser Lys Ile Thr Val Gly
```

```
    210                 215                 220

Ser Lys Ala Pro Tyr Asn Leu Lys Trp Ser Lys Gly Ala Tyr Phe Asn
225                 230                 235                 240

Ala Lys Ile Asp Gly Leu Gly Ala Thr Ser Ala Thr Arg Tyr Gly Asp
                245                 250                 255

Asn Arg Thr Asn Tyr Arg Phe Asp Val Gly Gln Ala Val Tyr Ala Pro
            260                 265                 270

Gly Thr Leu Ile Tyr Val Phe Glu Ile Ile Asp Gly Trp Cys Arg Ile
        275                 280                 285

Tyr Trp Asn Asn His Asn Glu Trp Ile Trp His Glu Arg Leu Ile Val
    290                 295                 300

Lys Glu Val Phe
305
```

<210> SEQ ID NO 43
<211> LENGTH: 843
<212> TYPE: DNA
<213> ORGANISM: artificial
<220> FEATURE:
<223> OTHER INFORMATION: artificial construct

<400> SEQUENCE: 43

```
atgagaggat cgcatcacca tcaccatcac ggatctggct ctggatctgg tatcgaggga      60

aggccttata atggaactgg atccgcatgc gagctcgctg caacacatga acattcagca     120

caatggttga ataattacaa aaaaggatat ggttacggtc cttatccatt aggtataaat     180

ggcggtatgc actacggagt tgattttttt atgaatattg gaacaccagt aaaagctatt     240

tcaagcggaa aaatagttga agctggttgg agtaattacg gaggaggtaa tcaaataggt     300

cttattgaaa atgatggagt gcatagacaa tggtatatgc atctaagtaa atataatgtt     360

aaagtaggag attatgtcaa agctggtcaa ataatcggtt ggtctggaag cactggttat     420

tctacagcac cacatttaca cttccaaaga atggttaatt cattttcaaa ttcaactgcc     480

caagatccaa tgcctttctt aaagagcgca ggatatggaa aagcaggtgg tacagtaact     540

ccaacgccga atacaggttg gaaacagaat aaagatggca tttggtataa agctgaacat     600

gcttcgttca cagtgacagc accagaggga attatcacaa gatacaaagg tccttggact     660

ggtcacccac aagctggtgt attacaaaaa ggtcaaacga ttaaatatga tgaggttcaa     720

aaatttgacg gtcatgtttg ggtatcgtgg gaaacgtttg agggcgaaac tgtatacatg     780

ccggtacgca catgggacgc taaaactggt aaagttggta agttgtgggg cgaaattaaa     840

taa                                                                   843
```

<210> SEQ ID NO 44
<211> LENGTH: 280
<212> TYPE: PRT
<213> ORGANISM: artificial
<220> FEATURE:
<223> OTHER INFORMATION: artificial construct

<400> SEQUENCE: 44

```
Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Ala Ala Thr His Glu His Ser Ala Gln Trp Leu Asn Asn Tyr Lys Lys
        35                  40                  45
```

```
Gly Tyr Gly Tyr Gly Pro Tyr Pro Leu Gly Ile Asn Gly Gly Met His
    50                  55                  60

Tyr Gly Val Asp Phe Phe Met Asn Ile Gly Thr Pro Val Lys Ala Ile
65                  70                  75                  80

Ser Ser Gly Lys Ile Val Glu Ala Gly Trp Ser Asn Tyr Gly Gly Gly
                85                  90                  95

Asn Gln Ile Gly Leu Ile Glu Asn Asp Gly Val His Arg Gln Trp Tyr
            100                 105                 110

Met His Leu Ser Lys Tyr Asn Val Lys Val Gly Asp Tyr Val Lys Ala
        115                 120                 125

Gly Gln Ile Ile Gly Trp Ser Gly Ser Thr Gly Tyr Ser Thr Ala Pro
    130                 135                 140

His Leu His Phe Gln Arg Met Val Asn Ser Phe Ser Asn Ser Thr Ala
145                 150                 155                 160

Gln Asp Pro Met Pro Phe Leu Lys Ser Ala Gly Tyr Gly Lys Ala Gly
                165                 170                 175

Gly Thr Val Thr Pro Thr Pro Asn Thr Gly Trp Lys Gln Asn Lys Asp
            180                 185                 190

Gly Ile Trp Tyr Lys Ala Glu His Ala Ser Phe Thr Val Thr Ala Pro
        195                 200                 205

Glu Gly Ile Ile Thr Arg Tyr Lys Gly Pro Trp Thr Gly His Pro Gln
    210                 215                 220

Ala Gly Val Leu Gln Lys Gly Gln Thr Ile Lys Tyr Asp Glu Val Gln
225                 230                 235                 240

Lys Phe Asp Gly His Val Trp Val Ser Trp Glu Thr Phe Glu Gly Glu
                245                 250                 255

Thr Val Tyr Met Pro Val Arg Thr Trp Asp Ala Lys Thr Gly Lys Val
            260                 265                 270

Gly Lys Leu Trp Gly Glu Ile Lys
        275                 280
```

<210> SEQ ID NO 45
<211> LENGTH: 837
<212> TYPE: DNA
<213> ORGANISM: artificial
<220> FEATURE:
<223> OTHER INFORMATION: artificial construct

<400> SEQUENCE: 45

```
atgagaggat cgcatcacca tcaccatcac ggatctggct ctggatctgg tatcgaggga     60

aggccttata atggaactgg atccgcatgc gagctcgctg caacacatga acattcagca    120

caatggttga ataattacaa aaaaggatat ggttacggtc cttatccatt aggtataaat    180

ggcggtatgc actacggagt tgattttttt atgaatattg gaacaccagt aaaagctatt    240

tcaagcggaa aaatagttga agctggttgg agtaattacg gaggaggtaa tcaaataggt    300

cttattgaaa atgatggagt gcatagacaa tggtatatgc atctaagtaa atataatgtt    360

aaagtaggag attatgtcaa agctggtcaa ataatcggtt ggtctggaag cactggttat    420

tctacagcac cacatttaca cttccaaaga atggttaatt cattttcaaa ttcaactgcc    480

caagatccaa tgcctttctt aaagagcgca ggatatggaa aagcaggtgg tacagtaact    540

ccaacgccga atacaggttg gaaaacaaac aaatatggca cactatataa atcagagtca    600

gctagcttca cacctaatac agatataata acaagaacga ctggtccatt tagaagcatg    660

ccgcagtcag gagtcttaaa agcaggtcaa acaattcatt atgatgaagt gatgaaacaa    720
```

```
gacggtcatg tttgggtagg ttatacaggt aacagtggcc aacgtattta cttgcctgta    780

agaacatgga ataaatctac taatacttta ggtgttcttt ggggaactat aaagtaa       837
```

<210> SEQ ID NO 46
<211> LENGTH: 278
<212> TYPE: PRT
<213> ORGANISM: artificial
<220> FEATURE:
<223> OTHER INFORMATION: artificial construct

<400> SEQUENCE: 46

```
Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Ala Ala Thr His Glu His Ser Ala Gln Trp Leu Asn Asn Tyr Lys Lys
        35                  40                  45

Gly Tyr Gly Tyr Gly Pro Tyr Pro Leu Gly Ile Asn Gly Gly Met His
    50                  55                  60

Tyr Gly Val Asp Phe Phe Met Asn Ile Gly Thr Pro Val Lys Ala Ile
65                  70                  75                  80

Ser Ser Gly Lys Ile Val Glu Ala Gly Trp Ser Asn Tyr Gly Gly Gly
                85                  90                  95

Asn Gln Ile Gly Leu Ile Glu Asn Asp Gly Val His Arg Gln Trp Tyr
            100                 105                 110

Met His Leu Ser Lys Tyr Asn Val Lys Val Gly Asp Tyr Val Lys Ala
        115                 120                 125

Gly Gln Ile Ile Gly Trp Ser Gly Ser Thr Gly Tyr Ser Thr Ala Pro
    130                 135                 140

His Leu His Phe Gln Arg Met Val Asn Ser Phe Ser Asn Ser Thr Ala
145                 150                 155                 160

Gln Asp Pro Met Pro Phe Leu Lys Ser Ala Gly Tyr Gly Lys Ala Gly
                165                 170                 175

Gly Thr Val Thr Pro Thr Pro Asn Thr Gly Trp Lys Thr Asn Lys Tyr
            180                 185                 190

Gly Thr Leu Tyr Lys Ser Glu Ser Ala Ser Phe Thr Pro Asn Thr Asp
        195                 200                 205

Ile Ile Thr Arg Thr Thr Gly Pro Phe Arg Ser Met Pro Gln Ser Gly
    210                 215                 220

Val Leu Lys Ala Gly Gln Thr Ile His Tyr Asp Glu Val Met Lys Gln
225                 230                 235                 240

Asp Gly His Val Trp Val Gly Tyr Thr Gly Asn Ser Gly Gln Arg Ile
                245                 250                 255

Tyr Leu Pro Val Arg Thr Trp Asn Lys Ser Thr Asn Thr Leu Gly Val
            260                 265                 270

Leu Trp Gly Thr Ile Lys
        275
```

<210> SEQ ID NO 47
<211> LENGTH: 843
<212> TYPE: DNA
<213> ORGANISM: artificial
<220> FEATURE:
<223> OTHER INFORMATION: artificial construct

<400> SEQUENCE: 47

```
atgagaggat cgcatcacca tcaccatcac ggatctggct ctggatctgg tatcgaggga     60
```

```
aggccttata atggaactgg atccgcatgc gagctcgctg caacacatga acattcagca    120

caatggttga ataattacaa aaaaggatat ggttacggtc cttatccatt aggtataaat    180

ggcggtatgc actacggagt tgattttttt atgaatattg gaacaccagt aaaagctatt    240

tcaagcggaa aaatagttga agctggttgg agtaattacg gaggaggtaa tcaaataggt    300

cttattgaaa atgatggagt gcatagacaa tggtatatgc atctaagtaa atataatgtt    360

aaagtaggag attatgtcaa agctggtcaa ataatcggtt ggtctggaag cactggttat    420

tctacagcac cacatttaca cttccaaaga atggttaatt cattttcaaa ttcaactgcc    480

caagatccaa tgcctttctt aaagagcgca ggatatggaa aagcaggtgg tacagtaact    540

ccaacgccga atacaggtgg taaatctgca agtaaaataa cagttggaag taaagcgcct    600

tataacctta aatggtcaaa aggtgcttat tttaatgcga aaatcgacgg cttaggtgct    660

acttcagcca ctagatacgg tgataatcgt actaactata gattcgatgt tggacaggct    720

gtatacgcgc ctggaacatt aatatatgtg tttgaaatta tagatggttg gtgtcgcatt    780

tattggaaca atcataatga gtggatatgg catgagagat tgattgtgaa agaagtgttt    840

taa                                                                   843
```

<210> SEQ ID NO 48
<211> LENGTH: 280
<212> TYPE: PRT
<213> ORGANISM: artificial
<220> FEATURE:
<223> OTHER INFORMATION: artificial construct

<400> SEQUENCE: 48

```
Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Ala Ala Thr His Glu His Ser Ala Gln Trp Leu Asn Asn Tyr Lys Lys
        35                  40                  45

Gly Tyr Gly Tyr Gly Pro Tyr Pro Leu Gly Ile Asn Gly Gly Met His
    50                  55                  60

Tyr Gly Val Asp Phe Phe Met Asn Ile Gly Thr Pro Val Lys Ala Ile
65                  70                  75                  80

Ser Ser Gly Lys Ile Val Glu Ala Gly Trp Ser Asn Tyr Gly Gly Gly
                85                  90                  95

Asn Gln Ile Gly Leu Ile Glu Asn Asp Gly Val His Arg Gln Trp Tyr
            100                 105                 110

Met His Leu Ser Lys Tyr Asn Val Lys Val Gly Asp Tyr Val Lys Ala
        115                 120                 125

Gly Gln Ile Ile Gly Trp Ser Gly Ser Thr Gly Tyr Ser Thr Ala Pro
    130                 135                 140

His Leu His Phe Gln Arg Met Val Asn Ser Phe Ser Asn Ser Thr Ala
145                 150                 155                 160

Gln Asp Pro Met Pro Phe Leu Lys Ser Ala Gly Tyr Gly Lys Ala Gly
                165                 170                 175

Gly Thr Val Thr Pro Thr Pro Asn Thr Gly Gly Lys Ser Ala Ser Lys
            180                 185                 190

Ile Thr Val Gly Ser Lys Ala Pro Tyr Asn Leu Lys Trp Ser Lys Gly
        195                 200                 205

Ala Tyr Phe Asn Ala Lys Ile Asp Gly Leu Gly Ala Thr Ser Ala Thr
```

```
    210                 215                 220

Arg Tyr Gly Asp Asn Arg Thr Asn Tyr Arg Phe Asp Val Gly Gln Ala
225                 230                 235                 240

Val Tyr Ala Pro Gly Thr Leu Ile Tyr Val Phe Glu Ile Ile Asp Gly
                245                 250                 255

Trp Cys Arg Ile Tyr Trp Asn Asn His Asn Glu Trp Ile Trp His Glu
            260                 265                 270

Arg Leu Ile Val Lys Glu Val Phe
        275                 280


<210> SEQ ID NO 49
<211> LENGTH: 1755
<212> TYPE: DNA
<213> ORGANISM: artificial
<220> FEATURE:
<223> OTHER INFORMATION: artificial construct

<400> SEQUENCE: 49

atgagaggat cgcatcacca tcaccatcac ggatctggct ctggatctgg tatcgaggga     60

agggcaaaga aagatgaaaa atcacaagta tgtagtggtt tggctatgga aaaatatgac    120

attacaaatt taaatgctaa acaagataaa tcaaagaatg ggagcgtgaa agagttgaaa    180

catatctatt caaaccatat taaaggtaac aagattacag caccaaaacc tagtattcaa    240

ggtgtggtca tccacaatga ttatggtagt atgacaccta gtcaatactt accatggtta    300

tatgcacgtg agaataacgg tacacacgtt aacggttggg ctagtgttta tgcaaataga    360

aacgaagtgc tttggtatca tccgacagac tacgtagagt ggcattgtgg taatcaatgg    420

gcaaatgcta acttaatcgg atttgaagtg tgtgagtcgt atcctggtag aatctcggac    480

aaattattct tagaaaatga agaagcgaca ttgaaagtag ctgcggatgt gatgaagtcg    540

tacggattac cagttaatcg caacactgta cgtctgcata acgaattctt cggaacttct    600

tgtccacatc gttcgtggga cttgcatgtt ggcaaaggtg agccttacac aactactaat    660

attaataaaa tgaaagacta cttcatcaaa cgcatcaaac attattatga cggtgagctc    720

gcaaagaaag atgaaaaatc acaagtatgt agtggtttgg ctatggaaaa atatgacatt    780

acaaatttaa atgctaaaca agataaatca aagaatggga gcgtgaaaga gttgaaacat    840

atctattcaa accatattaa aggtaacaag attacagcac caaaacctag tattcaaggt    900

gtggtcatcc acaatgatta tggtagtatg acacctagtc aatacttacc atggttatat    960

gcacgtgaga ataacggtac acacgttaac ggttgggcta gtgtttatgc aaatagaaac   1020

gaagtgcttt ggtatcatcc gacagactac gtagagtggc attgtggtaa tcaatgggca   1080

aatgctaact taatcggatt tgaagtgtgt gagtcgtatc ctggtagaat ctcggacaaa   1140

ttattcttag aaaatgaaga agcgacattg aaagtagctg cggatgtgat gaagtcgtac   1200

ggattaccag ttaatcgcaa cactgtacgt ctgcataacg aattcttcgg aacttcttgt   1260

ccacatcgtt cgtgggactt gcatgttggc aaaggtgagc cttacacaac tactaatatt   1320

aataaaatga aagactactt catcaaacgc atcaaacatt attatgacgg tggaaagcta   1380

gaagtaagca aagcagcaac tatcaaacaa tctgacgtta agcaagaagt taaaaagcaa   1440

gaagcaaaac aaattgtgaa agcaacagat tggaaacaga ataaagatgg catttggtat   1500

aaagctgaac atgcttcgtt cacagtgaca gcaccagagg gaattatcac aagatacaaa   1560

ggtccttgga ctggtcaccc acaagctggt gtattacaaa aaggtcaaac gattaaatat   1620

gatgaggttc aaaaatttga cggtcatgtt tgggtatcgt gggaaacgtt tgagggcgaa   1680
```

actgtataca tgccggtacg cacatgggac gctaaaactg gtaaagttgg taagttgtgg 1740
ggcgaaatta aataa 1755

<210> SEQ ID NO 50
<211> LENGTH: 584
<212> TYPE: PRT
<213> ORGANISM: artificial
<220> FEATURE:
<223> OTHER INFORMATION: artificial construct

<400> SEQUENCE: 50

```
Met Arg Gly Ser His His His His His His Gly Ser Gly Ser Gly Ser
1               5                   10                  15

Gly Ile Glu Gly Arg Ala Lys Lys Asp Glu Lys Ser Gln Val Cys Ser
            20                  25                  30

Gly Leu Ala Met Glu Lys Tyr Asp Ile Thr Asn Leu Asn Ala Lys Gln
        35                  40                  45

Asp Lys Ser Lys Asn Gly Ser Val Lys Glu Leu Lys His Ile Tyr Ser
    50                  55                  60

Asn His Ile Lys Gly Asn Lys Ile Thr Ala Pro Lys Pro Ser Ile Gln
65                  70                  75                  80

Gly Val Val Ile His Asn Asp Tyr Gly Ser Met Thr Pro Ser Gln Tyr
                85                  90                  95

Leu Pro Trp Leu Tyr Ala Arg Glu Asn Asn Gly Thr His Val Asn Gly
            100                 105                 110

Trp Ala Ser Val Tyr Ala Asn Arg Asn Glu Val Leu Trp Tyr His Pro
        115                 120                 125

Thr Asp Tyr Val Glu Trp His Cys Gly Asn Gln Trp Ala Asn Ala Asn
    130                 135                 140

Leu Ile Gly Phe Glu Val Cys Glu Ser Tyr Pro Gly Arg Ile Ser Asp
145                 150                 155                 160

Lys Leu Phe Leu Glu Asn Glu Glu Ala Thr Leu Lys Val Ala Ala Asp
                165                 170                 175

Val Met Lys Ser Tyr Gly Leu Pro Val Asn Arg Asn Thr Val Arg Leu
            180                 185                 190

His Asn Glu Phe Phe Gly Thr Ser Cys Pro His Arg Ser Trp Asp Leu
        195                 200                 205

His Val Gly Lys Gly Glu Pro Tyr Thr Thr Thr Asn Ile Asn Lys Met
    210                 215                 220

Lys Asp Tyr Phe Ile Lys Arg Ile Lys His Tyr Tyr Asp Gly Glu Leu
225                 230                 235                 240

Ala Lys Lys Asp Glu Lys Ser Gln Val Cys Ser Gly Leu Ala Met Glu
                245                 250                 255

Lys Tyr Asp Ile Thr Asn Leu Asn Ala Lys Gln Asp Lys Ser Lys Asn
            260                 265                 270

Gly Ser Val Lys Glu Leu Lys His Ile Tyr Ser Asn His Ile Lys Gly
        275                 280                 285

Asn Lys Ile Thr Ala Pro Lys Pro Ser Ile Gln Gly Val Val Ile His
    290                 295                 300

Asn Asp Tyr Gly Ser Met Thr Pro Ser Gln Tyr Leu Pro Trp Leu Tyr
305                 310                 315                 320

Ala Arg Glu Asn Asn Gly Thr His Val Asn Gly Trp Ala Ser Val Tyr
                325                 330                 335

Ala Asn Arg Asn Glu Val Leu Trp Tyr His Pro Thr Asp Tyr Val Glu
```

```
            340                 345                 350

Trp His Cys Gly Asn Gln Trp Ala Asn Ala Asn Leu Ile Gly Phe Glu
        355                 360                 365

Val Cys Glu Ser Tyr Pro Gly Arg Ile Ser Asp Lys Leu Phe Leu Glu
    370                 375                 380

Asn Glu Glu Ala Thr Leu Lys Val Ala Ala Asp Val Met Lys Ser Tyr
385                 390                 395                 400

Gly Leu Pro Val Asn Arg Asn Thr Val Arg Leu His Asn Glu Phe Phe
                405                 410                 415

Gly Thr Ser Cys Pro His Arg Ser Trp Asp Leu His Val Gly Lys Gly
            420                 425                 430

Glu Pro Tyr Thr Thr Thr Asn Ile Asn Lys Met Lys Asp Tyr Phe Ile
        435                 440                 445

Lys Arg Ile Lys His Tyr Tyr Asp Gly Gly Lys Leu Glu Val Ser Lys
    450                 455                 460

Ala Ala Thr Ile Lys Gln Ser Asp Val Lys Gln Glu Val Lys Lys Gln
465                 470                 475                 480

Glu Ala Lys Gln Ile Val Lys Ala Thr Asp Trp Lys Gln Asn Lys Asp
                485                 490                 495

Gly Ile Trp Tyr Lys Ala Glu His Ala Ser Phe Thr Val Thr Ala Pro
            500                 505                 510

Glu Gly Ile Ile Thr Arg Tyr Lys Gly Pro Trp Thr Gly His Pro Gln
        515                 520                 525

Ala Gly Val Leu Gln Lys Gly Gln Thr Ile Lys Tyr Asp Glu Val Gln
    530                 535                 540

Lys Phe Asp Gly His Val Trp Val Ser Trp Glu Thr Phe Glu Gly Glu
545                 550                 555                 560

Thr Val Tyr Met Pro Val Arg Thr Trp Asp Ala Lys Thr Gly Lys Val
                565                 570                 575

Gly Lys Leu Trp Gly Glu Ile Lys
            580
```

<210> SEQ ID NO 51
<211> LENGTH: 1749
<212> TYPE: DNA
<213> ORGANISM: artificial
<220> FEATURE:
<223> OTHER INFORMATION: artificial construct

<400> SEQUENCE: 51

```
atgagaggat cgcatcacca tcaccatcac ggatctggct ctggatctgg tatcgaggga     60

agggcaaaga aagatgaaaa atcacaagta tgtagtggtt tggctatgga aaaatatgac    120

attacaaatt taaatgctaa acaagataaa tcaaagaatg ggagcgtgaa agagttgaaa    180

catatctatt caaaccatat taaaggtaac aagattacag caccaaaacc tagtattcaa    240

ggtgtggtca tccacaatga ttatggtagt atgacaccta gtcaatactt accatggtta    300

tatgcacgtg agaataacgg tacacacgtt aacggttggg ctagtgttta tgcaaataga    360

aacgaagtgc tttggtatca tccgacagac tacgtagagt ggcattgtgg taatcaatgg    420

gcaaatgcta acttaatcgg atttgaagtg tgtgagtcgt atcctggtag aatctcggac    480

aaattattct tagaaaatga agaagcgaca ttgaaagtag ctgcggatgt gatgaagtcg    540

tacggattac cagttaatcg caacactgta cgtctgcata acgaattctt cggaacttct    600

tgtccacatc gttcgtggga cttgcatgtt ggcaaaggtg agccttacac aactactaat    660
```

```
attaataaaa tgaaagacta cttcatcaaa cgcatcaaac attattatga cggtgagctc    720

gcaaagaaag atgaaaaatc acaagtatgt agtggtttgg ctatggaaaa atatgacatt    780

acaaatttaa atgctaaaca agataaatca aagaatggga gcgtgaaaga gttgaaacat    840

atctattcaa accatattaa aggtaacaag attacagcac caaaacctag tattcaaggt    900

gtggtcatcc acaatgatta tggtagtatg acacctagtc aatacttacc atggttatat    960

gcacgtgaga ataacggtac acacgttaac ggttgggcta gtgtttatgc aaatagaaac   1020

gaagtgcttt ggtatcatcc gacagactac gtagagtggc attgtggtaa tcaatgggca   1080

aatgctaact taatcggatt tgaagtgtgt gagtcgtatc ctggtagaat ctcggacaaa   1140

ttattcttag aaaatgaaga agcgacattg aaagtagctg cggatgtgat gaagtcgtac   1200

ggattaccag ttaatcgcaa cactgtacgt ctgcataacg aattcttcgg aacttcttgt   1260

ccacatcgtt cgtgggactt gcatgttggc aaaggtgagc cttacacaac tactaatatt   1320

aataaaatga aagactactt catcaaacgc atcaaacatt attatgacgg tggaaagcta   1380

gaagtaagca aagcagcaac tatcaaacaa tctgacgtta agcaagaagt taaaaagcaa   1440

gaagcaaaac aaattgtgaa agcaacagat tggaaaacaa acaaatatgg cacactatat   1500

aaatcagagt cagctagctt cacacctaat acagatataa taacaagaac gactggtcca   1560

tttagaagca tgccgcagtc aggagtctta aaagcaggtc aaacaattca ttatgatgaa   1620

gtgatgaaac aagacggtca tgtttgggta ggttatacag gtaacagtgg ccaacgtatt   1680

tacttgcctg taagaacatg gaataaatct actaatactt taggtgttct ttggggaact   1740

ataaagtaa                                                           1749
```

<210> SEQ ID NO 52
<211> LENGTH: 582
<212> TYPE: PRT
<213> ORGANISM: artificial
<220> FEATURE:
<223> OTHER INFORMATION: artificial construct

<400> SEQUENCE: 52

```
Met Arg Gly Ser His His His His His His Gly Ser Gly Ser Gly Ser
1               5                   10                  15

Gly Ile Glu Gly Arg Ala Lys Lys Asp Glu Lys Ser Gln Val Cys Ser
            20                  25                  30

Gly Leu Ala Met Glu Lys Tyr Asp Ile Thr Asn Leu Asn Ala Lys Gln
        35                  40                  45

Asp Lys Ser Lys Asn Gly Ser Val Lys Glu Leu Lys His Ile Tyr Ser
    50                  55                  60

Asn His Ile Lys Gly Asn Lys Ile Thr Ala Pro Lys Pro Ser Ile Gln
65                  70                  75                  80

Gly Val Val Ile His Asn Asp Tyr Gly Ser Met Thr Pro Ser Gln Tyr
                85                  90                  95

Leu Pro Trp Leu Tyr Ala Arg Glu Asn Asn Gly Thr His Val Asn Gly
            100                 105                 110

Trp Ala Ser Val Tyr Ala Asn Arg Asn Glu Val Leu Trp Tyr His Pro
        115                 120                 125

Thr Asp Tyr Val Glu Trp His Cys Gly Asn Gln Trp Ala Asn Ala Asn
    130                 135                 140

Leu Ile Gly Phe Glu Val Cys Glu Ser Tyr Pro Gly Arg Ile Ser Asp
145                 150                 155                 160

Lys Leu Phe Leu Glu Asn Glu Glu Ala Thr Leu Lys Val Ala Ala Asp
```

```
                165                 170                 175

Val Met Lys Ser Tyr Gly Leu Pro Val Asn Arg Asn Thr Val Arg Leu
            180                 185                 190

His Asn Glu Phe Phe Gly Thr Ser Cys Pro His Arg Ser Trp Asp Leu
        195                 200                 205

His Val Gly Lys Gly Glu Pro Tyr Thr Thr Thr Asn Ile Asn Lys Met
    210                 215                 220

Lys Asp Tyr Phe Ile Lys Arg Ile Lys His Tyr Tyr Asp Gly Glu Leu
225                 230                 235                 240

Ala Lys Lys Asp Glu Lys Ser Gln Val Cys Ser Gly Leu Ala Met Glu
                245                 250                 255

Lys Tyr Asp Ile Thr Asn Leu Asn Ala Lys Gln Asp Lys Ser Lys Asn
            260                 265                 270

Gly Ser Val Lys Glu Leu Lys His Ile Tyr Ser Asn His Ile Lys Gly
        275                 280                 285

Asn Lys Ile Thr Ala Pro Lys Pro Ser Ile Gln Gly Val Val Ile His
    290                 295                 300

Asn Asp Tyr Gly Ser Met Thr Pro Ser Gln Tyr Leu Pro Trp Leu Tyr
305                 310                 315                 320

Ala Arg Glu Asn Asn Gly Thr His Val Asn Gly Trp Ala Ser Val Tyr
                325                 330                 335

Ala Asn Arg Asn Glu Val Leu Trp Tyr His Pro Thr Asp Tyr Val Glu
            340                 345                 350

Trp His Cys Gly Asn Gln Trp Ala Asn Ala Asn Leu Ile Gly Phe Glu
        355                 360                 365

Val Cys Glu Ser Tyr Pro Gly Arg Ile Ser Asp Lys Leu Phe Leu Glu
    370                 375                 380

Asn Glu Glu Ala Thr Leu Lys Val Ala Ala Asp Val Met Lys Ser Tyr
385                 390                 395                 400

Gly Leu Pro Val Asn Arg Asn Thr Val Arg Leu His Asn Glu Phe Phe
                405                 410                 415

Gly Thr Ser Cys Pro His Arg Ser Trp Asp Leu His Val Gly Lys Gly
            420                 425                 430

Glu Pro Tyr Thr Thr Thr Asn Ile Asn Lys Met Lys Asp Tyr Phe Ile
        435                 440                 445

Lys Arg Ile Lys His Tyr Tyr Asp Gly Gly Lys Leu Glu Val Ser Lys
    450                 455                 460

Ala Ala Thr Ile Lys Gln Ser Asp Val Lys Gln Glu Val Lys Lys Gln
465                 470                 475                 480

Glu Ala Lys Gln Ile Val Lys Ala Thr Asp Trp Lys Thr Asn Lys Tyr
                485                 490                 495

Gly Thr Leu Tyr Lys Ser Glu Ser Ala Ser Phe Thr Pro Asn Thr Asp
            500                 505                 510

Ile Ile Thr Arg Thr Thr Gly Pro Phe Arg Ser Met Pro Gln Ser Gly
        515                 520                 525

Val Leu Lys Ala Gly Gln Thr Ile His Tyr Asp Glu Val Met Lys Gln
    530                 535                 540

Asp Gly His Val Trp Val Gly Tyr Thr Gly Asn Ser Gly Gln Arg Ile
545                 550                 555                 560

Tyr Leu Pro Val Arg Thr Trp Asn Lys Ser Thr Asn Thr Leu Gly Val
                565                 570                 575

Leu Trp Gly Thr Ile Lys
            580
```

<210> SEQ ID NO 53
<211> LENGTH: 1755
<212> TYPE: DNA
<213> ORGANISM: artificial
<220> FEATURE:
<223> OTHER INFORMATION: artificial construct

<400> SEQUENCE: 53

```
atgagaggat cgcatcacca tcaccatcac ggatctggct ctggatctgg tatcgaggga      60
agggcaaaga aagatgaaaa atcacaagta tgtagtggtt tggctatgga aaaatatgac     120
attacaaatt taaatgctaa acaagataaa tcaaagaatg ggagcgtgaa agagttgaaa     180
catatctatt caaaccatat taaaggtaac aagattacag caccaaaacc tagtattcaa     240
ggtgtggtca tccacaatga ttatggtagt atgacaccta gtcaatactt accatggtta     300
tatgcacgtg agaataacgg tacacacgtt aacggttggg ctagtgttta tgcaaataga     360
aacgaagtgc tttggtatca tccgacagac tacgtagagt ggcattgtgg taatcaatgg     420
gcaaatgcta acttaatcgg atttgaagtg tgtgagtcgt atcctggtag aatctcggac     480
aaattattct tagaaaatga agaagcgaca ttgaaagtag ctgcggatgt gatgaagtcg     540
tacggattac cagttaatcg caacactgta cgtctgcata acgaattctt cggaacttct     600
tgtccacatc gttcgtggga cttgcatgtt ggcaaaggtg agccttacac aactactaat     660
attaataaaa tgaaagacta cttcatcaaa cgcatcaaac attattatga cggtgagctc     720
gcaaagaaag atgaaaaatc acaagtatgt agtggtttgg ctatggaaaa atatgacatt     780
acaaatttaa atgctaaaca agataaatca aagaatggga gcgtgaaaga gttgaaacat     840
atctattcaa accatattaa aggtaacaag attacagcac caaaacctag tattcaaggt     900
gtggtcatcc acaatgatta tggtagtatg acacctagtc aatacttacc atggttatat     960
gcacgtgaga ataacggtac acacgttaac ggttgggcta gtgtttatgc aaatagaaac    1020
gaagtgcttt ggtatcatcc gacagactac gtagagtggc attgtggtaa tcaatgggca    1080
aatgctaact taatcggatt tgaagtgtgt gagtcgtatc ctggtagaat ctcggacaaa    1140
ttattcttag aaaatgaaga agcgacattg aaagtagctg cggatgtgat gaagtcgtac    1200
ggattaccag ttaatcgcaa cactgtacgt ctgcataacg aattcttcgg aacttcttgt    1260
ccacatcgtt cgtgggactt gcatgttggc aaaggtgagc cttacacaac tactaatatt    1320
aataaaatga aagactactt catcaaacgc atcaaacatt attatgacgg tggaaagcta    1380
gaagtaagca aagcagcaac tatcaaacaa tctgacgtta agcaagaagt taaaaagcaa    1440
gaagcaaaac aaattgtgaa agcaacagat ggtaaatctg caagtaaaat aacagttgga    1500
agtaaagcgc cttataacct taaatggtca aaaggtgctt attttaatgc gaaaatcgac    1560
ggcttaggtg ctacttcagc cactagatac ggtgataatc gtactaacta tagattcgat    1620
gttggacagg ctgtatacgc gcctggaaca ttaatatatg tgtttgaaat tatagatggt    1680
tggtgtcgca tttattggaa caatcataat gagtggatat ggcatgagag attgattgtg    1740
aaagaagtgt tttaa                                                     1755
```

<210> SEQ ID NO 54
<211> LENGTH: 584
<212> TYPE: PRT
<213> ORGANISM: artificial
<220> FEATURE:
<223> OTHER INFORMATION: artificial construct

<400> SEQUENCE: 54

```
Met Arg Gly Ser His His His His His His Gly Ser Gly Ser Gly Ser
1               5                   10                  15

Gly Ile Glu Gly Arg Ala Lys Lys Asp Glu Lys Ser Gln Val Cys Ser
            20                  25                  30

Gly Leu Ala Met Glu Lys Tyr Asp Ile Thr Asn Leu Asn Ala Lys Gln
        35                  40                  45

Asp Lys Ser Lys Asn Gly Ser Val Lys Glu Leu Lys His Ile Tyr Ser
    50                  55                  60

Asn His Ile Lys Gly Asn Lys Ile Thr Ala Pro Lys Pro Ser Ile Gln
65                  70                  75                  80

Gly Val Val Ile His Asn Asp Tyr Gly Ser Met Thr Pro Ser Gln Tyr
                85                  90                  95

Leu Pro Trp Leu Tyr Ala Arg Glu Asn Asn Gly Thr His Val Asn Gly
            100                 105                 110

Trp Ala Ser Val Tyr Ala Asn Arg Asn Glu Val Leu Trp Tyr His Pro
        115                 120                 125

Thr Asp Tyr Val Glu Trp His Cys Gly Asn Gln Trp Ala Asn Ala Asn
    130                 135                 140

Leu Ile Gly Phe Glu Val Cys Glu Ser Tyr Pro Gly Arg Ile Ser Asp
145                 150                 155                 160

Lys Leu Phe Leu Glu Asn Glu Glu Ala Thr Leu Lys Val Ala Ala Asp
                165                 170                 175

Val Met Lys Ser Tyr Gly Leu Pro Val Asn Arg Asn Thr Val Arg Leu
            180                 185                 190

His Asn Glu Phe Phe Gly Thr Ser Cys Pro His Arg Ser Trp Asp Leu
        195                 200                 205

His Val Gly Lys Gly Glu Pro Tyr Thr Thr Thr Asn Ile Asn Lys Met
    210                 215                 220

Lys Asp Tyr Phe Ile Lys Arg Ile Lys His Tyr Tyr Asp Gly Glu Leu
225                 230                 235                 240

Ala Lys Lys Asp Glu Lys Ser Gln Val Cys Ser Gly Leu Ala Met Glu
                245                 250                 255

Lys Tyr Asp Ile Thr Asn Leu Asn Ala Lys Gln Asp Lys Ser Lys Asn
            260                 265                 270

Gly Ser Val Lys Glu Leu Lys His Ile Tyr Ser Asn His Ile Lys Gly
        275                 280                 285

Asn Lys Ile Thr Ala Pro Lys Pro Ser Ile Gln Gly Val Val Ile His
    290                 295                 300

Asn Asp Tyr Gly Ser Met Thr Pro Ser Gln Tyr Leu Pro Trp Leu Tyr
305                 310                 315                 320

Ala Arg Glu Asn Asn Gly Thr His Val Asn Gly Trp Ala Ser Val Tyr
                325                 330                 335

Ala Asn Arg Asn Glu Val Leu Trp Tyr His Pro Thr Asp Tyr Val Glu
            340                 345                 350

Trp His Cys Gly Asn Gln Trp Ala Asn Ala Asn Leu Ile Gly Phe Glu
        355                 360                 365

Val Cys Glu Ser Tyr Pro Gly Arg Ile Ser Asp Lys Leu Phe Leu Glu
    370                 375                 380

Asn Glu Glu Ala Thr Leu Lys Val Ala Ala Asp Val Met Lys Ser Tyr
385                 390                 395                 400

Gly Leu Pro Val Asn Arg Asn Thr Val Arg Leu His Asn Glu Phe Phe
                405                 410                 415
```

```
Gly Thr Ser Cys Pro His Arg Ser Trp Asp Leu His Val Gly Lys Gly
            420                 425                 430

Glu Pro Tyr Thr Thr Thr Asn Ile Asn Lys Met Lys Asp Tyr Phe Ile
        435                 440                 445

Lys Arg Ile Lys His Tyr Tyr Asp Gly Gly Lys Leu Glu Val Ser Lys
    450                 455                 460

Ala Ala Thr Ile Lys Gln Ser Asp Val Lys Gln Glu Val Lys Lys Gln
465                 470                 475                 480

Glu Ala Lys Gln Ile Val Lys Ala Thr Asp Gly Lys Ser Ala Ser Lys
                485                 490                 495

Ile Thr Val Gly Ser Lys Ala Pro Tyr Asn Leu Lys Trp Ser Lys Gly
            500                 505                 510

Ala Tyr Phe Asn Ala Lys Ile Asp Gly Leu Gly Ala Thr Ser Ala Thr
        515                 520                 525

Arg Tyr Gly Asp Asn Arg Thr Asn Tyr Arg Phe Asp Val Gly Gln Ala
    530                 535                 540

Val Tyr Ala Pro Gly Thr Leu Ile Tyr Val Phe Glu Ile Ile Asp Gly
545                 550                 555                 560

Trp Cys Arg Ile Tyr Trp Asn Asn His Asn Glu Trp Ile Trp His Glu
                565                 570                 575

Arg Leu Ile Val Lys Glu Val Phe
            580
```

<210> SEQ ID NO 55
<211> LENGTH: 1533
<212> TYPE: DNA
<213> ORGANISM: artificial
<220> FEATURE:
<223> OTHER INFORMATION: artificial construct

<400> SEQUENCE: 55

```
atgagaggat cgcatcacca tcaccatcac ggatctggct ctggatctgg tatcgaggga     60

aggatggcta agactcaagc agaaataaat aaacgtttag atgcttatgc aaaaggaaca    120

gtagatagcc cttacagagt taaaaaagct acaagttatg acccatcatt tggtgtaatg    180

gaagcaggag ccattgatgc agatggttac tatcacgctc agtgtcaaga ccttattaca    240

gactatgttt tatggttaac agataataaa gttagaactt ggggtaatgc taaagaccaa    300

attaaacaga gttatggtac tggatttaaa atacatgaaa ataaaccttc tactgtacct    360

aaaaaaggtt ggattgcggt atttacatcc ggtagttatg aacagtgggg tcacataggt    420

attgtatatg atggaggtaa tacttctaca tttactattt tagagcaaaa ctggaatggt    480

tatgctaata aaaaacctac aaaacgtgta gataattatt acggattaac tcacttcatt    540

gaaatacctg taaaagcagg aactactgtt aaaaaagaaa cagctaagaa aagcgcaagt    600

aaaacgcctg cacctaaaaa gaaagcaaca ctaaaagttt ctaagaatga gctcatggct    660

aagactcaag cagaaataaa taaacgttta gatgcttatg caaaaggaac agtagatagc    720

ccttacagag ttaaaaaagc tacaagttat gacccatcat ttggtgtaat ggaagcagga    780

gccattgatg cagatggtta ctatcacgct cagtgtcaag accttattac agactatgtt    840

ttatggttaa cagataataa agttagaact tggggtaatg ctaaagacca aattaaacag    900

agttatggta ctggatttaa aatacatgaa aataaacctt ctactgtacc taaaaaaggt    960

tggattgcgg tatttacatc cggtagttat gaacagtggg gtcacatagg tattgtatat   1020

gatggaggta atacttctac atttactatt ttagagcaaa actggaatgg ttatgctaat   1080
```

```
aaaaaaccta caaaacgtgt agataattat tacggattaa ctcacttcat tgaaatacct   1140

gtaaaagcag gaaagctaga agtaagcaaa gcagcaacta tcaaacaatc tgacgttaag   1200

caagaagtta aaaagcaaga agcaaaacaa attgtgaaag caacagattg gaaacagaat   1260

aaagatggca tttggtataa agctgaacat gcttcgttca cagtgacagc accagaggga   1320

attatcacaa gatacaaagg tccttggact ggtcacccac aagctggtgt attacaaaaa   1380

ggtcaaacga ttaaatatga tgaggttcaa aaatttgacg gtcatgtttg ggtatcgtgg   1440

gaaacgtttg agggcgaaac tgtatacatg ccggtacgca catgggacgc taaaactggt   1500

aaagttggta agttgtgggg cgaaattaaa taa                                1533


<210> SEQ ID NO 56
<211> LENGTH: 510
<212> TYPE: PRT
<213> ORGANISM: artificial
<220> FEATURE:
<223> OTHER INFORMATION: artificial construct

<400> SEQUENCE: 56

Met Arg Gly Ser His His His His His His Gly Ser Gly Ser Gly Ser
1               5                   10                  15

Gly Ile Glu Gly Arg Met Ala Lys Thr Gln Ala Glu Ile Asn Lys Arg
            20                  25                  30

Leu Asp Ala Tyr Ala Lys Gly Thr Val Asp Ser Pro Tyr Arg Val Lys
        35                  40                  45

Lys Ala Thr Ser Tyr Asp Pro Ser Phe Gly Val Met Glu Ala Gly Ala
    50                  55                  60

Ile Asp Ala Asp Gly Tyr Tyr His Ala Gln Cys Gln Asp Leu Ile Thr
65                  70                  75                  80

Asp Tyr Val Leu Trp Leu Thr Asp Asn Lys Val Arg Thr Trp Gly Asn
                85                  90                  95

Ala Lys Asp Gln Ile Lys Gln Ser Tyr Gly Thr Gly Phe Lys Ile His
            100                 105                 110

Glu Asn Lys Pro Ser Thr Val Pro Lys Lys Gly Trp Ile Ala Val Phe
        115                 120                 125

Thr Ser Gly Ser Tyr Glu Gln Trp Gly His Ile Gly Ile Val Tyr Asp
    130                 135                 140

Gly Gly Asn Thr Ser Thr Phe Thr Ile Leu Glu Gln Asn Trp Asn Gly
145                 150                 155                 160

Tyr Ala Asn Lys Lys Pro Thr Lys Arg Val Asp Asn Tyr Tyr Gly Leu
                165                 170                 175

Thr His Phe Ile Glu Ile Pro Val Lys Ala Gly Thr Thr Val Lys Lys
            180                 185                 190

Glu Thr Ala Lys Lys Ser Ala Ser Lys Thr Pro Ala Pro Lys Lys Lys
        195                 200                 205

Ala Thr Leu Lys Val Ser Lys Asn Glu Leu Met Ala Lys Thr Gln Ala
    210                 215                 220

Glu Ile Asn Lys Arg Leu Asp Ala Tyr Ala Lys Gly Thr Val Asp Ser
225                 230                 235                 240

Pro Tyr Arg Val Lys Lys Ala Thr Ser Tyr Asp Pro Ser Phe Gly Val
                245                 250                 255

Met Glu Ala Gly Ala Ile Asp Ala Asp Gly Tyr Tyr His Ala Gln Cys
            260                 265                 270

Gln Asp Leu Ile Thr Asp Tyr Val Leu Trp Leu Thr Asp Asn Lys Val
```

```
        275                 280                 285

Arg Thr Trp Gly Asn Ala Lys Asp Gln Ile Lys Gln Ser Tyr Gly Thr
    290                 295                 300

Gly Phe Lys Ile His Glu Asn Lys Pro Ser Thr Val Pro Lys Lys Gly
305                 310                 315                 320

Trp Ile Ala Val Phe Thr Ser Gly Ser Tyr Glu Gln Trp Gly His Ile
                325                 330                 335

Gly Ile Val Tyr Asp Gly Gly Asn Thr Ser Thr Phe Thr Ile Leu Glu
            340                 345                 350

Gln Asn Trp Asn Gly Tyr Ala Asn Lys Lys Pro Thr Lys Arg Val Asp
        355                 360                 365

Asn Tyr Tyr Gly Leu Thr His Phe Ile Glu Ile Pro Val Lys Ala Gly
    370                 375                 380

Lys Leu Glu Val Ser Lys Ala Ala Thr Ile Lys Gln Ser Asp Val Lys
385                 390                 395                 400

Gln Glu Val Lys Lys Gln Glu Ala Lys Gln Ile Val Lys Ala Thr Asp
                405                 410                 415

Trp Lys Gln Asn Lys Asp Gly Ile Trp Tyr Lys Ala Glu His Ala Ser
            420                 425                 430

Phe Thr Val Thr Ala Pro Glu Gly Ile Ile Thr Arg Tyr Lys Gly Pro
        435                 440                 445

Trp Thr Gly His Pro Gln Ala Gly Val Leu Gln Lys Gly Gln Thr Ile
    450                 455                 460

Lys Tyr Asp Glu Val Gln Lys Phe Asp Gly His Val Trp Val Ser Trp
465                 470                 475                 480

Glu Thr Phe Glu Gly Glu Thr Val Tyr Met Pro Val Arg Thr Trp Asp
                485                 490                 495

Ala Lys Thr Gly Lys Val Gly Lys Leu Trp Gly Glu Ile Lys
            500                 505                 510


<210> SEQ ID NO 57
<211> LENGTH: 1470
<212> TYPE: DNA
<213> ORGANISM: artificial
<220> FEATURE:
<223> OTHER INFORMATION: artificial construct

<400> SEQUENCE: 57

atgagaggat cgcatcacca tcaccatcac ggatctggct ctggatctgg tatcgaggga      60

aggatggcta agactcaagc agaaataaat aaacgtttag atgcttatgc aaaaggaaca     120

gtagatagcc cttacagagt taaaaaagct acaagttatg acccatcatt tggtgtaatg     180

gaagcaggag ccattgatgc agatggttac tatcacgctc agtgtcaaga ccttattaca     240

gactatgttt tatggttaac agataataaa gttagaactt ggggtaatgc taaagaccaa     300

attaaacaga gttatggtac tggatttaaa atacatgaaa ataaaccttc tactgtacct     360

aaaaaaggtt ggattgcggt atttacatcc ggtagttatg aacagtgggg tcacataggt     420

attgtatatg atggaggtaa tacttctaca tttactattt tagagcaaaa ctggaatggt     480

tatgctaata aaaaacctac aaaacgtgta gataattatt acggattaac tcacttcatt     540

gaaatacctg taaaagcagg aactactgtt aaaaaagaaa cagctaagaa aagcgcaagt     600

aaaacgcctg cacctaaaaa gaaagcaaca ctaaaagttt ctaagaatga gctcatggct     660

aagactcaag cagaaataaa taaacgttta gatgcttatg caaaaggaac agtagatagc     720

ccttacagag ttaaaaaagc tacaagttat gacccatcat ttggtgtaat ggaagcagga     780
```

```
gccattgatg cagatggtta ctatcacgct cagtgtcaag accttattac agactatgtt    840

ttatggttaa cagataataa agttagaact tggggtaatg ctaaagacca aattaaacag    900

agttatggta ctggatttaa aatacatgaa aataaacctt ctactgtacc taaaaaaggt    960

tggattgcgg tatttacatc cggtagttat gaacagtggg gtcacatagg tattgtatat   1020

gatggaggta atacttctac atttactatt ttagagcaaa actggaatgg ttatgctaat   1080

aaaaaaccta caaaacgtgt agataattat tacggattaa ctcacttcat tgaaatacct   1140

gtaaaagcag gaaaagcagg tggtacagta actccaacgc cgaatacagg ttggaaaaca   1200

aacaaatatg gcacactata taaatcagag tcagctagct tcacacctaa tacagatata   1260

ataacaagaa cgactggtcc atttagaagc atgccgcagt caggagtctt aaaagcaggt   1320

caaacaattc attatgatga agtgatgaaa caagacggtc atgtttgggt aggttataca   1380

ggtaacagtg gccaacgtat ttacttgcct gtaagaacat ggaataaatc tactaatact   1440

ttaggtgttc tttggggaac tataaagtaa                                    1470
```

<210> SEQ ID NO 58
<211> LENGTH: 489
<212> TYPE: PRT
<213> ORGANISM: artificial
<220> FEATURE:
<223> OTHER INFORMATION: artificial construct

<400> SEQUENCE: 58

```
Met Arg Gly Ser His His His His His His Gly Ser Gly Ser Gly Ser
1               5                   10                  15

Gly Ile Glu Gly Arg Met Ala Lys Thr Gln Ala Glu Ile Asn Lys Arg
            20                  25                  30

Leu Asp Ala Tyr Ala Lys Gly Thr Val Asp Ser Pro Tyr Arg Val Lys
        35                  40                  45

Lys Ala Thr Ser Tyr Asp Pro Ser Phe Gly Val Met Glu Ala Gly Ala
    50                  55                  60

Ile Asp Ala Asp Gly Tyr Tyr His Ala Gln Cys Gln Asp Leu Ile Thr
65                  70                  75                  80

Asp Tyr Val Leu Trp Leu Thr Asp Asn Lys Val Arg Thr Trp Gly Asn
                85                  90                  95

Ala Lys Asp Gln Ile Lys Gln Ser Tyr Gly Thr Gly Phe Lys Ile His
            100                 105                 110

Glu Asn Lys Pro Ser Thr Val Pro Lys Lys Gly Trp Ile Ala Val Phe
        115                 120                 125

Thr Ser Gly Ser Tyr Glu Gln Trp Gly His Ile Gly Ile Val Tyr Asp
    130                 135                 140

Gly Gly Asn Thr Ser Thr Phe Thr Ile Leu Glu Gln Asn Trp Asn Gly
145                 150                 155                 160

Tyr Ala Asn Lys Lys Pro Thr Lys Arg Val Asp Asn Tyr Tyr Gly Leu
                165                 170                 175

Thr His Phe Ile Glu Ile Pro Val Lys Ala Gly Thr Thr Val Lys Lys
            180                 185                 190

Glu Thr Ala Lys Lys Ser Ala Ser Lys Thr Pro Ala Pro Lys Lys Lys
        195                 200                 205

Ala Thr Leu Lys Val Ser Lys Asn Glu Leu Met Ala Lys Thr Gln Ala
    210                 215                 220

Glu Ile Asn Lys Arg Leu Asp Ala Tyr Ala Lys Gly Thr Val Asp Ser
225                 230                 235                 240
```

```
Pro Tyr Arg Val Lys Lys Ala Thr Ser Tyr Asp Pro Ser Phe Gly Val
                245                 250                 255

Met Glu Ala Gly Ala Ile Asp Ala Asp Gly Tyr Tyr His Ala Gln Cys
            260                 265                 270

Gln Asp Leu Ile Thr Asp Tyr Val Leu Trp Leu Thr Asp Asn Lys Val
        275                 280                 285

Arg Thr Trp Gly Asn Ala Lys Asp Gln Ile Lys Gln Ser Tyr Gly Thr
    290                 295                 300

Gly Phe Lys Ile His Glu Asn Lys Pro Ser Thr Val Pro Lys Lys Gly
305                 310                 315                 320

Trp Ile Ala Val Phe Thr Ser Gly Ser Tyr Glu Gln Trp Gly His Ile
                325                 330                 335

Gly Ile Val Tyr Asp Gly Gly Asn Thr Ser Thr Phe Thr Ile Leu Glu
            340                 345                 350

Gln Asn Trp Asn Gly Tyr Ala Asn Lys Lys Pro Thr Lys Arg Val Asp
        355                 360                 365

Asn Tyr Tyr Gly Leu Thr His Phe Ile Glu Ile Pro Val Lys Ala Gly
    370                 375                 380

Lys Ala Gly Gly Thr Val Thr Pro Thr Pro Asn Thr Gly Trp Lys Thr
385                 390                 395                 400

Asn Lys Tyr Gly Thr Leu Tyr Lys Ser Glu Ser Ala Ser Phe Thr Pro
                405                 410                 415

Asn Thr Asp Ile Ile Thr Arg Thr Thr Gly Pro Phe Arg Ser Met Pro
            420                 425                 430

Gln Ser Gly Val Leu Lys Ala Gly Gln Thr Ile His Tyr Asp Glu Val
        435                 440                 445

Met Lys Gln Asp Gly His Val Trp Val Gly Tyr Thr Gly Asn Ser Gly
    450                 455                 460

Gln Arg Ile Tyr Leu Pro Val Arg Thr Trp Asn Lys Ser Thr Asn Thr
465                 470                 475                 480

Leu Gly Val Leu Trp Gly Thr Ile Lys
                485
```

<210> SEQ ID NO 59
<211> LENGTH: 1524
<212> TYPE: DNA
<213> ORGANISM: artificial
<220> FEATURE:
<223> OTHER INFORMATION: artificial construct

<400> SEQUENCE: 59

```
atgagaggat cgcatcacca tcaccatcac ggatctggct ctggatctgg tatcgaggga     60

aggatggcta agactcaagc agaaataaat aaacgtttag atgcttatgc aaaaggaaca    120

gtagatagcc cttacagagt taaaaaagct acaagttatg acccatcatt tggtgtaatg    180

gaagcaggag ccattgatgc agatggttac tatcacgctc agtgtcaaga ccttattaca    240

gactatgttt tatggttaac agataataaa gttagaactt ggggtaatgc taaagaccaa    300

attaaacaga gttatggtac tggatttaaa atacatgaaa ataaaccttc tactgtacct    360

aaaaaaggtt ggattgcggt atttacatcc ggtagttatg aacagtgggg tcacataggt    420

attgtatatg atggaggtaa tacttctaca tttactattt tagagcaaaa ctggaatggt    480

tatgctaata aaaaacctac aaaacgtgta gataattatt acggattaac tcacttcatt    540

gaaatacctg taaaagcagg aactactgtt aaaaaagaaa cagctaagaa aagcgcaagt    600
```

```
aaaacgcctg cacctaaaaa gaaagcaaca ctaaaagttt ctaagaatga gctcatggct    660

aagactcaag cagaaataaa taaacgttta gatgcttatg caaaaggaac agtagatagc    720

ccttacagag ttaaaaaagc tacaagttat gacccatcat ttggtgtaat ggaagcagga    780

gccattgatg cagatggtta ctatcacgct cagtgtcaag accttattac agactatgtt    840

ttatggttaa cagataataa agttagaact tggggtaatg ctaaagacca aattaaacag    900

agttatggta ctggatttaa aatacatgaa aataaacctt ctactgtacc taaaaaaggt    960

tggattgcgg tatttacatc cggtagttat gaacagtggg gtcacatagg tattgtatat   1020

gatggaggta atacttctac atttactatt ttagagcaaa actggaatgg ttatgctaat   1080

aaaaaaccta caaaacgtgt agataattat tacggattaa ctcacttcat tgaaatacct   1140

gtaaaagcag gaactactgt taaaaaagaa acagctaaga aaagcgcaag taaaacgcct   1200

gcacctaaaa agaaagcaac actaaaagtt tctaagaatg gtaaatctgc aagtaaaata   1260

acagttggaa gtaaagcgcc ttataacctt aaatggtcaa aaggtgctta ttttaatgcg   1320

aaaatcgacg gcttaggtgc tacttcagcc actagatacg gtgataatcg tactaactat   1380

agattcgatg ttggacaggc tgtatacgcg cctggaacat taatatatgt gtttgaaatt   1440

atagatggtt ggtgtcgcat ttattggaac aatcataatg agtggatatg gcatgagaga   1500

ttgattgtga aagaagtgtt ttaa                                          1524
```

<210> SEQ ID NO 60
<211> LENGTH: 507
<212> TYPE: PRT
<213> ORGANISM: artificial
<220> FEATURE:
<223> OTHER INFORMATION: artificial construct

<400> SEQUENCE: 60

```
Met Arg Gly Ser His His His His His His Gly Ser Gly Ser Gly Ser
1               5                   10                  15

Gly Ile Glu Gly Arg Met Ala Lys Thr Gln Ala Glu Ile Asn Lys Arg
            20                  25                  30

Leu Asp Ala Tyr Ala Lys Gly Thr Val Asp Ser Pro Tyr Arg Val Lys
        35                  40                  45

Lys Ala Thr Ser Tyr Asp Pro Ser Phe Gly Val Met Glu Ala Gly Ala
    50                  55                  60

Ile Asp Ala Asp Gly Tyr Tyr His Ala Gln Cys Gln Asp Leu Ile Thr
65                  70                  75                  80

Asp Tyr Val Leu Trp Leu Thr Asp Asn Lys Val Arg Thr Trp Gly Asn
                85                  90                  95

Ala Lys Asp Gln Ile Lys Gln Ser Tyr Gly Thr Gly Phe Lys Ile His
            100                 105                 110

Glu Asn Lys Pro Ser Thr Val Pro Lys Lys Gly Trp Ile Ala Val Phe
        115                 120                 125

Thr Ser Gly Ser Tyr Glu Gln Trp Gly His Ile Gly Ile Val Tyr Asp
    130                 135                 140

Gly Gly Asn Thr Ser Thr Phe Thr Ile Leu Glu Gln Asn Trp Asn Gly
145                 150                 155                 160

Tyr Ala Asn Lys Lys Pro Thr Lys Arg Val Asp Asn Tyr Tyr Gly Leu
                165                 170                 175

Thr His Phe Ile Glu Ile Pro Val Lys Ala Gly Thr Thr Val Lys Lys
            180                 185                 190

Glu Thr Ala Lys Lys Ser Ala Ser Lys Thr Pro Ala Pro Lys Lys Lys
```

```
        195                 200                 205

Ala Thr Leu Lys Val Ser Lys Asn Glu Leu Met Ala Lys Thr Gln Ala
    210                 215                 220

Glu Ile Asn Lys Arg Leu Asp Ala Tyr Ala Lys Gly Thr Val Asp Ser
225                 230                 235                 240

Pro Tyr Arg Val Lys Lys Ala Thr Ser Tyr Asp Pro Ser Phe Gly Val
                245                 250                 255

Met Glu Ala Gly Ala Ile Asp Ala Asp Gly Tyr Tyr His Ala Gln Cys
            260                 265                 270

Gln Asp Leu Ile Thr Asp Tyr Val Leu Trp Leu Thr Asp Asn Lys Val
        275                 280                 285

Arg Thr Trp Gly Asn Ala Lys Asp Gln Ile Lys Gln Ser Tyr Gly Thr
    290                 295                 300

Gly Phe Lys Ile His Glu Asn Lys Pro Ser Thr Val Pro Lys Lys Gly
305                 310                 315                 320

Trp Ile Ala Val Phe Thr Ser Gly Ser Tyr Glu Gln Trp Gly His Ile
                325                 330                 335

Gly Ile Val Tyr Asp Gly Gly Asn Thr Ser Thr Phe Thr Ile Leu Glu
            340                 345                 350

Gln Asn Trp Asn Gly Tyr Ala Asn Lys Lys Pro Thr Lys Arg Val Asp
        355                 360                 365

Asn Tyr Tyr Gly Leu Thr His Phe Ile Glu Ile Pro Val Lys Ala Gly
    370                 375                 380

Thr Thr Val Lys Lys Glu Thr Ala Lys Lys Ser Ala Ser Lys Thr Pro
385                 390                 395                 400

Ala Pro Lys Lys Lys Ala Thr Leu Lys Val Ser Lys Asn Gly Lys Ser
                405                 410                 415

Ala Ser Lys Ile Thr Val Gly Ser Lys Ala Pro Tyr Asn Leu Lys Trp
            420                 425                 430

Ser Lys Gly Ala Tyr Phe Asn Ala Lys Ile Asp Gly Leu Gly Ala Thr
        435                 440                 445

Ser Ala Thr Arg Tyr Gly Asp Asn Arg Thr Asn Tyr Arg Phe Asp Val
    450                 455                 460

Gly Gln Ala Val Tyr Ala Pro Gly Thr Leu Ile Tyr Val Phe Glu Ile
465                 470                 475                 480

Ile Asp Gly Trp Cys Arg Ile Tyr Trp Asn Asn His Asn Glu Trp Ile
                485                 490                 495

Trp His Glu Arg Leu Ile Val Lys Glu Val Phe
            500                 505


<210> SEQ ID NO 61
<211> LENGTH: 1446
<212> TYPE: DNA
<213> ORGANISM: artificial
<220> FEATURE:
<223> OTHER INFORMATION: artificial construct

<400> SEQUENCE: 61

atgagaggat cgcatcacca tcaccatcac ggatctggct ctggatctgg tatcgaggga      60

aggatgaaaa ccctgaaaca agcagagtcc tacattaaga gtaaagtaaa tacaggaact     120

gattttgatg gtttatatgg gtatcagtgt atggacttag cagtagatta tatttaccat     180

gtaacagatg gtaaaataag aatgtggggt aatgctaagg atgcgataaa taactctttt     240

ggtggtactg ctacggtata taaaaactac cctgctttta gacctaagta cggtgatgta     300
```

```
gtcgtatgga ctactggtaa ttttgcaact tatggtcata tcgcaatagt tactaaccct    360

gacccttatg gagaccttca atatgttaca gttcttgaac aaaactggaa cggtaacggg    420

atttataaaa ccgagttagc tacaatcaga acacacgatt acacaggaat tacacatttt    480

attagaccta actttgctac tgaatcaagt gtaaaaaaga aagatacaaa gaaaaaacca    540

aaaccatcaa atagagatgg aataaataaa gataaaattg tatatgatag aactaatatt    600

aattacaatg agctcatgaa aaccctgaaa caagcagagt cctacattaa gagtaaagta    660

aatacaggaa ctgattttga tggtttatat gggtatcagt gtatggactt agcagtagat    720

tatatttacc atgtaacaga tggtaaaata agaatgtggg gtaatgctaa ggatgcgata    780

aataactctt ttggtggtac tgctacggta tataaaaact accctgcttt tagacctaag    840

tacggtgatg tagtcgtatg gactactggt aattttgcaa cttatggtca tatcgcaata    900

gttactaacc ctgaccctta tggagacctt caatatgtta cagttcttga acaaaactgg    960

aacggtaacg ggatttataa aaccgagtta gctacaatca gaacacacga ttacacagga   1020

attacacatt ttattagacc taactttgct actgaatcaa gtgtaaaaaa gaaagataca   1080

aagaaaaaac caaaaccatc aaatagagat ggaataaata aagataaaat tgtatatgat   1140

agaactaata ttaattacaa ttggaaacag aataaagatg gcatttggta taaagctgaa   1200

catgcttcgt tcacagtgac agcaccagag ggaattatca caagatacaa aggtccttgg   1260

actggtcacc cacaagctgg tgtattacaa aaaggtcaaa cgattaaata tgatgaggtt   1320

caaaaatttg acggtcatgt ttgggtatcg tgggaaacgt ttgagggcga aactgtatac   1380

atgccggtac gcacatggga cgctaaaact ggtaaagttg gtaagttgtg gggcgaaatt   1440

aaataa                                                              1446
```

<210> SEQ ID NO 62
<211> LENGTH: 481
<212> TYPE: PRT
<213> ORGANISM: artificial
<220> FEATURE:
<223> OTHER INFORMATION: artificial construct

<400> SEQUENCE: 62

```
Met Arg Gly Ser His His His His His His Gly Ser Gly Ser Gly Ser
1               5                   10                  15

Gly Ile Glu Gly Arg Met Lys Thr Leu Lys Gln Ala Glu Ser Tyr Ile
            20                  25                  30

Lys Ser Lys Val Asn Thr Gly Thr Asp Phe Asp Gly Leu Tyr Gly Tyr
        35                  40                  45

Gln Cys Met Asp Leu Ala Val Asp Tyr Ile Tyr His Val Thr Asp Gly
    50                  55                  60

Lys Ile Arg Met Trp Gly Asn Ala Lys Asp Ala Ile Asn Asn Ser Phe
65                  70                  75                  80

Gly Gly Thr Ala Thr Val Tyr Lys Asn Tyr Pro Ala Phe Arg Pro Lys
                85                  90                  95

Tyr Gly Asp Val Val Val Trp Thr Thr Gly Asn Phe Ala Thr Tyr Gly
            100                 105                 110

His Ile Ala Ile Val Thr Asn Pro Asp Pro Tyr Gly Asp Leu Gln Tyr
        115                 120                 125

Val Thr Val Leu Glu Gln Asn Trp Asn Gly Asn Gly Ile Tyr Lys Thr
    130                 135                 140

Glu Leu Ala Thr Ile Arg Thr His Asp Tyr Thr Gly Ile Thr His Phe
145                 150                 155                 160
```

```
Ile Arg Pro Asn Phe Ala Thr Glu Ser Ser Val Lys Lys Lys Asp Thr
                165                 170                 175

Lys Lys Lys Pro Lys Pro Ser Asn Arg Asp Gly Ile Asn Lys Asp Lys
            180                 185                 190

Ile Val Tyr Asp Arg Thr Asn Ile Asn Tyr Asn Glu Leu Met Lys Thr
        195                 200                 205

Leu Lys Gln Ala Glu Ser Tyr Ile Lys Ser Lys Val Asn Thr Gly Thr
    210                 215                 220

Asp Phe Asp Gly Leu Tyr Gly Tyr Gln Cys Met Asp Leu Ala Val Asp
225                 230                 235                 240

Tyr Ile Tyr His Val Thr Asp Gly Lys Ile Arg Met Trp Gly Asn Ala
                245                 250                 255

Lys Asp Ala Ile Asn Asn Ser Phe Gly Gly Thr Ala Thr Val Tyr Lys
            260                 265                 270

Asn Tyr Pro Ala Phe Arg Pro Lys Tyr Gly Asp Val Val Val Trp Thr
        275                 280                 285

Thr Gly Asn Phe Ala Thr Tyr Gly His Ile Ala Ile Val Thr Asn Pro
    290                 295                 300

Asp Pro Tyr Gly Asp Leu Gln Tyr Val Thr Val Leu Glu Gln Asn Trp
305                 310                 315                 320

Asn Gly Asn Gly Ile Tyr Lys Thr Glu Leu Ala Thr Ile Arg Thr His
                325                 330                 335

Asp Tyr Thr Gly Ile Thr His Phe Ile Arg Pro Asn Phe Ala Thr Glu
            340                 345                 350

Ser Ser Val Lys Lys Lys Asp Thr Lys Lys Lys Pro Lys Pro Ser Asn
        355                 360                 365

Arg Asp Gly Ile Asn Lys Asp Lys Ile Val Tyr Asp Arg Thr Asn Ile
    370                 375                 380

Asn Tyr Asn Trp Lys Gln Asn Lys Asp Gly Ile Trp Tyr Lys Ala Glu
385                 390                 395                 400

His Ala Ser Phe Thr Val Thr Ala Pro Glu Gly Ile Ile Thr Arg Tyr
                405                 410                 415

Lys Gly Pro Trp Thr Gly His Pro Gln Ala Gly Val Leu Gln Lys Gly
            420                 425                 430

Gln Thr Ile Lys Tyr Asp Glu Val Gln Lys Phe Asp Gly His Val Trp
        435                 440                 445

Val Ser Trp Glu Thr Phe Glu Gly Glu Thr Val Tyr Met Pro Val Arg
    450                 455                 460

Thr Trp Asp Ala Lys Thr Gly Lys Val Gly Lys Leu Trp Gly Glu Ile
465                 470                 475                 480

Lys
```

<210> SEQ ID NO 63
<211> LENGTH: 1440
<212> TYPE: DNA
<213> ORGANISM: artificial
<220> FEATURE:
<223> OTHER INFORMATION: artificial construct

<400> SEQUENCE: 63

```
atgagaggat cgcatcacca tcaccatcac ggatctggct ctggatctgg tatcgaggga     60

aggatgaaaa ccctgaaaca agcagagtcc tacattaaga gtaaagtaaa tacaggaact    120

gattttgatg gtttatatgg gtatcagtgt atggacttag cagtagatta tatttaccat    180
```

```
gtaacagatg gtaaaataag aatgtggggt aatgctaagg atgcgataaa taactctttt    240
ggtggtactg ctacggtata taaaaactac cctgctttta gacctaagta cggtgatgta    300
gtcgtatgga ctactggtaa ttttgcaact tatggtcata tcgcaatagt tactaaccct    360
gacccttatg gagaccttca atatgttaca gttcttgaac aaaactggaa cggtaacggg    420
atttataaaa ccgagttagc tacaatcaga acacacgatt acacaggaat tacacatttt    480
attagaccta actttgctac tgaatcaagt gtaaaaaaga aagatacaaa gaaaaaacca    540
aaaccatcaa atagagatgg aataaataaa gataaaattg tatatgatag aactaatatt    600
aattacaatg agctcatgaa aaccctgaaa caagcagagt cctacattaa gagtaaagta    660
aatacaggaa ctgattttga tggtttatat gggtatcagt gtatggactt agcagtagat    720
tatatttacc atgtaacaga tggtaaaata agaatgtggg gtaatgctaa ggatgcgata    780
aataactctt ttggtggtac tgctacggta tataaaaact accctgcttt tagacctaag    840
tacggtgatg tagtcgtatg gactactggt aattttgcaa cttatggtca tatcgcaata    900
gttactaacc ctgaccctta tggagacctt caatatgtta cagttcttga acaaaactgg    960
aacggtaacg ggatttataa aaccgagtta gctacaatca gaacacacga ttacacagga   1020
attacacatt ttattagacc taactttgct actgaatcaa gtgtaaaaaa gaaagataca   1080
aagaaaaaac caaaaccatc aaatagagat ggaataaata aagataaaat tgtatatgat   1140
agaactaata ttaattacaa ttggaaaaca aacaaatatg gcacactata taaatcagag   1200
tcagctagct tcacacctaa tacagatata ataacaagaa cgactggtcc atttagaagc   1260
atgccgcagt caggagtctt aaaagcaggt caaacaattc attatgatga agtgatgaaa   1320
caagacggtc atgtttgggt aggttataca ggtaacagtg gccaacgtat ttacttgcct   1380
gtaagaacat ggaataaatc tactaatact ttaggtgttc tttggggaac tataaagtaa   1440
```

<210> SEQ ID NO 64
<211> LENGTH: 479
<212> TYPE: PRT
<213> ORGANISM: artificial
<220> FEATURE:
<223> OTHER INFORMATION: artificial construct

<400> SEQUENCE: 64

```
Met Arg Gly Ser His His His His His His Gly Ser Gly Ser Gly Ser
1               5                   10                  15

Gly Ile Glu Gly Arg Met Lys Thr Leu Lys Gln Ala Glu Ser Tyr Ile
            20                  25                  30

Lys Ser Lys Val Asn Thr Gly Thr Asp Phe Asp Gly Leu Tyr Gly Tyr
        35                  40                  45

Gln Cys Met Asp Leu Ala Val Asp Tyr Ile Tyr His Val Thr Asp Gly
    50                  55                  60

Lys Ile Arg Met Trp Gly Asn Ala Lys Asp Ala Ile Asn Asn Ser Phe
65                  70                  75                  80

Gly Gly Thr Ala Thr Val Tyr Lys Asn Tyr Pro Ala Phe Arg Pro Lys
                85                  90                  95

Tyr Gly Asp Val Val Val Trp Thr Thr Gly Asn Phe Ala Thr Tyr Gly
            100                 105                 110

His Ile Ala Ile Val Thr Asn Pro Asp Pro Tyr Gly Asp Leu Gln Tyr
        115                 120                 125

Val Thr Val Leu Glu Gln Asn Trp Asn Gly Asn Gly Ile Tyr Lys Thr
    130                 135                 140
```

```
Glu Leu Ala Thr Ile Arg Thr His Asp Tyr Thr Gly Ile Thr His Phe
145                 150                 155                 160

Ile Arg Pro Asn Phe Ala Thr Glu Ser Ser Val Lys Lys Lys Asp Thr
                165                 170                 175

Lys Lys Lys Pro Lys Pro Ser Asn Arg Asp Gly Ile Asn Lys Asp Lys
            180                 185                 190

Ile Val Tyr Asp Arg Thr Asn Ile Asn Tyr Asn Glu Leu Met Lys Thr
        195                 200                 205

Leu Lys Gln Ala Glu Ser Tyr Ile Lys Ser Lys Val Asn Thr Gly Thr
    210                 215                 220

Asp Phe Asp Gly Leu Tyr Gly Tyr Gln Cys Met Asp Leu Ala Val Asp
225                 230                 235                 240

Tyr Ile Tyr His Val Thr Asp Gly Lys Ile Arg Met Trp Gly Asn Ala
                245                 250                 255

Lys Asp Ala Ile Asn Asn Ser Phe Gly Gly Thr Ala Thr Val Tyr Lys
            260                 265                 270

Asn Tyr Pro Ala Phe Arg Pro Lys Tyr Gly Asp Val Val Val Trp Thr
        275                 280                 285

Thr Gly Asn Phe Ala Thr Tyr Gly His Ile Ala Ile Val Thr Asn Pro
    290                 295                 300

Asp Pro Tyr Gly Asp Leu Gln Tyr Val Thr Val Leu Glu Gln Asn Trp
305                 310                 315                 320

Asn Gly Asn Gly Ile Tyr Lys Thr Glu Leu Ala Thr Ile Arg Thr His
                325                 330                 335

Asp Tyr Thr Gly Ile Thr His Phe Ile Arg Pro Asn Phe Ala Thr Glu
            340                 345                 350

Ser Ser Val Lys Lys Lys Asp Thr Lys Lys Lys Pro Lys Pro Ser Asn
        355                 360                 365

Arg Asp Gly Ile Asn Lys Asp Lys Ile Val Tyr Asp Arg Thr Asn Ile
    370                 375                 380

Asn Tyr Asn Trp Lys Thr Asn Lys Tyr Gly Thr Leu Tyr Lys Ser Glu
385                 390                 395                 400

Ser Ala Ser Phe Thr Pro Asn Thr Asp Ile Ile Thr Arg Thr Thr Gly
                405                 410                 415

Pro Phe Arg Ser Met Pro Gln Ser Gly Val Leu Lys Ala Gly Gln Thr
            420                 425                 430

Ile His Tyr Asp Glu Val Met Lys Gln Asp Gly His Val Trp Val Gly
        435                 440                 445

Tyr Thr Gly Asn Ser Gly Gln Arg Ile Tyr Leu Pro Val Arg Thr Trp
    450                 455                 460

Asn Lys Ser Thr Asn Thr Leu Gly Val Leu Trp Gly Thr Ile Lys
465                 470                 475
```

```
<210> SEQ ID NO 65
<211> LENGTH: 1446
<212> TYPE: DNA
<213> ORGANISM: artificial
<220> FEATURE:
<223> OTHER INFORMATION: artificial construct

<400> SEQUENCE: 65

atgagaggat cgcatcacca tcaccatcac ggatctggct ctggatctgg tatcgaggga      60

aggatgaaaa ccctgaaaca agcagagtcc tacattaaga gtaaagtaaa tacaggaact     120

gattttgatg gtttatatgg gtatcagtgt atggacttag cagtagatta tatttaccat     180
```

```
gtaacagatg gtaaaataag aatgtggggt aatgctaagg atgcgataaa taactctttt    240

ggtggtactg ctacggtata taaaaactac cctgctttta gacctaagta cggtgatgta    300

gtcgtatgga ctactggtaa ttttgcaact tatggtcata tcgcaatagt tactaaccct    360

gacccttatg gagaccttca atatgttaca gttcttgaac aaaactggaa cggtaacggg    420

atttataaaa ccgagttagc tacaatcaga acacacgatt acacaggaat tacacatttt    480

attagaccta actttgctac tgaatcaagt gtaaaaaaga aagatacaaa gaaaaaacca    540

aaaccatcaa atagagatgg aataaataaa gataaaattg tatatgatag aactaatatt    600

aattacaatg agctcatgaa aaccctgaaa caagcagagt cctacattaa gagtaaagta    660

aatacaggaa ctgattttga tggtttatat gggtatcagt gtatggactt agcagtagat    720

tatatttacc atgtaacaga tggtaaaata agaatgtggg gtaatgctaa ggatgcgata    780

aataactctt ttggtggtac tgctacggta tataaaaact accctgcttt tagacctaag    840

tacggtgatg tagtcgtatg gactactggt aattttgcaa cttatggtca tatcgcaata    900

gttactaacc ctgaccctta tggagacctt caatatgtta cagttcttga acaaaactgg    960

aacggtaacg ggatttataa aaccgagtta gctacaatca gaacacacga ttacacagga   1020

attacacatt ttattagacc taactttgct actgaatcaa gtgtaaaaaa gaaagataca   1080

aagaaaaaac caaaaccatc aaatagagat ggaataaata aagataaaat tgtatatgat   1140

agaactaata ttaattacaa tggtaaatct gcaagtaaaa taacagttgg aagtaaagcg   1200

ccttataacc ttaaatggtc aaaaggtgct tattttaatg cgaaaatcga cggcttaggt   1260

gctacttcag ccactagata cggtgataat cgtactaact atagattcga tgttggacag   1320

gctgtatacg cgcctggaac attaatatat gtgtttgaaa ttatagatgg ttggtgtcgc   1380

atttattgga acaatcataa tgagtggata tggcatgaga gattgattgt gaaagaagtg   1440

ttttaa                                                              1446
```

```
<210> SEQ ID NO 66
<211> LENGTH: 481
<212> TYPE: PRT
<213> ORGANISM: artificial
<220> FEATURE:
<223> OTHER INFORMATION: artificial construct

<400> SEQUENCE: 66

Met Arg Gly Ser His His His His His His Gly Ser Gly Ser Gly Ser
1               5                   10                  15

Gly Ile Glu Gly Arg Met Lys Thr Leu Lys Gln Ala Glu Ser Tyr Ile
            20                  25                  30

Lys Ser Lys Val Asn Thr Gly Thr Asp Phe Asp Gly Leu Tyr Gly Tyr
        35                  40                  45

Gln Cys Met Asp Leu Ala Val Asp Tyr Ile Tyr His Val Thr Asp Gly
    50                  55                  60

Lys Ile Arg Met Trp Gly Asn Ala Lys Asp Ala Ile Asn Asn Ser Phe
65                  70                  75                  80

Gly Gly Thr Ala Thr Val Tyr Lys Asn Tyr Pro Ala Phe Arg Pro Lys
                85                  90                  95

Tyr Gly Asp Val Val Val Trp Thr Thr Gly Asn Phe Ala Thr Tyr Gly
            100                 105                 110

His Ile Ala Ile Val Thr Asn Pro Asp Pro Tyr Gly Asp Leu Gln Tyr
        115                 120                 125

Val Thr Val Leu Glu Gln Asn Trp Asn Gly Asn Gly Ile Tyr Lys Thr
```

```
    130                 135                 140

Glu Leu Ala Thr Ile Arg Thr His Asp Tyr Thr Gly Ile Thr His Phe
145                 150                 155                 160

Ile Arg Pro Asn Phe Ala Thr Glu Ser Ser Val Lys Lys Lys Asp Thr
                165                 170                 175

Lys Lys Lys Pro Lys Pro Ser Asn Arg Asp Gly Ile Asn Lys Asp Lys
            180                 185                 190

Ile Val Tyr Asp Arg Thr Asn Ile Asn Tyr Asn Glu Leu Met Lys Thr
        195                 200                 205

Leu Lys Gln Ala Glu Ser Tyr Ile Lys Ser Lys Val Asn Thr Gly Thr
    210                 215                 220

Asp Phe Asp Gly Leu Tyr Gly Tyr Gln Cys Met Asp Leu Ala Val Asp
225                 230                 235                 240

Tyr Ile Tyr His Val Thr Asp Gly Lys Ile Arg Met Trp Gly Asn Ala
                245                 250                 255

Lys Asp Ala Ile Asn Asn Ser Phe Gly Gly Thr Ala Thr Val Tyr Lys
            260                 265                 270

Asn Tyr Pro Ala Phe Arg Pro Lys Tyr Gly Asp Val Val Val Trp Thr
        275                 280                 285

Thr Gly Asn Phe Ala Thr Tyr Gly His Ile Ala Ile Val Thr Asn Pro
    290                 295                 300

Asp Pro Tyr Gly Asp Leu Gln Tyr Val Thr Val Leu Glu Gln Asn Trp
305                 310                 315                 320

Asn Gly Asn Gly Ile Tyr Lys Thr Glu Leu Ala Thr Ile Arg Thr His
                325                 330                 335

Asp Tyr Thr Gly Ile Thr His Phe Ile Arg Pro Asn Phe Ala Thr Glu
            340                 345                 350

Ser Ser Val Lys Lys Lys Asp Thr Lys Lys Lys Pro Lys Pro Ser Asn
        355                 360                 365

Arg Asp Gly Ile Asn Lys Asp Lys Ile Val Tyr Asp Arg Thr Asn Ile
    370                 375                 380

Asn Tyr Asn Gly Lys Ser Ala Ser Lys Ile Thr Val Gly Ser Lys Ala
385                 390                 395                 400

Pro Tyr Asn Leu Lys Trp Ser Lys Gly Ala Tyr Phe Asn Ala Lys Ile
                405                 410                 415

Asp Gly Leu Gly Ala Thr Ser Ala Thr Arg Tyr Gly Asp Asn Arg Thr
            420                 425                 430

Asn Tyr Arg Phe Asp Val Gly Gln Ala Val Tyr Ala Pro Gly Thr Leu
        435                 440                 445

Ile Tyr Val Phe Glu Ile Ile Asp Gly Trp Cys Arg Ile Tyr Trp Asn
    450                 455                 460

Asn His Asn Glu Trp Ile Trp His Glu Arg Leu Ile Val Lys Glu Val
465                 470                 475                 480

Phe


<210> SEQ ID NO 67
<211> LENGTH: 1278
<212> TYPE: DNA
<213> ORGANISM: artificial
<220> FEATURE:
<223> OTHER INFORMATION: artificial construct

<400> SEQUENCE: 67

atgagaggat cgcatcacca tcaccatcac ggatctggct ctggatctgg tatcgaggga      60
```

```
agggctgcaa cacatgaaca ttcagcacaa tggttgaata attacaaaaa aggatatggt    120

tacggtcctt atccattagg tataaatggc ggtatgcact acggagttga ttttttttatg    180

aatattggaa caccagtaaa agctatttca agcggaaaaa tagttgaagc tggttggagt    240

aattacggag gaggtaatca aataggtctt attgaaaatg atggagtgca tagacaatgg    300

tatatgcatc taagtaaata taatgttaaa gtaggagatt atgtcaaagc tggtcaaata    360

atcggttggt ctggaagcac tggttattct acagcaccac atttacactt ccaaagaatg    420

gttaattcat tttcaaattc aactgcccaa gatccaatgc ctttcttaaa gagcgcagga    480

tatggaaaag caggtggtac agtaactcca acgccgaata caggtgagct cgctgcaaca    540

catgaacatt cagcacaatg gttgaataat tacaaaaaag gatatggtta cggtccttat    600

ccattaggta taaatggcgg tatgcactac ggagttgatt tttttatgaa tattggaaca    660

ccagtaaaag ctatttcaag cggaaaaata gttgaagctg gttggagtaa ttacggagga    720

ggtaatcaaa taggtcttat tgaaaatgat ggagtgcata gacaatggta tatgcatcta    780

agtaaatata atgttaaagt aggagattat gtcaaagctg gtcaaataat cggttggtct    840

ggaagcactg gttattctac agcaccacat ttacacttcc aaagaatggt taattcattt    900

tcaaattcaa ctgcccaaga tccaatgcct ttcttaaaga gcgcaggata tggaaaagca    960

ggtggtacag taactccaac gccgaataca ggttggaaac agaataaaga tggcatttgg   1020

tataaagctg aacatgcttc gttcacagtg acagcaccag agggaattat cacaagatac   1080

aaaggtcctt ggactggtca cccacaagct ggtgtattac aaaaaggtca aacgattaaa   1140

tatgatgagg ttcaaaaatt tgacggtcat gtttgggtat cgtgggaaac gtttgagggc   1200

gaaactgtat acatgccggt acgcacatgg gacgctaaaa ctggtaaagt tggtaagttg   1260

tggggcgaaa ttaaataa                                                  1278
```

<210> SEQ ID NO 68
<211> LENGTH: 425
<212> TYPE: PRT
<213> ORGANISM: artificial
<220> FEATURE:
<223> OTHER INFORMATION: artificial construct

<400> SEQUENCE: 68

```
Met Arg Gly Ser His His His His His His Gly Ser Gly Ser Gly Ser
1               5                   10                  15

Gly Ile Glu Gly Arg Ala Ala Thr His Glu His Ser Ala Gln Trp Leu
            20                  25                  30

Asn Asn Tyr Lys Lys Gly Tyr Gly Tyr Gly Pro Tyr Pro Leu Gly Ile
        35                  40                  45

Asn Gly Gly Met His Tyr Gly Val Asp Phe Phe Met Asn Ile Gly Thr
    50                  55                  60

Pro Val Lys Ala Ile Ser Ser Gly Lys Ile Val Glu Ala Gly Trp Ser
65                  70                  75                  80

Asn Tyr Gly Gly Gly Asn Gln Ile Gly Leu Ile Glu Asn Asp Gly Val
                85                  90                  95

His Arg Gln Trp Tyr Met His Leu Ser Lys Tyr Asn Val Lys Val Gly
            100                 105                 110

Asp Tyr Val Lys Ala Gly Gln Ile Ile Gly Trp Ser Gly Ser Thr Gly
        115                 120                 125

Tyr Ser Thr Ala Pro His Leu His Phe Gln Arg Met Val Asn Ser Phe
    130                 135                 140
```

```
Ser Asn Ser Thr Ala Gln Asp Pro Met Pro Phe Leu Lys Ser Ala Gly
145                 150                 155                 160

Tyr Gly Lys Ala Gly Gly Thr Val Thr Pro Thr Pro Asn Thr Gly Glu
                165                 170                 175

Leu Ala Ala Thr His Glu His Ser Ala Gln Trp Leu Asn Asn Tyr Lys
            180                 185                 190

Lys Gly Tyr Gly Tyr Gly Pro Tyr Pro Leu Gly Ile Asn Gly Gly Met
        195                 200                 205

His Tyr Gly Val Asp Phe Phe Met Asn Ile Gly Thr Pro Val Lys Ala
    210                 215                 220

Ile Ser Ser Gly Lys Ile Val Glu Ala Gly Trp Ser Asn Tyr Gly Gly
225                 230                 235                 240

Gly Asn Gln Ile Gly Leu Ile Glu Asn Asp Gly Val His Arg Gln Trp
                245                 250                 255

Tyr Met His Leu Ser Lys Tyr Asn Val Lys Val Gly Asp Tyr Val Lys
            260                 265                 270

Ala Gly Gln Ile Ile Gly Trp Ser Gly Ser Thr Gly Tyr Ser Thr Ala
        275                 280                 285

Pro His Leu His Phe Gln Arg Met Val Asn Ser Phe Ser Asn Ser Thr
    290                 295                 300

Ala Gln Asp Pro Met Pro Phe Leu Lys Ser Ala Gly Tyr Gly Lys Ala
305                 310                 315                 320

Gly Gly Thr Val Thr Pro Thr Pro Asn Thr Gly Trp Lys Gln Asn Lys
                325                 330                 335

Asp Gly Ile Trp Tyr Lys Ala Glu His Ala Ser Phe Thr Val Thr Ala
            340                 345                 350

Pro Glu Gly Ile Ile Thr Arg Tyr Lys Gly Pro Trp Thr Gly His Pro
        355                 360                 365

Gln Ala Gly Val Leu Gln Lys Gly Gln Thr Ile Lys Tyr Asp Glu Val
    370                 375                 380

Gln Lys Phe Asp Gly His Val Trp Val Ser Trp Glu Thr Phe Glu Gly
385                 390                 395                 400

Glu Thr Val Tyr Met Pro Val Arg Thr Trp Asp Ala Lys Thr Gly Lys
                405                 410                 415

Val Gly Lys Leu Trp Gly Glu Ile Lys
            420                 425


<210> SEQ ID NO 69
<211> LENGTH: 1272
<212> TYPE: DNA
<213> ORGANISM: artificial
<220> FEATURE:
<223> OTHER INFORMATION: artificial construct

<400> SEQUENCE: 69

atgagaggat cgcatcacca tcaccatcac ggatctggct ctggatctgg tatcgaggga      60

agggctgcaa cacatgaaca ttcagcacaa tggttgaata attacaaaaa aggatatggt     120

tacggtcctt atccattagg tataaatggc ggtatgcact acggagttga tttttttatg     180

aatattggaa caccagtaaa agctatttca agcggaaaaa tagttgaagc tggttggagt     240

aattacggag gaggtaatca aataggtctt attgaaaatg atggagtgca tagacaatgg     300

tatatgcatc taagtaaata taatgttaaa gtaggagatt atgtcaaagc tggtcaaata     360

atcggttggt ctggaagcac tggttattct acagcaccac atttacactt ccaaagaatg     420

gttaattcat tttcaaattc aactgcccaa gatccaatgc ctttcttaaa gagcgcagga     480
```

```
tatggaaaag caggtggtac agtaactcca acgccgaata caggtgagct cgctgcaaca    540

catgaacatt cagcacaatg gttgaataat tacaaaaaag gatatggtta cggtccttat    600

ccattaggta taaatggcgg tatgcactac ggagttgatt tttttatgaa tattggaaca    660

ccagtaaaag ctatttcaag cggaaaaata gttgaagctg gttggagtaa ttacggagga    720

ggtaatcaaa taggtcttat tgaaaatgat ggagtgcata gacaatggta tatgcatcta    780

agtaaatata atgttaaagt aggagattat gtcaaagctg gtcaaataat cggttggtct    840

ggaagcactg gttattctac agcaccacat ttacacttcc aaagaatggt taattcattt    900

tcaaattcaa ctgcccaaga tccaatgcct ttcttaaaga gcgcaggata tggaaaagca    960

ggtggtacag taactccaac gccgaataca ggttggaaaa caaacaaata tggcacacta   1020

tataaatcag agtcagctag cttcacacct aatacagata taataacaag aacgactggt   1080

ccatttagaa gcatgccgca gtcaggagtc ttaaaagcag gtcaaacaat tcattatgat   1140

gaagtgatga aacaagacgg tcatgtttgg gtaggttata caggtaacag tggccaacgt   1200

atttacttgc ctgtaagaac atggaataaa tctactaata ctttaggtgt tctttgggga   1260

actataaagt aa                                                       1272
```

```
<210> SEQ ID NO 70
<211> LENGTH: 423
<212> TYPE: PRT
<213> ORGANISM: artificial
<220> FEATURE:
<223> OTHER INFORMATION: artificial construct

<400> SEQUENCE: 70

Met Arg Gly Ser His His His His His His Gly Ser Gly Ser Gly Ser
1               5                   10                  15

Gly Ile Glu Gly Arg Ala Ala Thr His Glu His Ser Ala Gln Trp Leu
            20                  25                  30

Asn Asn Tyr Lys Lys Gly Tyr Gly Tyr Gly Pro Tyr Pro Leu Gly Ile
        35                  40                  45

Asn Gly Gly Met His Tyr Gly Val Asp Phe Phe Met Asn Ile Gly Thr
    50                  55                  60

Pro Val Lys Ala Ile Ser Ser Gly Lys Ile Val Glu Ala Gly Trp Ser
65                  70                  75                  80

Asn Tyr Gly Gly Gly Asn Gln Ile Gly Leu Ile Glu Asn Asp Gly Val
                85                  90                  95

His Arg Gln Trp Tyr Met His Leu Ser Lys Tyr Asn Val Lys Val Gly
            100                 105                 110

Asp Tyr Val Lys Ala Gly Gln Ile Ile Gly Trp Ser Gly Ser Thr Gly
        115                 120                 125

Tyr Ser Thr Ala Pro His Leu His Phe Gln Arg Met Val Asn Ser Phe
    130                 135                 140

Ser Asn Ser Thr Ala Gln Asp Pro Met Pro Phe Leu Lys Ser Ala Gly
145                 150                 155                 160

Tyr Gly Lys Ala Gly Gly Thr Val Thr Pro Thr Pro Asn Thr Gly Glu
                165                 170                 175

Leu Ala Ala Thr His Glu His Ser Ala Gln Trp Leu Asn Asn Tyr Lys
            180                 185                 190

Lys Gly Tyr Gly Tyr Gly Pro Tyr Pro Leu Gly Ile Asn Gly Gly Met
        195                 200                 205

His Tyr Gly Val Asp Phe Phe Met Asn Ile Gly Thr Pro Val Lys Ala
```

```
    210                 215                 220

Ile Ser Ser Gly Lys Ile Val Glu Ala Gly Trp Ser Asn Tyr Gly Gly
225                 230                 235                 240

Gly Asn Gln Ile Gly Leu Ile Glu Asn Asp Gly Val His Arg Gln Trp
                245                 250                 255

Tyr Met His Leu Ser Lys Tyr Asn Val Lys Val Gly Asp Tyr Val Lys
            260                 265                 270

Ala Gly Gln Ile Ile Gly Trp Ser Gly Ser Thr Gly Tyr Ser Thr Ala
        275                 280                 285

Pro His Leu His Phe Gln Arg Met Val Asn Ser Phe Ser Asn Ser Thr
    290                 295                 300

Ala Gln Asp Pro Met Pro Phe Leu Lys Ser Ala Gly Tyr Gly Lys Ala
305                 310                 315                 320

Gly Gly Thr Val Thr Pro Thr Pro Asn Thr Gly Trp Lys Thr Asn Lys
                325                 330                 335

Tyr Gly Thr Leu Tyr Lys Ser Glu Ser Ala Ser Phe Thr Pro Asn Thr
            340                 345                 350

Asp Ile Ile Thr Arg Thr Thr Gly Pro Phe Arg Ser Met Pro Gln Ser
        355                 360                 365

Gly Val Leu Lys Ala Gly Gln Thr Ile His Tyr Asp Glu Val Met Lys
    370                 375                 380

Gln Asp Gly His Val Trp Val Gly Tyr Thr Gly Asn Ser Gly Gln Arg
385                 390                 395                 400

Ile Tyr Leu Pro Val Arg Thr Trp Asn Lys Ser Thr Asn Thr Leu Gly
                405                 410                 415

Val Leu Trp Gly Thr Ile Lys
            420
```

<210> SEQ ID NO 71
<211> LENGTH: 1278
<212> TYPE: DNA
<213> ORGANISM: artificial
<220> FEATURE:
<223> OTHER INFORMATION: artificial construct

<400> SEQUENCE: 71

```
atgagaggat cgcatcacca tcaccatcac ggatctggct ctggatctgg tatcgaggga     60

agggctgcaa cacatgaaca ttcagcacaa tggttgaata attacaaaaa aggatatggt    120

tacggtcctt atccattagg tataaatggc ggtatgcact acggagttga tttttttatg    180

aatattggaa caccagtaaa agctatttca agcggaaaaa tagttgaagc tggttggagt    240

aattacggag gaggtaatca aataggtctt attgaaaatg atggagtgca tagacaatgg    300

tatatgcatc taagtaaata taatgttaaa gtaggagatt atgtcaaagc tggtcaaata    360

atcggttggt ctggaagcac tggttattct acagcaccac atttacactt ccaaagaatg    420

gttaattcat tttcaaattc aactgcccaa gatccaatgc ctttcttaaa gagcgcagga    480

tatggaaaag caggtggtac agtaactcca acgccgaata caggtgagct cgctgcaaca    540

catgaacatt cagcacaatg gttgaataat tacaaaaaag gatatggtta cggtccttat    600

ccattaggta taaatggcgg tatgcactac ggagttgatt tttttatgaa tattggaaca    660

ccagtaaaag ctatttcaag cggaaaaata gttgaagctg gttggagtaa ttacggagga    720

ggtaatcaaa taggtcttat tgaaaatgat ggagtgcata gacaatggta tatgcatcta    780

agtaaatata atgttaaagt aggagattat gtcaaagctg gtcaaataat cggttggtct    840
```

```
ggaagcactg gttattctac agcaccacat ttacacttcc aaagaatggt taattcattt    900

tcaaattcaa ctgcccaaga tccaatgcct ttcttaaaga gcgcaggata tggaaaagca    960

ggtggtacag taactccaac gccgaataca ggtggtaaat ctgcaagtaa aataacagtt   1020

ggaagtaaag cgccttataa ccttaaatgg tcaaaaggtg cttattttaa tgcgaaaatc   1080

gacggcttag gtgctacttc agccactaga tacggtgata atcgtactaa ctatagattc   1140

gatgttggac aggctgtata cgcgcctgga acattaatat atgtgtttga aattatagat   1200

ggttggtgtc gcatttattg gaacaatcat aatgagtgga tatggcatga gagattgatt   1260

gtgaaagaag tgttttaa                                                 1278
```

<210> SEQ ID NO 72
<211> LENGTH: 425
<212> TYPE: PRT
<213> ORGANISM: artificial
<220> FEATURE:
<223> OTHER INFORMATION: artificial construct

<400> SEQUENCE: 72

```
Met Arg Gly Ser His His His His His His Gly Ser Gly Ser Gly Ser
1               5                   10                  15

Gly Ile Glu Gly Arg Ala Ala Thr His Glu His Ser Ala Gln Trp Leu
            20                  25                  30

Asn Asn Tyr Lys Lys Gly Tyr Gly Tyr Gly Pro Tyr Pro Leu Gly Ile
        35                  40                  45

Asn Gly Gly Met His Tyr Gly Val Asp Phe Phe Met Asn Ile Gly Thr
    50                  55                  60

Pro Val Lys Ala Ile Ser Ser Gly Lys Ile Val Glu Ala Gly Trp Ser
65                  70                  75                  80

Asn Tyr Gly Gly Gly Asn Gln Ile Gly Leu Ile Glu Asn Asp Gly Val
                85                  90                  95

His Arg Gln Trp Tyr Met His Leu Ser Lys Tyr Asn Val Lys Val Gly
            100                 105                 110

Asp Tyr Val Lys Ala Gly Gln Ile Ile Gly Trp Ser Gly Ser Thr Gly
        115                 120                 125

Tyr Ser Thr Ala Pro His Leu His Phe Gln Arg Met Val Asn Ser Phe
    130                 135                 140

Ser Asn Ser Thr Ala Gln Asp Pro Met Pro Phe Leu Lys Ser Ala Gly
145                 150                 155                 160

Tyr Gly Lys Ala Gly Gly Thr Val Thr Pro Thr Pro Asn Thr Gly Glu
                165                 170                 175

Leu Ala Ala Thr His Glu His Ser Ala Gln Trp Leu Asn Asn Tyr Lys
            180                 185                 190

Lys Gly Tyr Gly Tyr Gly Pro Tyr Pro Leu Gly Ile Asn Gly Gly Met
        195                 200                 205

His Tyr Gly Val Asp Phe Phe Met Asn Ile Gly Thr Pro Val Lys Ala
    210                 215                 220

Ile Ser Ser Gly Lys Ile Val Glu Ala Gly Trp Ser Asn Tyr Gly Gly
225                 230                 235                 240

Gly Asn Gln Ile Gly Leu Ile Glu Asn Asp Gly Val His Arg Gln Trp
                245                 250                 255

Tyr Met His Leu Ser Lys Tyr Asn Val Lys Val Gly Asp Tyr Val Lys
            260                 265                 270

Ala Gly Gln Ile Ile Gly Trp Ser Gly Ser Thr Gly Tyr Ser Thr Ala
        275                 280                 285
```

```
Pro His Leu His Phe Gln Arg Met Val Asn Ser Phe Ser Asn Ser Thr
    290                 295                 300

Ala Gln Asp Pro Met Pro Phe Leu Lys Ser Ala Gly Tyr Gly Lys Ala
305                 310                 315                 320

Gly Gly Thr Val Thr Pro Thr Pro Asn Thr Gly Gly Lys Ser Ala Ser
                325                 330                 335

Lys Ile Thr Val Gly Ser Lys Ala Pro Tyr Asn Leu Lys Trp Ser Lys
            340                 345                 350

Gly Ala Tyr Phe Asn Ala Lys Ile Asp Gly Leu Gly Ala Thr Ser Ala
        355                 360                 365

Thr Arg Tyr Gly Asp Asn Arg Thr Asn Tyr Arg Phe Asp Val Gly Gln
    370                 375                 380

Ala Val Tyr Ala Pro Gly Thr Leu Ile Tyr Val Phe Glu Ile Ile Asp
385                 390                 395                 400

Gly Trp Cys Arg Ile Tyr Trp Asn Asn His Asn Glu Trp Ile Trp His
                405                 410                 415

Glu Arg Leu Ile Val Lys Glu Val Phe
            420                 425


<210> SEQ ID NO 73
<211> LENGTH: 63
<212> TYPE: DNA
<213> ORGANISM: artificial
<220> FEATURE:
<223> OTHER INFORMATION: artificial his-tag

<400> SEQUENCE: 73

atgagaggat cgcatcacca tcaccatcac ggatctggct ctggatctgg tatcgaggga      60

agg                                                                    63


<210> SEQ ID NO 74
<211> LENGTH: 21
<212> TYPE: PRT
<213> ORGANISM: artificial
<220> FEATURE:
<223> OTHER INFORMATION: artificial Hist-tag

<400> SEQUENCE: 74

Met Arg Gly Ser His His His His His His Gly Ser Gly Ser Gly Ser
1               5                   10                  15

Gly Ile Glu Gly Arg
            20


<210> SEQ ID NO 75
<211> LENGTH: 741
<212> TYPE: DNA
<213> ORGANISM: Staphylococcus simulans

<400> SEQUENCE: 75

gctgcaacac atgaacattc agcacaatgg ttgaataatt acaaaaaagg atatggttac      60

ggtccttatc cattaggtat aaatggcggt atgcactacg gagttgattt ttttatgaat     120

attggaacac cagtaaaagc tatttcaagc ggaaaaatag ttgaagctgg ttggagtaat     180

tacggaggag gtaatcaaat aggtcttatt gaaaatgatg gagtgcatag acaatggtat     240

atgcatctaa gtaaatataa tgttaaagta ggagattatg tcaaagctgg tcaaataatc     300

ggttggtctg gaagcactgg ttattctaca gcaccacatt tacacttcca aagaatggtt     360

aattcatttt caaattcaac tgcccaagat ccaatgcctt tcttaaagag cgcaggatat     420
```

```
ggaaaagcag gtggtacagt aactccaacg ccgaatacag gttggaaaac aaacaaatat    480

ggcacactat ataaatcaga gtcagctagc ttcacaccta atacagatat aataacaaga    540

acgactggtc catttagaag catgccgcag tcaggagtct taaaagcagg tcaaacaatt    600

cattatgatg aagtgatgaa acaagacggt catgtttggg taggttatac aggtaacagt    660

ggccaacgta tttacttgcc tgtaagaaca tggaataaat ctactaatac tttaggtgtt    720

ctttggggaa ctataaagtg a                                              741
```

<210> SEQ ID NO 76
<211> LENGTH: 246
<212> TYPE: PRT
<213> ORGANISM: Staphylococcus simulans

<400> SEQUENCE: 76

```
Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Ile Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Ser Phe Ser Asn Ser Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245
```

<210> SEQ ID NO 77
<211> LENGTH: 2019
<212> TYPE: DNA
<213> ORGANISM: artificial
<220> FEATURE:
<223> OTHER INFORMATION: artificial construct

<400> SEQUENCE: 77

```
atgagaggat cgcatcacca tcaccatcac ggatccatgc aagcaaaatt aactaaaaat     60
gagtttatag agtggttgaa aacttctgag ggaaaacaat tcaatgtgga cttatggtat    120
ggatttcaat gctttgatta tgccaatgct ggttggaaag ttttgtttgg attacttcta    180
aaaggtttag gtgcaaaaga tattccgttc gctaacaact tcgacggatt agctactgta    240
taccaaaata caccggactt cttagcacaa cctggcgaca tggtggtatt cggtagcaac    300
tacggtgctg gatatggtca cgttgcatgg gtaattgaag caactttaga ttacatcatt    360
gtatatgagc agaattggct aggcggtggc tggactgacg gaatcgaaca acccggctgg    420
ggttgggaaa aagttacaag acgacaacat gcttatgatt tccctatgtg gtttatccgt    480
ccgaatttta aaagtgagac agcgccacga tcagttcaat ctcctacaca agcacctaaa    540
aaagaaacag ctggatccat gctaactgct attgactatc ttacgaaaaa aggttggaaa    600
atatcatctg accctcgcac ttacgatggt taccctaaaa actacggcta cagaaattac    660
catgaaaacg gcattaatta tgatgagttt tgtggtggtt atcatagagc ttttgatgtt    720
tacagtaacg aaactaacga cgtgcctgct gttactagcg gaacagttat tgaagcaaac    780
gattacggta attttggtgg tacattcgtt attagagacg ctaacgataa cgattggata    840
tatgggcatc tacaacgtgg ctcaatgcga tttgttgtag gcgacaaagt caatcaaggt    900
gacattattg gtttacaagg taatagcaac tattacgaca atcctatgag tgtacattta    960
catttacaat tacgccctaa agacgcaaag aaagatgaaa aatcacaagt atgtagtggt   1020
ttggctatgg aaaaatatga cattacaaat ttaaatgcta aacaagataa atcaaagaat   1080
gggagcgtga aagagttgaa acatatctat tcaaaccata ttaaaggtaa caagattaca   1140
gcaccaaaac ctagtattca aggtgtggtc atccacaatg attatggtag tatgacacct   1200
agtcaatact taccatggtt atatgcacgt gagaataacg gtacacacgt taacggttgg   1260
gctagtgttt atgcaaatag aaacgaagtg ctttggtatc atccgacaga ctacgtagag   1320
tggcattgtg gtaatcaatg ggcaaatgct aacttaatcg gatttgaagt gtgtgagtcg   1380
tatcctggta gaatctcgga caaattattc ttagaaaatg aagaagcgac attgaaagta   1440
gctgcggatg tgatgaagtc gtacggatta ccagttaatc gcaacactgt acgtctgcat   1500
aacgaattct tcggaacttc ttgtccacat cgttcgtggg acttgcatgt tggcaaaggt   1560
gagccttaca caactactaa tattaataaa atgaaagact acttcatcaa acgcatcaaa   1620
cattattatg acggtggaaa gctagaagta agcaaagcag caactatcaa acaatctgac   1680
gttaagcaag aagttaaaaa gcaagaagca aaacaaattg tgaaagcaac agattggaaa   1740
cagaataaag atggcatttg gtataaagct gaacatgctt cgttcacagt gacagcacca   1800
gagggaatta tcacaagata caaaggtcct tggactggtc acccacaagc tggtgtatta   1860
caaaaaggtc aaacgattaa atatgatgag gttcaaaaat ttgacggtca tgtttgggta   1920
tcgtgggaaa cgtttgaggg cgaaactgta tacatgccgg tacgcacatg ggacgctaaa   1980
actggtaaag ttggtaagtt gtggggcgaa attaaataa                          2019
```

<210> SEQ ID NO 78
<211> LENGTH: 672
<212> TYPE: PRT
<213> ORGANISM: artificial
<220> FEATURE:
<223> OTHER INFORMATION: artificial construct

<400> SEQUENCE: 78

Met Arg Gly Ser His His His His His His Gly Ser Met Gln Ala Lys

```
1               5                   10                  15

Leu Thr Lys Asn Glu Phe Ile Glu Trp Leu Lys Thr Ser Glu Gly Lys
            20                  25                  30

Gln Phe Asn Val Asp Leu Trp Tyr Gly Phe Gln Cys Phe Asp Tyr Ala
        35                  40                  45

Asn Ala Gly Trp Lys Val Leu Phe Gly Leu Leu Leu Lys Gly Leu Gly
    50                  55                  60

Ala Lys Asp Ile Pro Phe Ala Asn Asn Phe Asp Gly Leu Ala Thr Val
65                  70                  75                  80

Tyr Gln Asn Thr Pro Asp Phe Leu Ala Gln Pro Gly Asp Met Val Val
                85                  90                  95

Phe Gly Ser Asn Tyr Gly Ala Gly Tyr Gly His Val Ala Trp Val Ile
            100                 105                 110

Glu Ala Thr Leu Asp Tyr Ile Ile Val Tyr Glu Gln Asn Trp Leu Gly
        115                 120                 125

Gly Gly Trp Thr Asp Gly Ile Glu Gln Pro Gly Trp Gly Trp Glu Lys
    130                 135                 140

Val Thr Arg Arg Gln His Ala Tyr Asp Phe Pro Met Trp Phe Ile Arg
145                 150                 155                 160

Pro Asn Phe Lys Ser Glu Thr Ala Pro Arg Ser Val Gln Ser Pro Thr
                165                 170                 175

Gln Ala Pro Lys Lys Glu Thr Ala Gly Ser Met Leu Thr Ala Ile Asp
            180                 185                 190

Tyr Leu Thr Lys Lys Gly Trp Lys Ile Ser Ser Asp Pro Arg Thr Tyr
        195                 200                 205

Asp Gly Tyr Pro Lys Asn Tyr Gly Tyr Arg Asn Tyr His Glu Asn Gly
    210                 215                 220

Ile Asn Tyr Asp Glu Phe Cys Gly Gly Tyr His Arg Ala Phe Asp Val
225                 230                 235                 240

Tyr Ser Asn Glu Thr Asn Asp Val Pro Ala Val Thr Ser Gly Thr Val
                245                 250                 255

Ile Glu Ala Asn Asp Tyr Gly Asn Phe Gly Gly Thr Phe Val Ile Arg
            260                 265                 270

Asp Ala Asn Asp Asn Asp Trp Ile Tyr Gly His Leu Gln Arg Gly Ser
        275                 280                 285

Met Arg Phe Val Val Gly Asp Lys Val Asn Gln Gly Asp Ile Ile Gly
    290                 295                 300

Leu Gln Gly Asn Ser Asn Tyr Tyr Asp Asn Pro Met Ser Val His Leu
305                 310                 315                 320

His Leu Gln Leu Arg Pro Lys Asp Ala Lys Lys Asp Glu Lys Ser Gln
                325                 330                 335

Val Cys Ser Gly Leu Ala Met Glu Lys Tyr Asp Ile Thr Asn Leu Asn
            340                 345                 350

Ala Lys Gln Asp Lys Ser Lys Asn Gly Ser Val Lys Glu Leu Lys His
        355                 360                 365

Ile Tyr Ser Asn His Ile Lys Gly Asn Lys Ile Thr Ala Pro Lys Pro
    370                 375                 380

Ser Ile Gln Gly Val Val Ile His Asn Asp Tyr Gly Ser Met Thr Pro
385                 390                 395                 400

Ser Gln Tyr Leu Pro Trp Leu Tyr Ala Arg Glu Asn Asn Gly Thr His
                405                 410                 415

Val Asn Gly Trp Ala Ser Val Tyr Ala Asn Arg Asn Glu Val Leu Trp
            420                 425                 430
```

```
Tyr His Pro Thr Asp Tyr Val Glu Trp His Cys Gly Asn Gln Trp Ala
        435                 440                 445

Asn Ala Asn Leu Ile Gly Phe Glu Val Cys Glu Ser Tyr Pro Gly Arg
    450                 455                 460

Ile Ser Asp Lys Leu Phe Leu Glu Asn Glu Glu Ala Thr Leu Lys Val
465                 470                 475                 480

Ala Ala Asp Val Met Lys Ser Tyr Gly Leu Pro Val Asn Arg Asn Thr
                485                 490                 495

Val Arg Leu His Asn Glu Phe Phe Gly Thr Ser Cys Pro His Arg Ser
            500                 505                 510

Trp Asp Leu His Val Gly Lys Gly Glu Pro Tyr Thr Thr Thr Asn Ile
        515                 520                 525

Asn Lys Met Lys Asp Tyr Phe Ile Lys Arg Ile Lys His Tyr Tyr Asp
    530                 535                 540

Gly Gly Lys Leu Glu Val Ser Lys Ala Ala Thr Ile Lys Gln Ser Asp
545                 550                 555                 560

Val Lys Gln Glu Val Lys Lys Gln Glu Ala Lys Gln Ile Val Lys Ala
                565                 570                 575

Thr Asp Trp Lys Gln Asn Lys Asp Gly Ile Trp Tyr Lys Ala Glu His
            580                 585                 590

Ala Ser Phe Thr Val Thr Ala Pro Glu Gly Ile Ile Thr Arg Tyr Lys
        595                 600                 605

Gly Pro Trp Thr Gly His Pro Gln Ala Gly Val Leu Gln Lys Gly Gln
    610                 615                 620

Thr Ile Lys Tyr Asp Glu Val Gln Lys Phe Asp Gly His Val Trp Val
625                 630                 635                 640

Ser Trp Glu Thr Phe Glu Gly Glu Thr Val Tyr Met Pro Val Arg Thr
                645                 650                 655

Trp Asp Ala Lys Thr Gly Lys Val Gly Lys Leu Trp Gly Glu Ile Lys
            660                 665                 670
```

<210> SEQ ID NO 79
<211> LENGTH: 2145
<212> TYPE: DNA
<213> ORGANISM: artificial
<220> FEATURE:
<223> OTHER INFORMATION: artificial construct

<400> SEQUENCE: 79

```
atgagaggat cgcatcacca tcaccatcac ggatccaagc cacaacctaa agcagtagaa     60

cttaaaatca tcaaagatgt ggttaaaggt tatgacctac ctaagcgtgg tagtaaccct    120

aaaggtatag ttatacacaa cgacgcaggg agcaaagggg cgactgctga agcatatcgt    180

aacggattag taaatgcacc tttatcaaga ttagaagcgg gcattgcgca tagttacgta    240

tcaggcaaca cagtttggca agccttagat gaatcacaag taggttggca taccgctaat    300

caaataggta ataaatatta ttacggtatt gaagtatgtc aatcaatggg cgcagataac    360

gcgacattct taaaaaatga acaggcaact ttccaagaat gcgctagatt gttgaaaaaa    420

tggggattac cagcaaacag aaatacaatc agattgcaca atgaatttac ttcaacatca    480

tgccctcata gaagttcggt tttacacact ggttttgacc cagtaactcg cggtctattg    540

ccagaagaca agcggttgca acttaaagac tactttatca agcagattag ggcgtacatg    600

gatggtaaaa taccggttgc cactgtctct aatgagtcaa gcgcttcaag taatacagtt    660

aaaccagttg caagtgcagg atccatgcta actgctattg actatcttac gaaaaaaggt    720
```

```
tggaaaatat catctgaccc tcgcacttac gatggttacc ctaaaaacta cggctacaga    780

aattaccatg aaaacggcat taattatgat gagttttgtg gtggttatca tagagctttt    840

gatgtttaca gtaacgaaac taacgacgtg cctgctgtta ctagcggaac agttattgaa    900

gcaaacgatt acggtaattt tggtggtaca ttcgttatta gagacgctaa cgataacgat    960

tggatatatg ggcatctaca acgtggctca atgcgatttg ttgtaggcga caaagtcaat   1020

caaggtgaca ttattggttt acaaggtaat agcaactatt acgacaatcc tatgagtgta   1080

catttacatt tacaattacg ccctaaagac gcaaagaaag atgaaaaatc acaagtatgt   1140

agtggtttgg ctatggaaaa atatgacatt acaaatttaa atgctaaaca agataaatca   1200

aagaatggga gcgtgaaaga gttgaaacat atctattcaa accatattaa aggtaacaag   1260

attacagcac caaaacctag tattcaaggt gtggtcatcc acaatgatta tggtagtatg   1320

acacctagtc aatacttacc atggttatat gcacgtgaga ataacggtac acacgttaac   1380

ggttgggcta gtgtttatgc aaatagaaac gaagtgcttt ggtatcatcc gacagactac   1440

gtagagtggc attgtggtaa tcaatgggca aatgctaact taatcggatt tgaagtgtgt   1500

gagtcgtatc ctggtagaat ctcggacaaa ttattcttag aaaatgaaga agcgacattg   1560

aaagtagctg cggatgtgat gaagtcgtac ggattaccag ttaatcgcaa cactgtacgt   1620

ctgcataacg aattcttcgg aacttcttgt ccacatcgtt cgtgggactt gcatgttggc   1680

aaaggtgagc cttacacaac tactaatatt aataaaatga aagactactt catcaaacgc   1740

atcaaacatt attatgacgg tggaaagcta gaagtaagca aagcagcaac tatcaaacaa   1800

tctgacgtta agcaagaagt taaaaagcaa gaagcaaaac aaattgtgaa agcaacagat   1860

tggaaacaga ataaagatgg catttggtat aaagctgaac atgcttcgtt cacagtgaca   1920

gcaccagagg gaattatcac aagatacaaa ggtccttgga ctggtcaccc acaagctggt   1980

gtattacaaa aggtcaaac gattaaatat gatgaggttc aaaaatttga cggtcatgtt    2040

tgggtatcgt gggaaacgtt tgagggcgaa actgtataca tgccggtacg cacatgggac   2100

gctaaaactg gtaaagttgg taagttgtgg ggcgaaatta aataa                   2145
```

<210> SEQ ID NO 80
<211> LENGTH: 714
<212> TYPE: PRT
<213> ORGANISM: artificial
<220> FEATURE:
<223> OTHER INFORMATION: artificial construct

<400> SEQUENCE: 80

```
Met Arg Gly Ser His His His His His His Gly Ser Lys Pro Gln Pro
1               5                   10                  15

Lys Ala Val Glu Leu Lys Ile Ile Lys Asp Val Val Lys Gly Tyr Asp
            20                  25                  30

Leu Pro Lys Arg Gly Ser Asn Pro Lys Gly Ile Val Ile His Asn Asp
        35                  40                  45

Ala Gly Ser Lys Gly Ala Thr Ala Glu Ala Tyr Arg Asn Gly Leu Val
    50                  55                  60

Asn Ala Pro Leu Ser Arg Leu Glu Ala Gly Ile Ala His Ser Tyr Val
65                  70                  75                  80

Ser Gly Asn Thr Val Trp Gln Ala Leu Asp Glu Ser Gln Val Gly Trp
                85                  90                  95

His Thr Ala Asn Gln Ile Gly Asn Lys Tyr Tyr Tyr Gly Ile Glu Val
            100                 105                 110
```

```
Cys Gln Ser Met Gly Ala Asp Asn Ala Thr Phe Leu Lys Asn Glu Gln
        115                 120                 125

Ala Thr Phe Gln Glu Cys Ala Arg Leu Leu Lys Lys Trp Gly Leu Pro
    130                 135                 140

Ala Asn Arg Asn Thr Ile Arg Leu His Asn Glu Phe Thr Ser Thr Ser
145                 150                 155                 160

Cys Pro His Arg Ser Ser Val Leu His Thr Gly Phe Asp Pro Val Thr
                165                 170                 175

Arg Gly Leu Leu Pro Glu Asp Lys Arg Leu Gln Leu Lys Asp Tyr Phe
            180                 185                 190

Ile Lys Gln Ile Arg Ala Tyr Met Asp Gly Lys Ile Pro Val Ala Thr
        195                 200                 205

Val Ser Asn Glu Ser Ser Ala Ser Ser Asn Thr Val Lys Pro Val Ala
    210                 215                 220

Ser Ala Gly Ser Met Leu Thr Ala Ile Asp Tyr Leu Thr Lys Lys Gly
225                 230                 235                 240

Trp Lys Ile Ser Ser Asp Pro Arg Thr Tyr Asp Gly Tyr Pro Lys Asn
                245                 250                 255

Tyr Gly Tyr Arg Asn Tyr His Glu Asn Gly Ile Asn Tyr Asp Glu Phe
            260                 265                 270

Cys Gly Gly Tyr His Arg Ala Phe Asp Val Tyr Ser Asn Glu Thr Asn
        275                 280                 285

Asp Val Pro Ala Val Thr Ser Gly Thr Val Ile Glu Ala Asn Asp Tyr
    290                 295                 300

Gly Asn Phe Gly Gly Thr Phe Val Ile Arg Asp Ala Asn Asp Asn Asp
305                 310                 315                 320

Trp Ile Tyr Gly His Leu Gln Arg Gly Ser Met Arg Phe Val Val Gly
                325                 330                 335

Asp Lys Val Asn Gln Gly Asp Ile Ile Gly Leu Gln Gly Asn Ser Asn
            340                 345                 350

Tyr Tyr Asp Asn Pro Met Ser Val His Leu His Leu Gln Leu Arg Pro
        355                 360                 365

Lys Asp Ala Lys Lys Asp Glu Lys Ser Gln Val Cys Ser Gly Leu Ala
    370                 375                 380

Met Glu Lys Tyr Asp Ile Thr Asn Leu Asn Ala Lys Gln Asp Lys Ser
385                 390                 395                 400

Lys Asn Gly Ser Val Lys Glu Leu Lys His Ile Tyr Ser Asn His Ile
                405                 410                 415

Lys Gly Asn Lys Ile Thr Ala Pro Lys Pro Ser Ile Gln Gly Val Val
            420                 425                 430

Ile His Asn Asp Tyr Gly Ser Met Thr Pro Ser Gln Tyr Leu Pro Trp
        435                 440                 445

Leu Tyr Ala Arg Glu Asn Asn Gly Thr His Val Asn Gly Trp Ala Ser
    450                 455                 460

Val Tyr Ala Asn Arg Asn Glu Val Leu Trp Tyr His Pro Thr Asp Tyr
465                 470                 475                 480

Val Glu Trp His Cys Gly Asn Gln Trp Ala Asn Ala Asn Leu Ile Gly
                485                 490                 495

Phe Glu Val Cys Glu Ser Tyr Pro Gly Arg Ile Ser Asp Lys Leu Phe
            500                 505                 510

Leu Glu Asn Glu Glu Ala Thr Leu Lys Val Ala Ala Asp Val Met Lys
        515                 520                 525
```

```
Ser Tyr Gly Leu Pro Val Asn Arg Asn Thr Val Arg Leu His Asn Glu
    530                 535                 540

Phe Phe Gly Thr Ser Cys Pro His Arg Ser Trp Asp Leu His Val Gly
545                 550                 555                 560

Lys Gly Glu Pro Tyr Thr Thr Thr Asn Ile Asn Lys Met Lys Asp Tyr
                565                 570                 575

Phe Ile Lys Arg Ile Lys His Tyr Tyr Asp Gly Gly Lys Leu Glu Val
            580                 585                 590

Ser Lys Ala Ala Thr Ile Lys Gln Ser Asp Val Lys Gln Glu Val Lys
        595                 600                 605

Lys Gln Glu Ala Lys Gln Ile Val Lys Ala Thr Asp Trp Lys Gln Asn
    610                 615                 620

Lys Asp Gly Ile Trp Tyr Lys Ala Glu His Ala Ser Phe Thr Val Thr
625                 630                 635                 640

Ala Pro Glu Gly Ile Ile Thr Arg Tyr Lys Gly Pro Trp Thr Gly His
                645                 650                 655

Pro Gln Ala Gly Val Leu Gln Lys Gly Gln Thr Ile Lys Tyr Asp Glu
            660                 665                 670

Val Gln Lys Phe Asp Gly His Val Trp Val Ser Trp Glu Thr Phe Glu
        675                 680                 685

Gly Glu Thr Val Tyr Met Pro Val Arg Thr Trp Asp Ala Lys Thr Gly
    690                 695                 700

Lys Val Gly Lys Leu Trp Gly Glu Ile Lys
705                 710
```

<210> SEQ ID NO 81
<211> LENGTH: 1959
<212> TYPE: DNA
<213> ORGANISM: artificial
<220> FEATURE:
<223> OTHER INFORMATION: artificial construct

<400> SEQUENCE: 81

```
atgagaggat cgcatcacca tcaccatcac ggatccatga aaaccctgaa acaagcagag      60

tcctacatta agagtaaagt aaatacagga actgattttg atggtttata tgggtatcag     120

tgtatggact tagcagtaga ttatatttac catgtaacag atggtaaaat aagaatgtgg     180

ggtaatgcta aggatgcgat aaataactct tttggtggta ctgctacggt atataaaaac     240

taccctgctt ttagacctaa gtacggtgat gtagtcgtat ggactactgg taattttgca     300

acttatggtc atatcgcaat agttactaac cctgaccctt atggagacct tcaatatgtt     360

acagttcttg aacaaaactg gaacggtaac gggatttata aaaccgagtt agctacaatc     420

agaacacacg attacacagg aattacacat tttattaaag acgcaaagaa agatgaaaaa     480

tcacaagtat gtagtggttt ggctatggaa aaatatgaca ttacaaattt aaatgctaaa     540

caagataaat caaagaatgg gagcgtgaaa gagttgaaac atatctattc aaaccatatt     600

aaaggtaaca agattacagc accaaaacct agtattcaag gtgtggtcat ccacaatgat     660

tatggtagta tgacacctag tcaatactta ccatggttat atgcacgtga gaataacggt     720

acacacgtta acggttgggc tagtgtttat gcaaatagaa acgaagtgct ttggtatcat     780

ccgacagact acgtagagtg gcattgtggt aatcaatggg caaatgctaa cttaatcgga     840

tttgaagtgt gtgagtcgta tcctggtaga atctcggaca aattattctt agaaaatgaa     900

gaagcgacat tgaaagtagc tgcggatgtg atgaagtcgt acggattacc agttaatcgc     960

aacactgtac gtctgcataa cgaattcttc ggaacttctt gtccacatcg ttcgtgggac    1020
```

```
ttgcatgttg gcaaaggtga gccttacaca actactaata ttaataaaat gaaagactac   1080

ttcatcaaac gcatcaaaca ttattatgac ggtggaaagc tagaagtaag caaagcagca   1140

actatcaaac aatctgacgt taagcaagaa gttaaaaagc aagaagcaaa acaaattgtg   1200

aaagcaacag atgctgcaac acatgaacat tcagcacaat ggttgaataa ttacaaaaaa   1260

ggatatggtt acggtcctta tccattaggt ataaatggcg gtatgcacta cggagttgat   1320

tttttatga atattggaac accagtaaaa gctatttcaa gcggaaaaat agttgaagct   1380

ggttggagta attacggagg aggtaatcaa ataggtctta ttgaaaatga tggagtgcat   1440

agacaatggt atatgcatct aagtaaatat aatgttaaag taggagatta tgtcaaagct   1500

ggtcaaataa tcggttggtc tggaagcact ggttattcta cagcaccaca tttacacttc   1560

caaagaatgg ttaattcatt ttcaaattca actgcccaag atccaatgcc tttcttaaag   1620

agcgcaggat atggaaaagc aggtggtaca gtaactccaa cgccgaatac aggttggaaa   1680

cagaataaag atggcatttg gtataaagct gaacatgctt cgttcacagt gacagcacca   1740

gagggaatta tcacaagata caaaggtcct tggactggtc acccacaagc tggtgtatta   1800

caaaaaggtc aaacgattaa atatgatgag gttcaaaaat ttgacggtca tgtttgggta   1860

tcgtgggaaa cgtttgaggg cgaaactgta tacatgccgg tacgcacatg ggacgctaaa   1920

actggtaaag ttggtaagtt gtggggcgaa attaaataa                           1959
```

<210> SEQ ID NO 82
<211> LENGTH: 652
<212> TYPE: PRT
<213> ORGANISM: artificial
<220> FEATURE:
<223> OTHER INFORMATION: artificial construct

<400> SEQUENCE: 82

```
Met Arg Gly Ser His His His His His His Gly Ser Met Lys Thr Leu
1               5                   10                  15

Lys Gln Ala Glu Ser Tyr Ile Lys Ser Lys Val Asn Thr Gly Thr Asp
            20                  25                  30

Phe Asp Gly Leu Tyr Gly Tyr Gln Cys Met Asp Leu Ala Val Asp Tyr
        35                  40                  45

Ile Tyr His Val Thr Asp Gly Lys Ile Arg Met Trp Gly Asn Ala Lys
    50                  55                  60

Asp Ala Ile Asn Asn Ser Phe Gly Gly Thr Ala Thr Val Tyr Lys Asn
65                  70                  75                  80

Tyr Pro Ala Phe Arg Pro Lys Tyr Gly Asp Val Val Val Trp Thr Thr
                85                  90                  95

Gly Asn Phe Ala Thr Tyr Gly His Ile Ala Ile Val Thr Asn Pro Asp
            100                 105                 110

Pro Tyr Gly Asp Leu Gln Tyr Val Thr Val Leu Glu Gln Asn Trp Asn
        115                 120                 125

Gly Asn Gly Ile Tyr Lys Thr Glu Leu Ala Thr Ile Arg Thr His Asp
    130                 135                 140

Tyr Thr Gly Ile Thr His Phe Ile Lys Asp Ala Lys Lys Asp Glu Lys
145                 150                 155                 160

Ser Gln Val Cys Ser Gly Leu Ala Met Glu Lys Tyr Asp Ile Thr Asn
                165                 170                 175

Leu Asn Ala Lys Gln Asp Lys Ser Lys Asn Gly Ser Val Lys Glu Leu
            180                 185                 190
```

```
Lys His Ile Tyr Ser Asn His Ile Lys Gly Asn Lys Ile Thr Ala Pro
        195                 200                 205

Lys Pro Ser Ile Gln Gly Val Val Ile His Asn Asp Tyr Gly Ser Met
    210                 215                 220

Thr Pro Ser Gln Tyr Leu Pro Trp Leu Tyr Ala Arg Glu Asn Asn Gly
225                 230                 235                 240

Thr His Val Asn Gly Trp Ala Ser Val Tyr Ala Asn Arg Asn Glu Val
                245                 250                 255

Leu Trp Tyr His Pro Thr Asp Tyr Val Glu Trp His Cys Gly Asn Gln
            260                 265                 270

Trp Ala Asn Ala Asn Leu Ile Gly Phe Glu Val Cys Glu Ser Tyr Pro
        275                 280                 285

Gly Arg Ile Ser Asp Lys Leu Phe Leu Glu Asn Glu Glu Ala Thr Leu
    290                 295                 300

Lys Val Ala Ala Asp Val Met Lys Ser Tyr Gly Leu Pro Val Asn Arg
305                 310                 315                 320

Asn Thr Val Arg Leu His Asn Glu Phe Phe Gly Thr Ser Cys Pro His
                325                 330                 335

Arg Ser Trp Asp Leu His Val Gly Lys Gly Glu Pro Tyr Thr Thr Thr
            340                 345                 350

Asn Ile Asn Lys Met Lys Asp Tyr Phe Ile Lys Arg Ile Lys His Tyr
        355                 360                 365

Tyr Asp Gly Gly Lys Leu Glu Val Ser Lys Ala Ala Thr Ile Lys Gln
    370                 375                 380

Ser Asp Val Lys Gln Glu Val Lys Lys Gln Glu Ala Lys Gln Ile Val
385                 390                 395                 400

Lys Ala Thr Asp Ala Ala Thr His Glu His Ser Ala Gln Trp Leu Asn
                405                 410                 415

Asn Tyr Lys Lys Gly Tyr Gly Tyr Gly Pro Tyr Pro Leu Gly Ile Asn
            420                 425                 430

Gly Gly Met His Tyr Gly Val Asp Phe Phe Met Asn Ile Gly Thr Pro
        435                 440                 445

Val Lys Ala Ile Ser Ser Gly Lys Ile Val Glu Ala Gly Trp Ser Asn
    450                 455                 460

Tyr Gly Gly Gly Asn Gln Ile Gly Leu Ile Glu Asn Asp Gly Val His
465                 470                 475                 480

Arg Gln Trp Tyr Met His Leu Ser Lys Tyr Asn Val Lys Val Gly Asp
                485                 490                 495

Tyr Val Lys Ala Gly Gln Ile Ile Gly Trp Ser Gly Ser Thr Gly Tyr
            500                 505                 510

Ser Thr Ala Pro His Leu His Phe Gln Arg Met Val Asn Ser Phe Ser
        515                 520                 525

Asn Ser Thr Ala Gln Asp Pro Met Pro Phe Leu Lys Ser Ala Gly Tyr
    530                 535                 540

Gly Lys Ala Gly Gly Thr Val Thr Pro Thr Pro Asn Thr Gly Trp Lys
545                 550                 555                 560

Gln Asn Lys Asp Gly Ile Trp Tyr Lys Ala Glu His Ala Ser Phe Thr
                565                 570                 575

Val Thr Ala Pro Glu Gly Ile Ile Thr Arg Tyr Lys Gly Pro Trp Thr
            580                 585                 590

Gly His Pro Gln Ala Gly Val Leu Gln Lys Gly Gln Thr Ile Lys Tyr
        595                 600                 605

Asp Glu Val Gln Lys Phe Asp Gly His Val Trp Val Ser Trp Glu Thr
```

```
    610                 615                 620

Phe Glu Gly Glu Thr Val Tyr Met Pro Val Arg Thr Trp Asp Ala Lys
625                 630                 635                 640

Thr Gly Lys Val Gly Lys Leu Trp Gly Glu Ile Lys
                645                 650
```

<210> SEQ ID NO 83
<211> LENGTH: 1554
<212> TYPE: DNA
<213> ORGANISM: artificial
<220> FEATURE:
<223> OTHER INFORMATION: artificial construct

<400> SEQUENCE: 83

```
atgagaggat cgcatcacca tcaccatcac ggatccgctg caacacatga acattcagca     60
caatggttga ataattacaa aaaaggatat ggttacggtc cttatccatt aggtataaat    120
ggcggtatgc actacggagt tgattttttt atgaatattg gaacaccagt aaaagctatt    180
tcaagcggaa aaatagttga agctggttgg agtaattacg gaggaggtaa tcaaataggt    240
cttattgaaa atgatggagt gcatagacaa tggtatatgc atctaagtaa atataatgtt    300
aaagtaggag attatgtcaa agctggtcaa ataatcggtt ggtctggaag cactggttat    360
tctacagcac cacatttaca cttccaaaga atggttaatt cattttcaaa ttcaactgcc    420
caagatccaa tgcctttctt aaagagcgca ggatatggaa aagcaggtgg tacagtaact    480
ccaacgccga atacaggtga gctcttacgc cctaaagacg caaagaaaga tgaaaaatca    540
caagtatgta gtggtttggc tatggaaaaa tatgacatta caaatttaaa tgctaaacaa    600
gataaatcaa agaatgggag cgtgaaagag ttgaaacata tctattcaaa ccatattaaa    660
ggtaacaaga ttacagcacc aaaacctagt attcaaggtg tggtcatcca caatgattat    720
ggtagtatga cacctagtca atacttacca tggttatatg cacgtgagaa taacggtaca    780
cacgttaacg gttgggctag tgtttatgca aatagaaacg aagtgctttg gtatcatccg    840
acagactacg tagagtggca ttgtggtaat caatgggcaa atgctaactt aatcggattt    900
gaagtgtgtg agtcgtatcc tggtagaatc tcggacaaat tattcttaga aaatgaagaa    960
gcgacattga aagtagctgc ggatgtgatg aagtcgtacg gattaccagt taatcgcaac   1020
actgtacgtc tgcataacga attcttcgga acttcttgtc cacatcgttc gtgggacttg   1080
catgttggca aaggtgagcc ttacacaact actaatatta ataaaatgaa agactacttc   1140
atcaaacgca tcaaacatta ttatgacggt ggaaagctag aagtaagcaa agcagcaact   1200
atcaaacaat ctgacgttaa gcaagaagtt aaaaagcaag aagcaaaaca aattgtgaaa   1260
gcaacagatt ggaaacagaa taaagatggc atttggtata aagctgaaca tgcttcgttc   1320
acagtgacag caccagaggg aattatcaca agatacaaag gtccttggac tggtcaccca   1380
caagctggtg tattacaaaa aggtcaaacg attaaatatg atgaggttca aaaatttgac   1440
ggtcatgttt gggtatcgtg ggaaacgttt gagggcgaaa ctgtatacat gccggtacgc   1500
acatgggacg ctaaaactgg taaagttggt aagttgtggg gcgaaattaa ataa          1554
```

<210> SEQ ID NO 84
<211> LENGTH: 517
<212> TYPE: PRT
<213> ORGANISM: artificial
<220> FEATURE:
<223> OTHER INFORMATION: artificial construct

<400> SEQUENCE: 84

```
Met Arg Gly Ser His His His His His His Gly Ser Ala Ala Thr His
1               5                   10                  15

Glu His Ser Ala Gln Trp Leu Asn Asn Tyr Lys Lys Gly Tyr Gly Tyr
            20                  25                  30

Gly Pro Tyr Pro Leu Gly Ile Asn Gly Gly Met His Tyr Gly Val Asp
        35                  40                  45

Phe Phe Met Asn Ile Gly Thr Pro Val Lys Ala Ile Ser Ser Gly Lys
    50                  55                  60

Ile Val Glu Ala Gly Trp Ser Asn Tyr Gly Gly Gly Asn Gln Ile Gly
65                  70                  75                  80

Leu Ile Glu Asn Asp Gly Val His Arg Gln Trp Tyr Met His Leu Ser
                85                  90                  95

Lys Tyr Asn Val Lys Val Gly Asp Tyr Val Lys Ala Gly Gln Ile Ile
            100                 105                 110

Gly Trp Ser Gly Ser Thr Gly Tyr Ser Thr Ala Pro His Leu His Phe
        115                 120                 125

Gln Arg Met Val Asn Ser Phe Ser Asn Ser Thr Ala Gln Asp Pro Met
    130                 135                 140

Pro Phe Leu Lys Ser Ala Gly Tyr Gly Lys Ala Gly Gly Thr Val Thr
145                 150                 155                 160

Pro Thr Pro Asn Thr Gly Glu Leu Leu Arg Pro Lys Asp Ala Lys Lys
                165                 170                 175

Asp Glu Lys Ser Gln Val Cys Ser Gly Leu Ala Met Glu Lys Tyr Asp
            180                 185                 190

Ile Thr Asn Leu Asn Ala Lys Gln Asp Lys Ser Lys Asn Gly Ser Val
        195                 200                 205

Lys Glu Leu Lys His Ile Tyr Ser Asn His Ile Lys Gly Asn Lys Ile
    210                 215                 220

Thr Ala Pro Lys Pro Ser Ile Gln Gly Val Val Ile His Asn Asp Tyr
225                 230                 235                 240

Gly Ser Met Thr Pro Ser Gln Tyr Leu Pro Trp Leu Tyr Ala Arg Glu
                245                 250                 255

Asn Asn Gly Thr His Val Asn Gly Trp Ala Ser Val Tyr Ala Asn Arg
            260                 265                 270

Asn Glu Val Leu Trp Tyr His Pro Thr Asp Tyr Val Glu Trp His Cys
        275                 280                 285

Gly Asn Gln Trp Ala Asn Ala Asn Leu Ile Gly Phe Glu Val Cys Glu
    290                 295                 300

Ser Tyr Pro Gly Arg Ile Ser Asp Lys Leu Phe Leu Glu Asn Glu Glu
305                 310                 315                 320

Ala Thr Leu Lys Val Ala Ala Asp Val Met Lys Ser Tyr Gly Leu Pro
                325                 330                 335

Val Asn Arg Asn Thr Val Arg Leu His Asn Glu Phe Phe Gly Thr Ser
            340                 345                 350

Cys Pro His Arg Ser Trp Asp Leu His Val Gly Lys Gly Glu Pro Tyr
        355                 360                 365

Thr Thr Thr Asn Ile Asn Lys Met Lys Asp Tyr Phe Ile Lys Arg Ile
    370                 375                 380

Lys His Tyr Tyr Asp Gly Gly Lys Leu Glu Val Ser Lys Ala Ala Thr
385                 390                 395                 400

Ile Lys Gln Ser Asp Val Lys Gln Glu Val Lys Lys Gln Glu Ala Lys
                405                 410                 415
```

```
Gln Ile Val Lys Ala Thr Asp Trp Lys Gln Asn Lys Asp Gly Ile Trp
            420                 425                 430

Tyr Lys Ala Glu His Ala Ser Phe Thr Val Thr Ala Pro Glu Gly Ile
        435                 440                 445

Ile Thr Arg Tyr Lys Gly Pro Trp Thr Gly His Pro Gln Ala Gly Val
    450                 455                 460

Leu Gln Lys Gly Gln Thr Ile Lys Tyr Asp Glu Val Gln Lys Phe Asp
465                 470                 475                 480

Gly His Val Trp Val Ser Trp Glu Thr Phe Glu Gly Glu Thr Val Tyr
                485                 490                 495

Met Pro Val Arg Thr Trp Asp Ala Lys Thr Gly Lys Val Gly Lys Leu
            500                 505                 510

Trp Gly Glu Ile Lys
        515
```

<210> SEQ ID NO 85
<211> LENGTH: 1887
<212> TYPE: DNA
<213> ORGANISM: artificial
<220> FEATURE:
<223> OTHER INFORMATION: artificial construct

<400> SEQUENCE: 85

```
atgagaggat cgcatcacca tcaccatcac ggatccatgc taactgctat tgactatctt      60

acgaaaaaag gttggaaaat atcatctgac cctcgcactt acgatggtta ccctaaaaac     120

tacggctaca gaaattacca tgaaaacggc attaattatg atgagttttg tggtggttat     180

catagagctt ttgatgttta cagtaacgaa actaacgacg tgcctgctgt tactagcgga     240

acagttattg aagcaaacga ttacggtaat tttggtggta cattcgttat tagagacgct     300

aacgataacg attggatata tggcatctta caacgtggct caatgcgatt tgttgtaggc     360

gacaaagtca atcaaggtga cattattggt ttacaaggta atagcaacta ttacgacaat     420

cctatgagtg tacatttaca tttacaatta cgccctaaag acgcaaagaa agatgaaaaa     480

tcacaagtat gtagtggttt ggctatggaa aaatatgaca ttacaaattt aaatgctaaa     540

caagataaat caaagaatgg gagcgtgaaa gagttgaaac atatctattc aaaccatatt     600

aaaggtaaca agattacagc accaaaacct agtattcaag gtgtggtcat ccacaatgat     660

tatggtagta tgacacctag tcaatactta ccatggttat atgcacgtga gaataacggt     720

acacacgtta acggttgggc tagtgtttat gcaaatagaa acgaagtgct ttggtatcat     780

ccgacagact acgtagagtg gcattgtggt aatcaatggg caaatgctaa cttaatcgga     840

tttgaagtgt gtgagtcgta tcctggtaga atctcggaca aattattctt agaaaatgaa     900

gaagcgacat tgaaagtagc tgcggatgtg atgaagtcgt acggattacc agttaatcgc     960

aacactgtac gtctgcataa cgaattcttc ggaacttctt gtccacatcg ttcgtgggac    1020

ttgcatgttg gcaaaggtga gccttacaca actactaata ttaataaaat gaaagactac    1080

ttcatcaaac gcatcaaaca ttattatgac ggtggaaagc tagaagtaag caaagcagca    1140

actatcaaac aatctgacgt taagcaagaa gttaaaaagc aagaagcaaa acaaattgtg    1200

aaagcaacag attggaaaca gaataaagat ggcatttggt ataaagctga acatgcttcg    1260

ttcacagtga cagcaccaga gggaattatc acaagataca aaggtccttg gactggtcac    1320

ccacaagctg gtgtattaca aaaaggtcaa acgattaaat atgatgaggt tcaaaaattt    1380

gacggtcatg tttgggtatc gtgggaaacg tttgagggcg aaactgtata catgccggta    1440
```

```
cgcacatggg acgctaaaac tggtaaagtt ggtaagttgt ggggcgaaat taaagagctc   1500

ggtggaaagc tagaagtaag caaagcagca actatcaaac aatctgacgt taagcaagaa   1560

gttaaaaagc aagaagcaaa acaaattgtg aaagcaacag attggaaaca gaataaagat   1620

ggcatttggt ataaagctga acatgcttcg ttcacagtga cagcaccaga gggaattatc   1680

acaagataca aaggtccttg gactggtcac ccacaagctg gtgtattaca aaaaggtcaa   1740

acgattaaat atgatgaggt tcaaaaattt gacggtcatg tttgggtatc gtgggaaacg   1800

tttgagggcg aaactgtata catgccggta cgcacatggg acgctaaaac tggtaaagtt   1860

ggtaagttgt ggggcgaaat taaataa                                        1887
```

<210> SEQ ID NO 86
<211> LENGTH: 628
<212> TYPE: PRT
<213> ORGANISM: artificial
<220> FEATURE:
<223> OTHER INFORMATION: artificial construct

<400> SEQUENCE: 86

```
Met Arg Gly Ser His His His His His His Gly Ser Met Leu Thr Ala
1               5                   10                  15

Ile Asp Tyr Leu Thr Lys Lys Gly Trp Lys Ile Ser Ser Asp Pro Arg
            20                  25                  30

Thr Tyr Asp Gly Tyr Pro Lys Asn Tyr Gly Tyr Arg Asn Tyr His Glu
        35                  40                  45

Asn Gly Ile Asn Tyr Asp Glu Phe Cys Gly Gly Tyr His Arg Ala Phe
    50                  55                  60

Asp Val Tyr Ser Asn Glu Thr Asn Asp Val Pro Ala Val Thr Ser Gly
65                  70                  75                  80

Thr Val Ile Glu Ala Asn Asp Tyr Gly Asn Phe Gly Gly Thr Phe Val
                85                  90                  95

Ile Arg Asp Ala Asn Asp Asn Asp Trp Ile Tyr Gly His Leu Gln Arg
            100                 105                 110

Gly Ser Met Arg Phe Val Val Gly Asp Lys Val Asn Gln Gly Asp Ile
        115                 120                 125

Ile Gly Leu Gln Gly Asn Ser Asn Tyr Tyr Asp Asn Pro Met Ser Val
    130                 135                 140

His Leu His Leu Gln Leu Arg Pro Lys Asp Ala Lys Lys Asp Glu Lys
145                 150                 155                 160

Ser Gln Val Cys Ser Gly Leu Ala Met Glu Lys Tyr Asp Ile Thr Asn
                165                 170                 175

Leu Asn Ala Lys Gln Asp Lys Ser Lys Asn Gly Ser Val Lys Glu Leu
            180                 185                 190

Lys His Ile Tyr Ser Asn His Ile Lys Gly Asn Lys Ile Thr Ala Pro
        195                 200                 205

Lys Pro Ser Ile Gln Gly Val Val Ile His Asn Asp Tyr Gly Ser Met
    210                 215                 220

Thr Pro Ser Gln Tyr Leu Pro Trp Leu Tyr Ala Arg Glu Asn Asn Gly
225                 230                 235                 240

Thr His Val Asn Gly Trp Ala Ser Val Tyr Ala Asn Arg Asn Glu Val
                245                 250                 255

Leu Trp Tyr His Pro Thr Asp Tyr Val Glu Trp His Cys Gly Asn Gln
            260                 265                 270

Trp Ala Asn Ala Asn Leu Ile Gly Phe Glu Val Cys Glu Ser Tyr Pro
        275                 280                 285
```

```
Gly Arg Ile Ser Asp Lys Leu Phe Leu Glu Asn Glu Glu Ala Thr Leu
    290                 295                 300

Lys Val Ala Ala Asp Val Met Lys Ser Tyr Gly Leu Pro Val Asn Arg
305                 310                 315                 320

Asn Thr Val Arg Leu His Asn Glu Phe Phe Gly Thr Ser Cys Pro His
                325                 330                 335

Arg Ser Trp Asp Leu His Val Gly Lys Gly Glu Pro Tyr Thr Thr Thr
            340                 345                 350

Asn Ile Asn Lys Met Lys Asp Tyr Phe Ile Lys Arg Ile Lys His Tyr
        355                 360                 365

Tyr Asp Gly Gly Lys Leu Glu Val Ser Lys Ala Ala Thr Ile Lys Gln
    370                 375                 380

Ser Asp Val Lys Gln Glu Val Lys Lys Gln Glu Ala Lys Gln Ile Val
385                 390                 395                 400

Lys Ala Thr Asp Trp Lys Gln Asn Lys Asp Gly Ile Trp Tyr Lys Ala
                405                 410                 415

Glu His Ala Ser Phe Thr Val Thr Ala Pro Glu Gly Ile Ile Thr Arg
            420                 425                 430

Tyr Lys Gly Pro Trp Thr Gly His Pro Gln Ala Gly Val Leu Gln Lys
        435                 440                 445

Gly Gln Thr Ile Lys Tyr Asp Glu Val Gln Lys Phe Asp Gly His Val
    450                 455                 460

Trp Val Ser Trp Glu Thr Phe Glu Gly Glu Thr Val Tyr Met Pro Val
465                 470                 475                 480

Arg Thr Trp Asp Ala Lys Thr Gly Lys Val Gly Lys Leu Trp Gly Glu
                485                 490                 495

Ile Lys Glu Leu Gly Gly Lys Leu Glu Val Ser Lys Ala Ala Thr Ile
            500                 505                 510

Lys Gln Ser Asp Val Lys Gln Glu Val Lys Lys Gln Glu Ala Lys Gln
        515                 520                 525

Ile Val Lys Ala Thr Asp Trp Lys Gln Asn Lys Asp Gly Ile Trp Tyr
    530                 535                 540

Lys Ala Glu His Ala Ser Phe Thr Val Thr Ala Pro Glu Gly Ile Ile
545                 550                 555                 560

Thr Arg Tyr Lys Gly Pro Trp Thr Gly His Pro Gln Ala Gly Val Leu
                565                 570                 575

Gln Lys Gly Gln Thr Ile Lys Tyr Asp Glu Val Gln Lys Phe Asp Gly
            580                 585                 590

His Val Trp Val Ser Trp Glu Thr Phe Glu Gly Glu Thr Val Tyr Met
        595                 600                 605

Pro Val Arg Thr Trp Asp Ala Lys Thr Gly Lys Val Gly Lys Leu Trp
    610                 615                 620

Gly Glu Ile Lys
625
```

<210> SEQ ID NO 87
<211> LENGTH: 1035
<212> TYPE: DNA
<213> ORGANISM: artificial
<220> FEATURE:
<223> OTHER INFORMATION: artificial construct

<400> SEQUENCE: 87

```
atgagaggat cgcatcacca tcaccatcac ggatccatgc taactgctat tgactatctt      60
```

```
acgaaaaaag gttggaaaat atcatctgac cctcgcactt acgatggtta ccctaaaaac    120

tacggctaca gaaattacca tgaaaacggc attaattatg atgagttttg tggtggttat    180

catagagctt ttgatgttta cagtaacgaa actaacgacg tgcctgctgt tactagcgga    240

acagttattg aagcaaacga ttacggtaat tttggtggta cattcgttat tagagacgct    300

aacgataacg attggatata tgggcatcta caacgtggct caatgcgatt tgttgtaggc    360

gacaaagtca atcaaggtga cattattggt ttacaaggta atagcaacta ttacgacaat    420

cctatgagtg tacatttaca tttacaatta cgccctaaag acgcaaagaa agatgaaaaa    480

tcacaagtat gtagtggttt ggctatggaa aaatatgaca ttacaaattt aaatgctaaa    540

caagataaat caaagaatgg gagcgtgaaa gagttgaaac atatctattc aaaccatatt    600

aaaggtaaca agattacagc accaaaacct agtattcaag gtgagctcgg tggaaagcta    660

gaagtaagca aagcagcaac tatcaaacaa tctgacgtta agcaagaagt taaaaagcaa    720

gaagcaaaac aaattgtgaa agcaacagat tggaaacaga ataaagatgg catttggtat    780

aaagctgaac atgcttcgtt cacagtgaca gcaccagagg gaattatcac aagatacaaa    840

ggtccttgga ctggtcaccc acaagctggt gtattacaaa aaggtcaaac gattaaatat    900

gatgaggttc aaaaatttga cggtcatgtt tgggtatcgt gggaaacgtt tgagggcgaa    960

actgtataca tgccggtacg cacatgggac gctaaaactg gtaaagttgg taagttgtgg   1020

ggcgaaatta aataa                                                    1035


<210> SEQ ID NO 88
<211> LENGTH: 344
<212> TYPE: PRT
<213> ORGANISM: artificial
<220> FEATURE:
<223> OTHER INFORMATION: artificial construct

<400> SEQUENCE: 88

Met Arg Gly Ser His His His His His His Gly Ser Met Leu Thr Ala
1               5                   10                  15

Ile Asp Tyr Leu Thr Lys Lys Gly Trp Lys Ile Ser Ser Asp Pro Arg
            20                  25                  30

Thr Tyr Asp Gly Tyr Pro Lys Asn Tyr Gly Tyr Arg Asn Tyr His Glu
        35                  40                  45

Asn Gly Ile Asn Tyr Asp Glu Phe Cys Gly Gly Tyr His Arg Ala Phe
    50                  55                  60

Asp Val Tyr Ser Asn Glu Thr Asn Asp Val Pro Ala Val Thr Ser Gly
65                  70                  75                  80

Thr Val Ile Glu Ala Asn Asp Tyr Gly Asn Phe Gly Gly Thr Phe Val
                85                  90                  95

Ile Arg Asp Ala Asn Asp Asn Asp Trp Ile Tyr Gly His Leu Gln Arg
            100                 105                 110

Gly Ser Met Arg Phe Val Val Gly Asp Lys Val Asn Gln Gly Asp Ile
        115                 120                 125

Ile Gly Leu Gln Gly Asn Ser Asn Tyr Tyr Asp Asn Pro Met Ser Val
    130                 135                 140

His Leu His Leu Gln Leu Arg Pro Lys Asp Ala Lys Lys Asp Glu Lys
145                 150                 155                 160

Ser Gln Val Cys Ser Gly Leu Ala Met Glu Lys Tyr Asp Ile Thr Asn
                165                 170                 175

Leu Asn Ala Lys Gln Asp Lys Ser Lys Asn Gly Ser Val Lys Glu Leu
            180                 185                 190
```

```
Lys His Ile Tyr Ser Asn His Ile Lys Gly Asn Lys Ile Thr Ala Pro
        195                 200                 205

Lys Pro Ser Ile Gln Gly Glu Leu Gly Gly Lys Leu Glu Val Ser Lys
    210                 215                 220

Ala Ala Thr Ile Lys Gln Ser Asp Val Lys Gln Glu Val Lys Lys Gln
225                 230                 235                 240

Glu Ala Lys Gln Ile Val Lys Ala Thr Asp Trp Lys Gln Asn Lys Asp
                245                 250                 255

Gly Ile Trp Tyr Lys Ala Glu His Ala Ser Phe Thr Val Thr Ala Pro
            260                 265                 270

Glu Gly Ile Ile Thr Arg Tyr Lys Gly Pro Trp Thr Gly His Pro Gln
        275                 280                 285

Ala Gly Val Leu Gln Lys Gly Gln Thr Ile Lys Tyr Asp Glu Val Gln
    290                 295                 300

Lys Phe Asp Gly His Val Trp Val Ser Trp Glu Thr Phe Glu Gly Glu
305                 310                 315                 320

Thr Val Tyr Met Pro Val Arg Thr Trp Asp Ala Lys Thr Gly Lys Val
                325                 330                 335

Gly Lys Leu Trp Gly Glu Ile Lys
            340
```

<210> SEQ ID NO 89
<211> LENGTH: 2961
<212> TYPE: DNA
<213> ORGANISM: artificial
<220> FEATURE:
<223> OTHER INFORMATION: artificial construct

<400> SEQUENCE: 89

```
atgagaggat cgcatcacca tcaccatcac ggatccatgc taactgctat tgactatctt      60

acgaaaaaag gttggaaaat atcatctgac cctcgcactt acgatggtta ccctaaaaac     120

tacggctaca gaaattacca tgaaaacggc attaattatg atgagttttg tggtggttat     180

catagagctt ttgatgttta cagtaacgaa actaacgacg tgcctgctgt tactagcgga     240

acagttattg aagcaaacga ttacggtaat tttggtggta cattcgttat tagagacgct     300

aacgataacg attggatata tggcatcta caacgtggct caatgcgatt tgttgtaggc     360

gacaaagtca atcaaggtga cattattggt ttacaaggta atagcaacta ttacgacaat     420

cctatgagtg tacatttaca tttacaatta cgccctaaag acgcaaagaa agatgaaaaa     480

tcacaagtat gtagtggttt ggctatggaa aaatatgaca ttacaaattt aaatgctaaa     540

caagataaat caaagaatgg gagcgtgaaa gagttgaaac atatctattc aaaccatatt     600

aaaggtaaca agattacagc accaaaacct agtattcaag gtgtggtcat ccacaatgat     660

tatggtagta tgacacctag tcaatactta ccatggttat atgcacgtga gaataacggt     720

acacacgtta acggttgggc tagtgtttat gcaaatagaa acgaagtgct ttggtatcat     780

ccgacagact acgtagagtg gcattgtggt aatcaatggg caaatgctaa cttaatcgga     840

tttgaagtgt gtgagtcgta tcctggtaga atctcggaca aattattctt agaaaatgaa     900

gaagcgacat tgaaagtagc tgcggatgtg atgaagtcgt acggattacc agttaatcgc     960

aacactgtac gtctgcataa cgaattcttc ggaacttctt gtccacatcg ttcgtgggac    1020

ttgcatgttg gcaaaggtga gccttacaca actactaata ttaataaaat gaaagactac    1080

ttcatcaaac gcatcaaaca ttattatgac ggtggaaagc tagaagtaag caaagcagca    1140
```

```
actatcaaac aatctgacgt taagcaagaa gttaaaaagc aagaagcaaa acaaattgtg   1200
aaagcaacag attggaaaca gaataaagat ggcatttggt ataaagctga acatgcttcg   1260
ttcacagtga cagcaccaga gggaattatc acaagataca aaggtccttg gactggtcac   1320
ccacaagctg gtgtattaca aaaaggtcaa acgattaaat atgatgaggt tcaaaaattt   1380
gacggtcatg tttgggtatc gtgggaaacg tttgagggcg aaactgtata catgccggta   1440
cgcacatggg acgctaaaac tggtaaagtt ggtaagttgt ggggcgaaat taaagagctc   1500
atgctaactg ctattgacta tcttacgaaa aaaggttgga aaatatcatc tgaccctcgc   1560
acttacgatg gttaccctaa aaactacggc tacagaaatt accatgaaaa cggcattaat   1620
tatgatgagt tttgtggtgg ttatcataga gcttttgatg tttacagtaa cgaaactaac   1680
gacgtgcctg ctgttactag cggaacagtt attgaagcaa acgattacgg taattttggt   1740
ggtacattcg ttattagaga cgctaacgat aacgattgga tatatgggca tctacaacgt   1800
ggctcaatgc gatttgttgt aggcgacaaa gtcaatcaag gtgacattat tggtttacaa   1860
ggtaatagca actattacga caatcctatg agtgtacatt tacatttaca attacgccct   1920
aaagacgcaa agaaagatga aaaatcacaa gtatgtagtg gtttggctat ggaaaaatat   1980
gacattacaa atttaaatgc taaacaagat aaatcaaaga atgggagcgt gaaagagttg   2040
aaacatatct attcaaacca tattaaaggt aacaagatta cagcaccaaa acctagtatt   2100
caaggtgtgg tcatccacaa tgattatggt agtatgacac ctagtcaata cttaccatgg   2160
ttatatgcac gtgagaataa cggtacacac gttaacggtt gggctagtgt tttatgcaaat  2220
agaaacgaag tgctttggta tcatccgaca gactacgtag agtggcattg tggtaatcaa   2280
tgggcaaatg ctaacttaat cggatttgaa gtgtgtgagt cgtatcctgg tagaatctcg   2340
gacaaattat tcttagaaaa tgaagaagcg acattgaaag tagctgcgga tgtgatgaag   2400
tcgtacggat taccagttaa tcgcaacact gtacgtctgc ataacgaatt cttcggaact   2460
tcttgtccac atcgttcgtg ggacttgcat gttggcaaag gtgagcctta cacaactact   2520
aatattaata aaatgaaaga ctacttcatc aaacgcatca aacattatta tgacggtgga   2580
aagctagaag taagcaaagc agcaactatc aaacaatctg acgttaagca agaagttaaa   2640
aagcaagaag caaaacaaat tgtgaaagca acagattgga aacagaataa agatggcatt   2700
tggtataaag ctgaacatgc ttcgttcaca gtgacagcac cagagggaat tatcacaaga   2760
tacaaaggtc cttggactgg tcacccacaa gctggtgtat tacaaaaagg tcaaacgatt   2820
aaatatgatg aggttcaaaa atttgacggt catgtttggg tatcgtggga aacgtttgag   2880
ggcgaaactg tatacatgcc ggtacgcaca tgggacgcta aaactggtaa agttggtaag   2940
ttgtggggcg aaattaaata a                                             2961
```

<210> SEQ ID NO 90
<211> LENGTH: 986
<212> TYPE: PRT
<213> ORGANISM: artificial
<220> FEATURE:
<223> OTHER INFORMATION: artificial construct

<400> SEQUENCE: 90

```
Met Arg Gly Ser His His His His His His Gly Ser Met Leu Thr Ala
1               5                   10                  15

Ile Asp Tyr Leu Thr Lys Lys Gly Trp Lys Ile Ser Ser Asp Pro Arg
            20                  25                  30

Thr Tyr Asp Gly Tyr Pro Lys Asn Tyr Gly Tyr Arg Asn Tyr His Glu
```

```
        35                  40                  45

Asn Gly Ile Asn Tyr Asp Glu Phe Cys Gly Gly Tyr His Arg Ala Phe
    50                  55                  60

Asp Val Tyr Ser Asn Glu Thr Asn Asp Val Pro Ala Val Thr Ser Gly
65                  70                  75                  80

Thr Val Ile Glu Ala Asn Asp Tyr Gly Asn Phe Gly Gly Thr Phe Val
                85                  90                  95

Ile Arg Asp Ala Asn Asp Asn Asp Trp Ile Tyr Gly His Leu Gln Arg
            100                 105                 110

Gly Ser Met Arg Phe Val Val Gly Asp Lys Val Asn Gln Gly Asp Ile
        115                 120                 125

Ile Gly Leu Gln Gly Asn Ser Asn Tyr Tyr Asp Asn Pro Met Ser Val
    130                 135                 140

His Leu His Leu Gln Leu Arg Pro Lys Asp Ala Lys Lys Asp Glu Lys
145                 150                 155                 160

Ser Gln Val Cys Ser Gly Leu Ala Met Glu Lys Tyr Asp Ile Thr Asn
                165                 170                 175

Leu Asn Ala Lys Gln Asp Lys Ser Lys Asn Gly Ser Val Lys Glu Leu
            180                 185                 190

Lys His Ile Tyr Ser Asn His Ile Lys Gly Asn Lys Ile Thr Ala Pro
        195                 200                 205

Lys Pro Ser Ile Gln Gly Val Val Ile His Asn Asp Tyr Gly Ser Met
    210                 215                 220

Thr Pro Ser Gln Tyr Leu Pro Trp Leu Tyr Ala Arg Glu Asn Asn Gly
225                 230                 235                 240

Thr His Val Asn Gly Trp Ala Ser Val Tyr Ala Asn Arg Asn Glu Val
                245                 250                 255

Leu Trp Tyr His Pro Thr Asp Tyr Val Glu Trp His Cys Gly Asn Gln
            260                 265                 270

Trp Ala Asn Ala Asn Leu Ile Gly Phe Glu Val Cys Glu Ser Tyr Pro
        275                 280                 285

Gly Arg Ile Ser Asp Lys Leu Phe Leu Glu Asn Glu Glu Ala Thr Leu
    290                 295                 300

Lys Val Ala Ala Asp Val Met Lys Ser Tyr Gly Leu Pro Val Asn Arg
305                 310                 315                 320

Asn Thr Val Arg Leu His Asn Glu Phe Phe Gly Thr Ser Cys Pro His
                325                 330                 335

Arg Ser Trp Asp Leu His Val Gly Lys Gly Glu Pro Tyr Thr Thr Thr
            340                 345                 350

Asn Ile Asn Lys Met Lys Asp Tyr Phe Ile Lys Arg Ile Lys His Tyr
        355                 360                 365

Tyr Asp Gly Gly Lys Leu Glu Val Ser Lys Ala Ala Thr Ile Lys Gln
    370                 375                 380

Ser Asp Val Lys Gln Glu Val Lys Lys Gln Glu Ala Lys Gln Ile Val
385                 390                 395                 400

Lys Ala Thr Asp Trp Lys Gln Asn Lys Asp Gly Ile Trp Tyr Lys Ala
                405                 410                 415

Glu His Ala Ser Phe Thr Val Thr Ala Pro Glu Gly Ile Ile Thr Arg
            420                 425                 430

Tyr Lys Gly Pro Trp Thr Gly His Pro Gln Ala Gly Val Leu Gln Lys
        435                 440                 445

Gly Gln Thr Ile Lys Tyr Asp Glu Val Gln Lys Phe Asp Gly His Val
    450                 455                 460
```

Trp Val Ser Trp Glu Thr Phe Glu Gly Glu Thr Val Tyr Met Pro Val
465 470 475 480

Arg Thr Trp Asp Ala Lys Thr Gly Lys Val Gly Lys Leu Trp Gly Glu
485 490 495

Ile Lys Glu Leu Met Leu Thr Ala Ile Asp Tyr Leu Thr Lys Lys Gly
500 505 510

Trp Lys Ile Ser Ser Asp Pro Arg Thr Tyr Asp Gly Tyr Pro Lys Asn
515 520 525

Tyr Gly Tyr Arg Asn Tyr His Glu Asn Gly Ile Asn Tyr Asp Glu Phe
530 535 540

Cys Gly Gly Tyr His Arg Ala Phe Asp Val Tyr Ser Asn Glu Thr Asn
545 550 555 560

Asp Val Pro Ala Val Thr Ser Gly Thr Val Ile Glu Ala Asn Asp Tyr
565 570 575

Gly Asn Phe Gly Gly Thr Phe Val Ile Arg Asp Ala Asn Asp Asn Asp
580 585 590

Trp Ile Tyr Gly His Leu Gln Arg Gly Ser Met Arg Phe Val Val Gly
595 600 605

Asp Lys Val Asn Gln Gly Asp Ile Ile Gly Leu Gln Gly Asn Ser Asn
610 615 620

Tyr Tyr Asp Asn Pro Met Ser Val His Leu His Leu Gln Leu Arg Pro
625 630 635 640

Lys Asp Ala Lys Lys Asp Glu Lys Ser Gln Val Cys Ser Gly Leu Ala
645 650 655

Met Glu Lys Tyr Asp Ile Thr Asn Leu Asn Ala Lys Gln Asp Lys Ser
660 665 670

Lys Asn Gly Ser Val Lys Glu Leu Lys His Ile Tyr Ser Asn His Ile
675 680 685

Lys Gly Asn Lys Ile Thr Ala Pro Lys Pro Ser Ile Gln Gly Val Val
690 695 700

Ile His Asn Asp Tyr Gly Ser Met Thr Pro Ser Gln Tyr Leu Pro Trp
705 710 715 720

Leu Tyr Ala Arg Glu Asn Asn Gly Thr His Val Asn Gly Trp Ala Ser
725 730 735

Val Tyr Ala Asn Arg Asn Glu Val Leu Trp Tyr His Pro Thr Asp Tyr
740 745 750

Val Glu Trp His Cys Gly Asn Gln Trp Ala Asn Ala Asn Leu Ile Gly
755 760 765

Phe Glu Val Cys Glu Ser Tyr Pro Gly Arg Ile Ser Asp Lys Leu Phe
770 775 780

Leu Glu Asn Glu Glu Ala Thr Leu Lys Val Ala Ala Asp Val Met Lys
785 790 795 800

Ser Tyr Gly Leu Pro Val Asn Arg Asn Thr Val Arg Leu His Asn Glu
805 810 815

Phe Phe Gly Thr Ser Cys Pro His Arg Ser Trp Asp Leu His Val Gly
820 825 830

Lys Gly Glu Pro Tyr Thr Thr Thr Asn Ile Asn Lys Met Lys Asp Tyr
835 840 845

Phe Ile Lys Arg Ile Lys His Tyr Tyr Asp Gly Gly Lys Leu Glu Val
850 855 860

Ser Lys Ala Ala Thr Ile Lys Gln Ser Asp Val Lys Gln Glu Val Lys
865 870 875 880

```
Lys Gln Glu Ala Lys Gln Ile Val Lys Ala Thr Asp Trp Lys Gln Asn
                885                 890                 895

Lys Asp Gly Ile Trp Tyr Lys Ala Glu His Ala Ser Phe Thr Val Thr
            900                 905                 910

Ala Pro Glu Gly Ile Ile Thr Arg Tyr Lys Gly Pro Trp Thr Gly His
        915                 920                 925

Pro Gln Ala Gly Val Leu Gln Lys Gly Gln Thr Ile Lys Tyr Asp Glu
    930                 935                 940

Val Gln Lys Phe Asp Gly His Val Trp Val Ser Trp Glu Thr Phe Glu
945                 950                 955                 960

Gly Glu Thr Val Tyr Met Pro Val Arg Thr Trp Asp Ala Lys Thr Gly
                965                 970                 975

Lys Val Gly Lys Leu Trp Gly Glu Ile Lys
            980                 985
```

```
<210> SEQ ID NO 91
<211> LENGTH: 1953
<212> TYPE: DNA
<213> ORGANISM: artificial
<220> FEATURE:
<223> OTHER INFORMATION: artificial construct

<400> SEQUENCE: 91

atgagaggat cgcatcacca tcaccatcac ggatccatga aaccctgaa acaagcagag     60

tcctacatta agagtaaagt aaatacagga actgattttg atggtttata tgggtatcag    120

tgtatggact tagcagtaga ttatatttac catgtaacag atggtaaaat aagaatgtgg    180

ggtaatgcta aggatgcgat aaataactct tttggtggta ctgctacggt atataaaaac    240

taccctgctt ttagacctaa gtacggtgat gtagtcgtat ggactactgg taattttgca    300

acttatggtc atatcgcaat agttactaac cctgaccctt atggagacct tcaatatgtt    360

acagttcttg aacaaaactg gaacggtaac gggatttata aaccgagtt agctacaatc    420

agaacacacg attacacagg aattacacat tttattaaag acgcaaagaa agatgaaaaa    480

tcacaagtat gtagtggttt ggctatggaa aaatatgaca ttacaaattt aaatgctaaa    540

caagataaat caaagaatgg gagcgtgaaa gagttgaaac atatctattc aaaccatatt    600

aaaggtaaca agattacagc accaaaacct agtattcaag gtgtggtcat ccacaatgat    660

tatggtagta tgacacctag tcaatactta ccatggttat atgcacgtga gaataacggt    720

acacacgtta acggttgggc tagtgtttat gcaaatagaa acgaagtgct ttggtatcat    780

ccgacagact acgtagagtg gcattgtggt aatcaatggg caaatgctaa cttaatcgga    840

tttgaagtgt gtgagtcgta tcctggtaga atctcggaca aattattctt agaaaatgaa    900

gaagcgacat tgaaagtagc tgcggatgtg atgaagtcgt acggattacc agttaatcgc    960

aacactgtac gtctgcataa cgaattcttc ggaacttctt gtccacatcg ttcgtgggac   1020

ttgcatgttg gcaaaggtga gccttacaca actactaata ttaataaaat gaaagactac   1080

ttcatcaaac gcatcaaaca ttattatgac ggtggaaagc tagaagtaag caaagcagca   1140

actatcaaac aatctgacgt taagcaagaa gttaaaaagc aagaagcaaa acaaattgtg   1200

aaagcaacag atgctgcaac acatgaacat tcagcacaat ggttgaataa ttacaaaaaa   1260

ggatatggtt acggtcctta tccattaggt ataaatggcg gtatgcacta cggagttgat   1320

ttttttatga atattggaac accagtaaaa gctatttcaa gcggaaaaat agttgaagct   1380

ggttggagta attacggagg aggtaatcaa ataggtctta ttgaaaatga tggagtgcat   1440
```

```
agacaatggt atatgcatct aagtaaatat aatgttaaag taggagatta tgtcaaagct   1500

ggtcaaataa tcggttggtc tggaagcact ggttattcta cagcaccaca tttacacttc   1560

caaagaatgg ttaattcatt ttcaaattca actgcccaag atccaatgcc tttcttaaag   1620

agcgcaggat atggaaaagc aggtggtaca gtaactccaa cgccgaatac aggttggaaa   1680

acaaacaaat atggcacact atataaatca gagtcagcta gcttcacacc taatacagat   1740

ataataacaa gaacgactgg tccatttaga agcatgccgc agtcaggagt cttaaaagca   1800

ggtcaaacaa ttcattatga tgaagtgatg aaacaagacg gtcatgtttg ggtaggttat   1860

acaggtaaca gtggccaacg tatttacttg cctgtaagaa catggaataa atctactaat   1920

actttaggtg ttctttgggg aactataaag taa                                1953
```

```
<210> SEQ ID NO 92
<211> LENGTH: 650
<212> TYPE: PRT
<213> ORGANISM: artificial
<220> FEATURE:
<223> OTHER INFORMATION: artificial construct

<400> SEQUENCE: 92

Met Arg Gly Ser His His His His His His Gly Ser Met Lys Thr Leu
1               5                   10                  15

Lys Gln Ala Glu Ser Tyr Ile Lys Ser Lys Val Asn Thr Gly Thr Asp
            20                  25                  30

Phe Asp Gly Leu Tyr Gly Tyr Gln Cys Met Asp Leu Ala Val Asp Tyr
        35                  40                  45

Ile Tyr His Val Thr Asp Gly Lys Ile Arg Met Trp Gly Asn Ala Lys
    50                  55                  60

Asp Ala Ile Asn Asn Ser Phe Gly Gly Thr Ala Thr Val Tyr Lys Asn
65                  70                  75                  80

Tyr Pro Ala Phe Arg Pro Lys Tyr Gly Asp Val Val Val Trp Thr Thr
                85                  90                  95

Gly Asn Phe Ala Thr Tyr Gly His Ile Ala Ile Val Thr Asn Pro Asp
            100                 105                 110

Pro Tyr Gly Asp Leu Gln Tyr Val Thr Val Leu Glu Gln Asn Trp Asn
        115                 120                 125

Gly Asn Gly Ile Tyr Lys Thr Glu Leu Ala Thr Ile Arg Thr His Asp
    130                 135                 140

Tyr Thr Gly Ile Thr His Phe Ile Lys Asp Ala Lys Lys Asp Glu Lys
145                 150                 155                 160

Ser Gln Val Cys Ser Gly Leu Ala Met Glu Lys Tyr Asp Ile Thr Asn
                165                 170                 175

Leu Asn Ala Lys Gln Asp Lys Ser Lys Asn Gly Ser Val Lys Glu Leu
            180                 185                 190

Lys His Ile Tyr Ser Asn His Ile Lys Gly Asn Lys Ile Thr Ala Pro
        195                 200                 205

Lys Pro Ser Ile Gln Gly Val Val Ile His Asn Asp Tyr Gly Ser Met
    210                 215                 220

Thr Pro Ser Gln Tyr Leu Pro Trp Leu Tyr Ala Arg Glu Asn Asn Gly
225                 230                 235                 240

Thr His Val Asn Gly Trp Ala Ser Val Tyr Ala Asn Arg Asn Glu Val
                245                 250                 255

Leu Trp Tyr His Pro Thr Asp Tyr Val Glu Trp His Cys Gly Asn Gln
            260                 265                 270
```

```
Trp Ala Asn Ala Asn Leu Ile Gly Phe Glu Val Cys Glu Ser Tyr Pro
        275                 280                 285

Gly Arg Ile Ser Asp Lys Leu Phe Leu Glu Asn Glu Glu Ala Thr Leu
    290                 295                 300

Lys Val Ala Ala Asp Val Met Lys Ser Tyr Gly Leu Pro Val Asn Arg
305                 310                 315                 320

Asn Thr Val Arg Leu His Asn Glu Phe Phe Gly Thr Ser Cys Pro His
                325                 330                 335

Arg Ser Trp Asp Leu His Val Gly Lys Gly Glu Pro Tyr Thr Thr Thr
            340                 345                 350

Asn Ile Asn Lys Met Lys Asp Tyr Phe Ile Lys Arg Ile Lys His Tyr
        355                 360                 365

Tyr Asp Gly Gly Lys Leu Glu Val Ser Lys Ala Ala Thr Ile Lys Gln
    370                 375                 380

Ser Asp Val Lys Gln Glu Val Lys Lys Gln Glu Ala Lys Gln Ile Val
385                 390                 395                 400

Lys Ala Thr Asp Ala Ala Thr His Glu His Ser Ala Gln Trp Leu Asn
                405                 410                 415

Asn Tyr Lys Lys Gly Tyr Gly Tyr Gly Pro Tyr Pro Leu Gly Ile Asn
            420                 425                 430

Gly Gly Met His Tyr Gly Val Asp Phe Phe Met Asn Ile Gly Thr Pro
        435                 440                 445

Val Lys Ala Ile Ser Ser Gly Lys Ile Val Glu Ala Gly Trp Ser Asn
    450                 455                 460

Tyr Gly Gly Gly Asn Gln Ile Gly Leu Ile Glu Asn Asp Gly Val His
465                 470                 475                 480

Arg Gln Trp Tyr Met His Leu Ser Lys Tyr Asn Val Lys Val Gly Asp
                485                 490                 495

Tyr Val Lys Ala Gly Gln Ile Ile Gly Trp Ser Gly Ser Thr Gly Tyr
            500                 505                 510

Ser Thr Ala Pro His Leu His Phe Gln Arg Met Val Asn Ser Phe Ser
        515                 520                 525

Asn Ser Thr Ala Gln Asp Pro Met Pro Phe Leu Lys Ser Ala Gly Tyr
    530                 535                 540

Gly Lys Ala Gly Gly Thr Val Thr Pro Thr Pro Asn Thr Gly Trp Lys
545                 550                 555                 560

Thr Asn Lys Tyr Gly Thr Leu Tyr Lys Ser Glu Ser Ala Ser Phe Thr
                565                 570                 575

Pro Asn Thr Asp Ile Ile Thr Arg Thr Thr Gly Pro Phe Arg Ser Met
            580                 585                 590

Pro Gln Ser Gly Val Leu Lys Ala Gly Gln Thr Ile His Tyr Asp Glu
        595                 600                 605

Val Met Lys Gln Asp Gly His Val Trp Val Gly Tyr Thr Gly Asn Ser
    610                 615                 620

Gly Gln Arg Ile Tyr Leu Pro Val Arg Thr Trp Asn Lys Ser Thr Asn
625                 630                 635                 640

Thr Leu Gly Val Leu Trp Gly Thr Ile Lys
                645                 650
```

<210> SEQ ID NO 93
<211> LENGTH: 1521
<212> TYPE: DNA
<213> ORGANISM: artificial
<220> FEATURE:
<223> OTHER INFORMATION: artificial construct

<400> SEQUENCE: 93

```
atgagaggat cgcatcacca tcaccatcac ggatccgctg caacacatga acattcagca      60
caatggttga ataattacaa aaaaggatat ggttacggtc cttatccatt aggtataaat     120
ggcggtatgc actacggagt tgattttttt atgaatattg gaacaccagt aaaagctatt     180
tcaagcggaa aaatagttga agctggttgg agtaattacg gaggaggtaa tcaaataggt     240
cttattgaaa atgatggagt gcatagacaa tggtatatgc atctaagtaa atataatgtt     300
aaagtaggag attatgtcaa agctggtcaa ataatcggtt ggtctggaag cactggttat     360
tctacagcac cacatttaca cttccaaaga atggttaatt cattttcaaa ttcaactgcc     420
caagatccaa tgcctttctt aaagagcgca ggatatggaa aagcaggtgg tacagtaact     480
ccaacgccga atacaggttg gaaaacaaac aaatatggca cactatataa atcagagtca     540
gctagcttca cacctaatac agatataata acaagaacga ctggtccatt tagaagcatg     600
ccgcagtcag gagtcttaaa agcaggtcaa acaattcatt atgatgaagt gatgaaacaa     660
gacggtcatg tttgggtagg ttatacaggt aacagtggcc aacgtattta cttgcctgta     720
agaacatgga ataaatctac taatacttta ggtgttcttt ggggaactat aaaggagctc     780
gctgcaacac atgaacattc agcacaatgg ttgaataatt acaaaaaagg atatggttac     840
ggtccttatc cattaggtat aaatggcggt atgcactacg gagttgattt ttttatgaat     900
attggaacac cagtaaaagc tatttcaagc ggaaaaatag ttgaagctgg ttggagtaat     960
tacggaggag gtaatcaaat aggtcttatt gaaaatgatg gagtgcatag acaatggtat    1020
atgcatctaa gtaaatataa tgttaaagta ggagattatg tcaaagctgg tcaaataatc    1080
ggttggtctg gaagcactgg ttattctaca gcaccacatt tacacttcca aagaatggtt    1140
aattcatttt caaattcaac tgcccaagat ccaatgcctt tcttaaagag cgcaggatat    1200
ggaaaagcag gtggtacagt aactccaacg ccgaatacag gttggaaaac aaacaaatat    1260
ggcacactat ataaatcaga gtcagctagc ttcacaccta atacagatat aataacaaga    1320
acgactggtc catttagaag catgccgcag tcaggagtct taaaagcagg tcaaacaatt    1380
cattatgatg aagtgatgaa acaagacggt catgtttggg taggttatac aggtaacagt    1440
ggccaacgta tttacttgcc tgtaagaaca tggaataaat ctactaatac tttaggtgtt    1500
ctttggggaa ctataaagtg a                                              1521
```

<210> SEQ ID NO 94
<211> LENGTH: 506
<212> TYPE: PRT
<213> ORGANISM: artificial
<220> FEATURE:
<223> OTHER INFORMATION: artificial construct

<400> SEQUENCE: 94

```
Met Arg Gly Ser His His His His His His Gly Ser Ala Ala Thr His
1               5                   10                  15

Glu His Ser Ala Gln Trp Leu Asn Asn Tyr Lys Lys Gly Tyr Gly Tyr
            20                  25                  30

Gly Pro Tyr Pro Leu Gly Ile Asn Gly Gly Met His Tyr Gly Val Asp
        35                  40                  45

Phe Phe Met Asn Ile Gly Thr Pro Val Lys Ala Ile Ser Ser Gly Lys
    50                  55                  60

Ile Val Glu Ala Gly Trp Ser Asn Tyr Gly Gly Gly Asn Gln Ile Gly
65                  70                  75                  80
```

```
Leu Ile Glu Asn Asp Gly Val His Arg Gln Trp Tyr Met His Leu Ser
                85                  90                  95

Lys Tyr Asn Val Lys Val Gly Asp Tyr Val Lys Ala Gly Gln Ile Ile
            100                 105                 110

Gly Trp Ser Gly Ser Thr Gly Tyr Ser Thr Ala Pro His Leu His Phe
        115                 120                 125

Gln Arg Met Val Asn Ser Phe Ser Asn Ser Thr Ala Gln Asp Pro Met
    130                 135                 140

Pro Phe Leu Lys Ser Ala Gly Tyr Gly Lys Ala Gly Gly Thr Val Thr
145                 150                 155                 160

Pro Thr Pro Asn Thr Gly Trp Lys Thr Asn Lys Tyr Gly Thr Leu Tyr
                165                 170                 175

Lys Ser Glu Ser Ala Ser Phe Thr Pro Asn Thr Asp Ile Ile Thr Arg
            180                 185                 190

Thr Thr Gly Pro Phe Arg Ser Met Pro Gln Ser Gly Val Leu Lys Ala
        195                 200                 205

Gly Gln Thr Ile His Tyr Asp Glu Val Met Lys Gln Asp Gly His Val
    210                 215                 220

Trp Val Gly Tyr Thr Gly Asn Ser Gly Gln Arg Ile Tyr Leu Pro Val
225                 230                 235                 240

Arg Thr Trp Asn Lys Ser Thr Asn Thr Leu Gly Val Leu Trp Gly Thr
                245                 250                 255

Ile Lys Glu Leu Ala Ala Thr His Glu His Ser Ala Gln Trp Leu Asn
            260                 265                 270

Asn Tyr Lys Lys Gly Tyr Gly Tyr Gly Pro Tyr Pro Leu Gly Ile Asn
        275                 280                 285

Gly Gly Met His Tyr Gly Val Asp Phe Phe Met Asn Ile Gly Thr Pro
    290                 295                 300

Val Lys Ala Ile Ser Ser Gly Lys Ile Val Glu Ala Gly Trp Ser Asn
305                 310                 315                 320

Tyr Gly Gly Gly Asn Gln Ile Gly Leu Ile Glu Asn Asp Gly Val His
                325                 330                 335

Arg Gln Trp Tyr Met His Leu Ser Lys Tyr Asn Val Lys Val Gly Asp
            340                 345                 350

Tyr Val Lys Ala Gly Gln Ile Ile Gly Trp Ser Gly Ser Thr Gly Tyr
        355                 360                 365

Ser Thr Ala Pro His Leu His Phe Gln Arg Met Val Asn Ser Phe Ser
    370                 375                 380

Asn Ser Thr Ala Gln Asp Pro Met Pro Phe Leu Lys Ser Ala Gly Tyr
385                 390                 395                 400

Gly Lys Ala Gly Gly Thr Val Thr Pro Thr Pro Asn Thr Gly Trp Lys
                405                 410                 415

Thr Asn Lys Tyr Gly Thr Leu Tyr Lys Ser Glu Ser Ala Ser Phe Thr
            420                 425                 430

Pro Asn Thr Asp Ile Ile Thr Arg Thr Thr Gly Pro Phe Arg Ser Met
        435                 440                 445

Pro Gln Ser Gly Val Leu Lys Ala Gly Gln Thr Ile His Tyr Asp Glu
    450                 455                 460

Val Met Lys Gln Asp Gly His Val Trp Val Gly Tyr Thr Gly Asn Ser
465                 470                 475                 480

Gly Gln Arg Ile Tyr Leu Pro Val Arg Thr Trp Asn Lys Ser Thr Asn
                485                 490                 495
```

```
Thr Leu Gly Val Leu Trp Gly Thr Ile Lys
            500                 505


<210> SEQ ID NO 95
<211> LENGTH: 1143
<212> TYPE: DNA
<213> ORGANISM: artificial
<220> FEATURE:
<223> OTHER INFORMATION: artificial construct

<400> SEQUENCE: 95

atgagaggat cgcatcacca tcaccatcac ggatccatga gtaaaggaga agaacttttc      60

actggagttg tcccaattct tgttgaatta gatggtgatg ttaatgggca caaattttct     120

gtcagtggag agggtgaagg tgatgcaaca tacggaaaac ttacccttaa atttatttgc     180

actactggaa aactacctgt tccatggcca acacttgtca ctactttcgc gtatggtctt     240

caatgctttg cgagataccc agatcatatg aaacggcatg actttttcaa gagtgccatg     300

cccgaaggtt atgtacagga aagaactata tttttcaaag atgacgggaa ctacaagaca     360

cgtgctgaag tcaagtttga aggtgatacc cttgttaata gaatcgagtt aaaaggtatt     420

gattttaaag aagatggaaa cattcttgga cacaaattgg aatacaacta taactcacac     480

aatgtataca tcatggcaga caaacaaaag aatggaatca aagttaactt caaaattaga     540

cacaacattg aagatggaag cgttcaacta gcagaccatt atcaacaaaa tactccaatt     600

ggcgatggcc ctgtcctttt accagacaac cattacctgt ccacacaatc tgccctttcg     660

aaagatccca acgaaaagag agaccacatg gtccttcttg agtttgtaac agctgctggg     720

attacacatg gcatggatga actatacaaa gagctcggtg gaaagctaga agtaagcaaa     780

gcagcaacta tcaaacaatc tgacgttaag caagaagtta aaaagcaaga agcaaaacaa     840

attgtgaaag caacagattg gaaacagaat aaagatggca tttggtataa agctgaacat     900

gcttcgttca cagtgacagc accagaggga attatcacaa gatacaaagg tccttggact     960

ggtcacccac aagctggtgt attacaaaaa ggtcaaacga ttaaatatga tgaggttcaa    1020

aaatttgacg gtcatgtttg ggtatcgtgg gaaacgtttg agggcgaaac tgtatacatg    1080

ccggtacgca catgggacgc taaaactggt aaagttggta agttgtgggg cgaaattaaa    1140

taa                                                                  1143


<210> SEQ ID NO 96
<211> LENGTH: 380
<212> TYPE: PRT
<213> ORGANISM: artificial
<220> FEATURE:
<223> OTHER INFORMATION: artificial construct

<400> SEQUENCE: 96

Met Arg Gly Ser His His His His His His Gly Ser Met Ser Lys Gly
1               5                   10                  15

Glu Glu Leu Phe Thr Gly Val Val Pro Ile Leu Val Glu Leu Asp Gly
            20                  25                  30

Asp Val Asn Gly His Lys Phe Ser Val Ser Gly Glu Gly Glu Gly Asp
        35                  40                  45

Ala Thr Tyr Gly Lys Leu Thr Leu Lys Phe Ile Cys Thr Thr Gly Lys
    50                  55                  60

Leu Pro Val Pro Trp Pro Thr Leu Val Thr Thr Phe Ala Tyr Gly Leu
65                  70                  75                  80

Gln Cys Phe Ala Arg Tyr Pro Asp His Met Lys Arg His Asp Phe Phe
```

```
                85                  90                  95

Lys Ser Ala Met Pro Glu Gly Tyr Val Gln Glu Arg Thr Ile Phe Phe
            100                 105                 110

Lys Asp Asp Gly Asn Tyr Lys Thr Arg Ala Glu Val Lys Phe Glu Gly
        115                 120                 125

Asp Thr Leu Val Asn Arg Ile Glu Leu Lys Gly Ile Asp Phe Lys Glu
    130                 135                 140

Asp Gly Asn Ile Leu Gly His Lys Leu Glu Tyr Asn Tyr Asn Ser His
145                 150                 155                 160

Asn Val Tyr Ile Met Ala Asp Lys Gln Lys Asn Gly Ile Lys Val Asn
                165                 170                 175

Phe Lys Ile Arg His Asn Ile Glu Asp Gly Ser Val Gln Leu Ala Asp
            180                 185                 190

His Tyr Gln Gln Asn Thr Pro Ile Gly Asp Gly Pro Val Leu Leu Pro
        195                 200                 205

Asp Asn His Tyr Leu Ser Thr Gln Ser Ala Leu Ser Lys Asp Pro Asn
    210                 215                 220

Glu Lys Arg Asp His Met Val Leu Leu Glu Phe Val Thr Ala Ala Gly
225                 230                 235                 240

Ile Thr His Gly Met Asp Glu Leu Tyr Lys Glu Leu Gly Gly Lys Leu
                245                 250                 255

Glu Val Ser Lys Ala Ala Thr Ile Lys Gln Ser Asp Val Lys Gln Glu
            260                 265                 270

Val Lys Lys Gln Glu Ala Lys Gln Ile Val Lys Ala Thr Asp Trp Lys
        275                 280                 285

Gln Asn Lys Asp Gly Ile Trp Tyr Lys Ala Glu His Ala Ser Phe Thr
    290                 295                 300

Val Thr Ala Pro Glu Gly Ile Ile Thr Arg Tyr Lys Gly Pro Trp Thr
305                 310                 315                 320

Gly His Pro Gln Ala Gly Val Leu Gln Lys Gly Gln Thr Ile Lys Tyr
                325                 330                 335

Asp Glu Val Gln Lys Phe Asp Gly His Val Trp Val Ser Trp Glu Thr
            340                 345                 350

Phe Glu Gly Glu Thr Val Tyr Met Pro Val Arg Thr Trp Asp Ala Lys
        355                 360                 365

Thr Gly Lys Val Gly Lys Leu Trp Gly Glu Ile Lys
    370                 375                 380
```

<210> SEQ ID NO 97
<211> LENGTH: 516
<212> TYPE: DNA
<213> ORGANISM: Staphylococcus bacteriophage phi 11

<400> SEQUENCE: 97

```
atgcaagcaa aattaactaa aaatgagttt atagagtggt tgaaaacttc tgagggaaaa      60

caattcaatg tggacttatg gtatggattt caatgctttg attatgccaa tgctggttgg     120

aaagttttgt ttggattact tctaaaaggt ttaggtgcaa aagatattcc gttcgctaac     180

aacttcgacg gattagctac tgtataccaa aatacaccgg acttcttagc acaacctggc     240

gacatggtgg tattcggtag caactacggt gctggatatg gtcacgttgc atgggtaatt     300

gaagcaactt tagattacat cattgtatat gagcagaatt ggctaggcgg tggctggact     360

gacggaatcg aacaacccgg ctggggttgg gaaaaagtta caagacgaca acatgcttat     420

gatttcccta tgtggtttat ccgtccgaat tttaaaagtg agacagcgcc acgatcagtt     480
```

```
caatctccta cacaagcacc taaaaaagaa acagct                              516


<210> SEQ ID NO 98
<211> LENGTH: 158
<212> TYPE: PRT
<213> ORGANISM: Staphylococcus bacteriophage phi 11

<400> SEQUENCE: 98

Met Ser Ile Ile Met Glu Val Ala Thr Met Gln Ala Lys Leu Thr Lys
1               5                   10                  15

Asn Glu Phe Ile Glu Trp Leu Lys Thr Ser Glu Gly Lys Gln Phe Asn
            20                  25                  30

Val Asp Leu Trp Tyr Gly Phe Gln Cys Phe Asp Tyr Ala Asn Ala Gly
        35                  40                  45

Trp Lys Val Leu Phe Gly Leu Leu Leu Lys Gly Leu Gly Ala Lys Asp
    50                  55                  60

Ile Pro Phe Ala Asn Asn Phe Asp Gly Leu Ala Thr Val Tyr Gln Asn
65                  70                  75                  80

Thr Pro Asp Phe Leu Ala Gln Pro Gly Asp Met Val Val Phe Gly Ser
                85                  90                  95

Asn Tyr Gly Ala Gly Tyr Gly His Val Ala Trp Val Ile Glu Ala Thr
            100                 105                 110

Leu Asp Tyr Ile Ile Val Tyr Glu Gln Asn Trp Leu Gly Gly Gly Trp
        115                 120                 125

Thr Asp Gly Ile Glu Gln Pro Gly Trp Gly Trp Glu Lys Val Thr Arg
    130                 135                 140

Arg Gln His Ala Tyr Asp Phe Pro Met Trp Phe Ile Arg Pro
145                 150                 155


<210> SEQ ID NO 99
<211> LENGTH: 642
<212> TYPE: DNA
<213> ORGANISM: Staphylococcus bacteriophage phi 11

<400> SEQUENCE: 99

aagccacaac ctaaagcagt agaacttaaa atcatcaaag atgtggttaa aggttatgac     60

ctacctaagc gtggtagtaa ccctaaaggt atagttatac acaacgacgc agggagcaaa    120

ggggcgactg ctgaagcata tcgtaacgga ttagtaaatg cacctttatc aagattagaa    180

gcgggcattg cgcatagtta cgtatcaggc aacacagttt ggcaagcctt agatgaatca    240

caagtaggtt ggcataccgc taatcaaata ggtaataaat attattacgg tattgaagta    300

tgtcaatcaa tgggcgcaga taacgcgaca ttcttaaaaa atgaacaggc aactttccaa    360

gaatgcgcta gattgttgaa aaaatgggga ttaccagcaa acagaaatac aatcagattg    420

cacaatgaat ttacttcaac atcatgccct catagaagtt cggttttaca cactggtttt    480

gacccagtaa ctcgcggtct attgccagaa gacaagcggt tgcaacttaa agactacttt    540

atcaagcaga ttagggcgta catggatggt aaaataccgg ttgccactgt ctctaatgag    600

tcaagcgctt caagtaatac agttaaacca gttgcaagtg ca                       642


<210> SEQ ID NO 100
<211> LENGTH: 163
<212> TYPE: PRT
<213> ORGANISM: Staphylococcus bacteriophage phi 11

<400> SEQUENCE: 100
```

-continued

```
Asn Pro Lys Gly Ile Val Ile His Asn Asp Ala Gly Ser Lys Gly Ala
1               5                   10                  15

Thr Ala Glu Ala Tyr Arg Asn Gly Leu Val Asn Ala Pro Leu Ser Arg
            20                  25                  30

Leu Glu Ala Gly Ile Ala His Ser Tyr Val Ser Gly Asn Thr Val Trp
        35                  40                  45

Gln Ala Leu Asp Glu Ser Gln Val Gly Trp His Thr Ala Asn Gln Ile
    50                  55                  60

Gly Asn Lys Tyr Tyr Tyr Gly Ile Glu Val Cys Gln Ser Met Gly Ala
65                  70                  75                  80

Asp Asn Ala Thr Phe Leu Lys Asn Glu Gln Ala Thr Phe Gln Glu Cys
                85                  90                  95

Ala Arg Leu Leu Lys Lys Trp Gly Leu Pro Ala Asn Arg Asn Thr Ile
            100                 105                 110

Arg Leu His Asn Glu Phe Thr Ser Thr Ser Cys Pro His Arg Ser Ser
        115                 120                 125

Val Leu His Thr Gly Phe Asp Pro Val Thr Arg Gly Leu Leu Pro Glu
    130                 135                 140

Asp Lys Arg Leu Gln Leu Lys Asp Tyr Phe Ile Lys Gln Ile Arg Ala
145                 150                 155                 160

Tyr Met Asp
```